(12) United States Patent
Abdulazeez et al.

(10) Patent No.: US 10,495,601 B2
(45) Date of Patent: Dec. 3, 2019

(54) RARE EARTH METAL INCORPORATED ZEOLITE MODIFIED ELECTRODES FOR DETECTION AND QUANTIFICATION OF HEAVY METAL IONS IN AQUEOUS SOLUTION

(71) Applicant: KING FAHD UNIVERSITY OF PETROLEUM AND MINERALS, Dhahran (SA)

(72) Inventors: Ismail Abdulazeez, Dhahran (SA); Abdel-Naser M. Kawde, Dhahran (SA); Oki Muraza, Dhahran (SA); Abdul-Rahman Al-Betar, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 387 days.

(21) Appl. No.: 15/446,035

(22) Filed: Mar. 1, 2017

(65) Prior Publication Data
US 2017/0315079 A1    Nov. 2, 2017

Related U.S. Application Data

(60) Provisional application No. 62/330,627, filed on May 2, 2016.

(51) Int. Cl.
*G01N 27/333*    (2006.01)
*G01N 27/48*    (2006.01)
*G01N 27/30*    (2006.01)

(52) U.S. Cl.
CPC ......... *G01N 27/333* (2013.01); *G01N 27/308* (2013.01); *G01N 27/48* (2013.01)

(58) Field of Classification Search
CPC .... G01N 27/333; G01N 27/308; G01N 27/48; G01N 27/3277
See application file for complete search history.

(56) References Cited

FOREIGN PATENT DOCUMENTS

| CN | 100570349 C | 12/2009 |
|---|---|---|
| CN | 103713036 A | 4/2014 |
| CN | 104020213 A | 9/2014 |
| GB | 1 262 019 | 2/1972 |

OTHER PUBLICATIONS

A. Walcarius, et al. "Zeolite-modified solid carbon paste electrode", Journal of Solid State Electrochemistry, 7(10):p. 671-677, Oct. 2003.*
E.F. Sousa-Aguiar, et al. "The role of rare earth elements in zeolites and cracking catalysts", Catalysis Today, v. 218-219, p. 115-127, Dec. 2013.*

(Continued)

*Primary Examiner* — J. Christopher Ball
(74) *Attorney, Agent, or Firm* — Oblon, McClelland, Maier & Neustadt, L.L.P.

(57) ABSTRACT

Electrodes comprising conducting graphite, paraffin oil pasting liquid, and a rare earth metal impregnated zeolite, such as lanthanum or cerium impregnated mordenite electrodes. Methods and voltammetric applications, such as square wave anodic stripping voltammetry, of these rare earth metal impregnated zeolite modified electrodes for the detection and quantification of heavy metal ions such as Pb(II) and Cd(II) in aqueous solutions.

20 Claims, 76 Drawing Sheets

(56) References Cited

OTHER PUBLICATIONS

A. Nezamaedeh-Ejhieh, et al. ("Voltammetric determination of riboflavin based on electrocatalytic oxidation at zeolite-modified carbon paste electrodes", Journal of Industrial and Engineering Chemistry, 20(4): p. 2146-2152, Jul. 2014.*

M. Arvand, et al. "Electrochemical study of atenolol at a carbon paste electrode modified with mordenite type zeolite", Material Science and Engineering C, 30(5): p. 709-714, Jun. 2010.*

A.A. Shaikh, et al. "Direct hydrothermal crystallization of high-silica large-port mordenite", Zeolites 13(7): Abstract only, Sep. 1993.*

A. Ismail, et al., "Lanthanum-impregnated zeolite modified carbon paste electrode for determination of Cadmium (II)", Microporous and Mesoporous Materials, vol. 225, 2016, pp. 164-173.

S. Senthilkumar, et al., "Electrochemical sensing of cadmium and lead ions at zeolite-modified electrodes: Optimization and field measurements", Sensors and Actuators B, vol. 141, 2009, pp. 65-75.

Linyuan Cao, et al. "Sensitive determination of Cd and Pb by differential pulse stripping voltammetry with in situ bismuth-modified zeolite doped carbon paste electrodes", Electrochimica Acta, vol. 53, 2008, pp. 2177-2182.

Beatriz O. Hincapie, et al., "Synthesis of mordenite nanocrystals", Microporous and Mesoporous Materials, vol. 67, 2004, pp. 19-26.

Hisham M. Aly, et al., "Synthesis of mordenite zeolite absence of organic template", Advanced Powder Technology, vol. 23, 2012, pp. 757-760.

Georgia Kefala, et al., "Polymer-coated bismuth film electrodes for the determination of trace metals by sequential-injection analysis/anodic stripping voltammetry", Analytica Chimica Acta, vol. 576, 2006, pp. 283-289.

Gyoung-Ja Lee, et al., "Bismuth nano-powder electrode for trace analysis of heavy metals using anodic stripping voltammetry", Electrochemistry Communications, vol. 9, 2007, pp. 2514-2518.

Watsaka Siriangkhawut, et al., "Sequential injection monosegmented flow voltammetric determination of cadmium and lead using a bismuth film working electrode", Talanta, vol. 79, 2009, pp. 1118-1124.

* cited by examiner

RARE EARTH METAL INCORPORATED ZEOLITE MODIFIED ELECTRODES FOR DETECTION AND QUANTIFICATION OF HEAVY METAL IONS IN AQUEOUS SOLUTION

CROSS REFERENCE TO RELATED APPLICATIONS

This application claims the benefit of priority from U.S. Provisional Application No. 62/330,627 filed May 2, 2016, the entire contents of which are herein incorporated by reference.

BACKGROUND OF THE INVENTION

Technical Field

The present disclosure relates to rare earth metal impregnated zeolite modified electrodes, such as lanthanum or cerium impregnated mordenite electrodes. In addition, the present disclosure relates to applications of these electrodes in voltammetric methods, such as square wave anodic stripping voltammetry, for the detection and quantification of heavy metal ions such as Pb(II) and Cd(II) in aqueous solutions.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Heavy metals are naturally occurring elements, which are found in various concentrations in all ecosystems. Over the years, human activities through technological development and industrial events have resulted in the discharge of heavy metals into the environment which has today become a matter of great concern. While there is still no clear definition of what a heavy metal is, it is sometimes referred to as any metallic element with a high relative density ($>5$ g/cm$^3$) and which is toxic or fatal at even low concentrations [Nagajyoti, P. C., K. D. Lee, and T. V. M. Sreekanth, *Heavy metals, occurrence and toxicity for plants: a review*. Environmental Chemistry Letters, 2010. 8(3): p. 199-216.—incorporated herein by reference in its entirety]. In addition to the density, it has also been established that the chemical properties of the metal are an influencing factor when classifying heavy metals. They include metals such as chromium, lead, cadmium, cobalt, nickel, mercury, iron, silver, arsenic, as well as the platinum group elements. The major risks associated with heavy metals come with exposure to lead, cadmium, mercury and arsenic [Järup, L., *Hazards of heavy metal contamination*. British Medical Bulletin, 2003. 68(1): p. 167-182.—incorporated herein by reference in its entirety].

Cadmium is an extremely toxic metal whose toxicity presents a number of health issues, including major fatal diseases such as heart disease, cancer and diabetes [Shams, E. and R. Torabi, *Determination of nanomolar concentrations of cadmium by anodic-stripping voltammetry at a carbon paste electrode modified with zirconium phosphated amorphous silica*. Sensors and Actuators B: Chemical, 2006. 117(1): p. 86-92.—incorporated herein by reference in its entirety]. Cadmium accumulates in the kidney, liver and various other organs and is considered more harmful than either mercury or lead. In fact, it is harmful even at levels one tenth that of mercury, lead, aluminum or nickel. Exposure to this metal is increasing today as a result of its use as a coating for steel iron and copper. Cadmium is also used in stabilizers, copper alloys, in rubber and plastics, fungicides, cigarette papers, and in many other products. Often, these industries pollute water, air and food with this metal.

Another frequently encountered toxic pollutant in the environment is lead as a result of its use in paints, gasoline and car batteries. Lead is known for its manifestation in the form of several health problems, such as cardiac, mental and neurological disorders. As many as thirty important health conditions have been linked lead, many of which affect children and the unborn. It has also been reported that the function of lead in the body is unknown. Lead can substitute for calcium in bones and may delay osteoporosis (a medical condition which causes the bones to become weak and brittle). However, lead causes other metabolic problems in the body, and hence calcium is the preferred element. Symptoms of lead toxicity may appear years after exposure, as a result of the sudden release of stored lead due to illness, alcoholism, stress or other metabolic changes. Sources of lead include paints, radioactive disintegration of uranium, car batteries, lead pipes, hair colorings, and the like.

Mercury is one of the members of the class of toxic metals which have been recognized since prehistoric times. It is poisonous in any form, with its toxicity commonly affecting the neurological, gastrointestinal and renal organ systems. Poisoning from mercury can occur as a result of vapor inhalation, injection, ingestion, and penetration through the skin. It exists in three forms: elemental, organic and inorganic forms. The three forms are interconvertible, and can all produce systemic toxicity. Mercury is widely used in industry and in a variety of products, such as fungicides, algaecides used in swimming pools, in the manufacture of adhesives, floor waxes, fabric softeners, and in the production of chlorine.

Another harmful carcinogen to both humans and animals is arsenic. Its toxicity has been linked with cancers of the bladder, skin and lung. It is estimated that as many as tens of millions of people are at risk of exposure to enormous levels of arsenic as a result of exposure to contaminated water and arsenic containing coal from natural sources [Ng, J. C., J. Wang, and A. Shraim, *A global health problem caused by arsenic from natural sources*. Chemosphere, 2003. 52(9): p. 1353-1359.—incorporated herein by reference in its entirety]. Chronic arsenic exposure may lead to skin cancer, diabetes, black foot disease, papillary and cortical necrosis, and the like. Table 1 summarizes the maximum contaminant level (MSL) allowed of some inorganic contaminants in domestic water, their common sources, and their potential health effects as adapted from the EPA National Primary Drinking Water Standards tables [Patterson, K. Y., P. R. Pehrsson, and C. R. Perry, *The mineral content of tap water in United States households*. Journal of Food Composition and Analysis, 2013. 31(1): p. 46-50.—incorporated herein by reference in its entirety].

TABLE 1

Maximum contaminant levels of inorganic chemicals allowed in drinking water

| Contaminant | MCL (ppm) | Common Source | Potential Health Effect |
|---|---|---|---|
| Arsenic (As) | 0.01 | Drainage from glass and electronic production waste | Skin damage; prospect of getting cancer |
| Barium (Ba) | 2 | Release of drilling wastes, and metal refineries | Increase in blood pressure |
| Cadmium (Cd) | 0.005 | Decay of galvanized pipes; release from metal refineries, drainage from waste batteries and paints | Kidney impairment |
| Chromium (Cr) | 0.1 | Release from steel and pulp mills | Allergic dermatitis |
| Lead (Pb) | 0.015 | Decay of household plumbing systems | Kidney diseases and high blood pressure in adults |
| Mercury (Hg) (inorganic) | 0.002 | Release from refineries and factories | Kidney damage |
| Selenium (Se) | 0.005 | Release from petroleum and metal refineries | Hair or fingernail loss, circulatory problems |
| Thallium (Tl) | 0.002 | Seep from ore-processing sites, release from electronics, glass, and drug factories | Loss of hair, kidney, intestine or liver complications |
| CN⁻ (as free cyanide) | 0.2 | Release from steel factories, discharge from plastic and fertilizer factories | Nerve damage or thyroid complications |
| Fluoride (F⁻) | 4.0 | Water supplement which enhances strong teeth | Bone infections (pain and tenderness of bones) |

Several methods exist for the detection of heavy metals. Optical methods include spectroscopic techniques such as atomic absorption spectrometry (AAS), graphite furnace atomic absorption spectrometry (GFAAS), inductively coupled plasma-optical emission spectrometry (ICP-OES), inductively coupled plasma-mass spectrometry (ICP-MS) and the like.

Atomic absorption spectrometry (AAS) is a common spectroscopic technique for the qualitative determination of chemical elements using the absorption of optical radiation by free atoms in the gaseous state. The atoms absorb ultraviolet or visible light and make transitions to higher energy levels. A detector measures the wavelengths of light transmitted by the sample, and compares them to the wavelength which originally passed through the sample. A signal processor then integrates the change in wavelength absorbed, which appear in the read-out as peaks of energy absorption at discrete wavelengths. All atoms have their distinct pattern of wavelengths at which they will absorb energy, due to the unique configuration of electrons in their outer shells. The concentration of the analyte is then calculated based on the Beer-Lambert law as given by the equation of formula (I).

$$A = \varepsilon b C \quad (I):$$

In this equation, A is absorbance, E is a molar absorptivity coefficient, b is the path length, and C is the concentration.

Graphite furnace atomic absorption spectrometry (GFAAS) is a technique that possesses the same working principle as AAS. The difference between the two is the way in which the sample is injected into the instrument. In GFAAS, an electrothermal graphite furnace is used. The sample is heated gradually (up to 3000° C.) until it dries before being atomized and subsequently analyzed. The advantage of GFAAS over AAS is that the limit of detection in GFAAS is about two orders of magnitude greater than that of AAS.

Inductively coupled plasma-optical emission spectrometry (ICP-OES) is among the most robust analytical tools for the measurement of trace elements in numerous types of samples. The working principle of ICP-OES relies upon the rapid release of photons from atoms and ions that have been excited in a radio frequency (RF) discharge. One major advantage of this technique is the fact that it can analyze samples of any form (solid, liquid or gaseous). The sample solution is transformed to an aerosol and sent into the central channel of the plasma. At its core the plasma sustains a temperature of approximately 10,000 K, such that the aerosol is quickly vaporized. Analyte elements are released as free atoms in the gaseous state. An ample amount of energy is often available to transform the atoms to ions and later to promote the ions to excited states. Bothe the atomic and ionic excited state species may then return to the ground state with the emission of a photon. These photons possess characteristic energies that are determined by the quantized energy level structure for the atoms or ions. Hence, the wavelength of the photons can be used to identify the elements from which they were emitted. The total number of emitted photons is directly proportional to the concentration of the element in the sample.

One major disadvantage of the optical techniques discussed herein is that they require highly sophisticated instrumentation, and are not suitable for on-site monitoring. Alternatively, electroanalytical techniques offer a simple approach with several advantages, such as rapid analysis, portability, good selectivity and sensitivity. Voltammetric techniques, and stripping techniques in particular are well suited for the determination of trace amounts of heavy metals due to their speed, remarkable analytical sensitivity, simplicity, low cost, and minimum sample pre-treatment [Prabakar, S. J. R., C. Sakthivel, and S. S. Narayanan, *Hg(II) immobilized MWCNT graphite electrode for the anodic stripping voltammetric determination of lead and cadmium.* Talanta, 2011. 85(1): p. 290-297.—incorporated herein by reference in its entirety]. Electroanalytical techniques are among the most powerful and popular techniques used in analytical chemistry. The techniques offer a remarkable sensitivity, accuracy, and precision in addition to a large linear dynamic range, with relatively low cost instrumentation. The electroanalytical techniques have found applications in areas such as environmental studies, industrial quality control, biomedical analysis, and so on. They include techniques such as; cyclic voltammetry (CV), linear sweep voltammetry (LSV), normal pulse voltammetry (NPV), differential pulse voltammetry (DPV), square wave voltammetry (SWV), anodic stripping voltammetry (ASV), cathodic stripping voltammetry (CSV), and the like.

Cyclic voltammetry (CV) is an electrochemical technique where the potential at a working electrode is changed linearly with time while measuring the resulting current. This gives rise to voltammograms which provide information about the reactivity and mass transport properties of an electrolyte. CV is one of the most widely used electroanalytical methods because of its ability to study and characterize redox systems from macroscopic scales down to nanoelectrodes as well as composite electrodes. An exemplary typical CV voltammogram is shown in FIG. 1 [Ivaska, A. and J. Bobacka, *PROCESS ANALYSIS|Electroanalytical Techniques, in Encyclopedia of Analytical Science (Second Edition),* P. W. T. Poole, Editor. 2005, Elsevier: Oxford. p.

309-316.—incorporated herein by reference in its entirety]. In FIG. 1 $E_{p,c}$ and $E_{p,a}$ are the peak potential at the cathode and anode, respectively, and $i_{p,c}$ and $i_{p,a}$ are the peak currents at the cathode and anode, respectively. The peak current in CV is given by the Randles-Sevcik equation of formula (II).

$$i_p = (2.69 \times 10^5) n^{3/2} A D^{1/2} v^{1/2} C \qquad (II)$$

In this equation, n is the number of electrons in the redox system, A is the area of the working electrode, D is the diffusion coefficient of the electroactive species, v is the scan rate and C is the concentration of the electroactive specie at the electrode.

Cyclic voltammetry provides qualitative information about electrochemical processes under different conditions, which include the presence of intermediates in redox reactions and the reversibility of a reaction. It is also used to determine the electron stoichiometry of a system, the diffusion coefficient of an analyte, and the formal reduction potential, which can be used as an identification tool. Additionally, because concentration is proportional to current in a reversible, Nernstian system, concentration of an unidentified solution can be found by generating a calibration curve of current versus concentration.

In linear sweep voltammetry (LSV), potential is varied at a constant rate while the current is measured. The rate of change of the potential is called the scan rate (v). Traditionally, the potential is plotted on the x-axis with more negative (i.e. reducing) potentials to the right. Currents, in contrast, are graphed on the y-axis with currents due to reduction assigned positive values. In LSV, it is common practice to measure the peak current ($i_p$), the largest current; peak potential ($E_p$), the potential at the peak current and the half-peak potential ($E_{1/2}$), which is the potential when the current is half of the peak current. The potential at the peak is characteristic of the system being investigated. It is mainly a thermodynamic measurement, but may be affected by the kinetics of the system. The value of the peak current depends on several factors including the analyte concentration, kinetics of electron transfer and the mass transport of the analyte. FIG. 2 shows and exemplary typical LSV voltammogram of ferrocene. In a diffusion controlled system, with reversible electron transfer, the relationship is given by an equation of formula (III).

$$i_p = (2.69 \times 10^5) n^{3/2} A D^{1/2} v^{1/2} C^* \qquad (III)$$

In this equation, C* is the bulk concentration of analyte (mol analyte/cm$^3$) and all other variables and symbols are the same as in the Randles-Sevcik equation. The dependence on bulk concentration (rather than concentration at the electrode surface (allows peak current to be used for quantitative purposes.

Normal pulse voltammetry (NPV) consists of stages of pulses of rising amplitude applied to successive drops at a preselected tem close to the end of each drop lifetime, while the electrode is maintained at a base potential between pulses where no reaction occurs. Current is measured at around 40 ms after each pulse is applied and is graphed as a function of the potential. The resulting voltammogram has a sigmoidal shape, with a limiting current represented by a modified Cottrell equation of formula (IV).

$$\frac{nFACD^{1/2}}{\sqrt{\pi t_m}} \qquad (IV)$$

In this equation, $t_m$ is the time after application of the pulse where the current is measured. An exemplary typical signal for normal pulse voltammetry is shown in FIG. 3.

Differential pulse voltammetry (DPV) is a very useful technique for detecting trace amounts of organic and inorganic species. In DPV, fixed magnitude pulses superimposed on a linear potential ramp are applied to the working electrode just before the end of the drop (FIG. 4). The current is measured twice, before the pulse application and after the pulse (after ~40 ms, when the charging current goes down). The first current is instrumentally deducted from the second, and this current difference is graphed against the applied potential. The resulting differential pulse voltammogram consists of current peaks, whose height is directly proportional to the concentration of the corresponding analyte. The peak potential ($E_p$) appears close to the polarographic half wave potential and can be used to identify the species. This technique is useful for analyzing mixtures with very low detection limits. It is also used to yield information about the chemical nature of the analyte.

Square wave voltammetry (SWV) is a robust electrochemical technique suitable for analytical applications, mechanistic studies of electrode processes and electrokinetic measurements [Mirceski, V., et al., *Square-Wave Voltammety: A Review on the Recent Progress*. Electroanalysis, 2013. 25(11): p. 2411-2422.—incorporated herein by reference in its entirety]. In this technique, current is measured twice during each square wave cycle, once at the completion of the forward pulse, and once at the completion of the reverse pulse. Because the square wave modulation amplitude is very large, the reverse pulse leads to the reverse reaction of the product (of the forward pulse). Thus, the difference between the two measurements is graphed versus the base staircase potential. This is shown in FIG. 5. A plot of the theoretical forward, reverse and difference currents is given in FIG. 6 for a reversible redox system. The resulting peak shaped voltammogram is symmetric about the half wave potential, and the peak current is proportional to the concentration. The major advantage of this technique over other electrochemical techniques is its speed, sensitivity, and the fact that it can reach very low limits of detection.

Anodic stripping voltammetry (ASV) is one of the most common of a class of techniques known as stripping electoranalytical methods. The distinguishing property of this technique is the deposition of analyte at the surface of the electrode, and thus a lowered detection limit for the analyte. ASV involves the deposition of electroactive species at the electrode surface by the application of a negative potential. In most cases a mercury drop electrode or mercury thin film electrode is used under forced convective conditions (i.e. stirred solution). The deposition step is followed by a short time period in which the solution is allowed to quiet (i.e. no stirring), after which a potential scan is initiated from the deposition potential in the anodic direction. From the resulting voltammogram, the current magnitude (peak height) or charge (peak area) is then used to quantify unknown amounts of analyte. For a mercury film deposited on the surface of an inert substrate, the stripping peak current is given by an equation of formula (V).

$$\frac{n^2 F^2 v^{1/2} A l C_M}{2.7 RT} \qquad (V)$$

In this equation, F represents the Faraday (9.65×10⁴ C), l is the mercury film thickness in cm, and all other variables and symbols are the same as previously defined.

Cathodic stripping voltammetry (CSV) is the mirror image of ASV. CSV involves anodic deposition of the analyte, followed by stripping in the negative potential scan as described by formula (VI).

$$A^{n-} + Hg \leftrightarrow HgA + ne^- \qquad (VI):$$

The resulting peak current provides the desired quantitative information. CSV is used to measure a wide range of organic and inorganic compounds, capable of forming insoluble salts with mercury. Examples are thiols or penicillin, as well as halide, cyanide, and sulfide ions.

Working electrodes are often employed in electroanalytical techniques. The working electrode (WE) is a crucial component of an electrochemical cell. This is because the electron transfer of interest occurs at its surface. The selection of the material for this electrode is therefore a critical issue to the analysis. Several factors are considered when selecting the material for the working electrode. First, it should possess favorable redox behavior with the analyte (i.e. it should enable reproducible electron transfer without electrode contamination). Second, the potential window over which the electrode works in a given electrolyte solution should be as wide as possible to allow for the greatest degree of analyte characterization. Other factors considered include the cost of the material, its ability to be turned into useful geometries, the ease of surface renewal after analysis, and the material's toxicity [Imisides, M. D., G. G. Wallace, and E. A. Wilke, *Designing chemically modified electrodes for electroanalysis*. TrAC Trends in Analytical Chemistry, 1988. 7(4): p. 143-147.—incorporated herein by reference in its entirety]. The most commonly used working electrode materials are Pt, Au, C, and Hg. FIG. 7 presents examples of working electrodes employed in electroanalytical chemistry.

As a result of its inertness, platinum (Pt) is one of the most preferred electrodes in electroanalytical studies. However, the major drawback to the use of this electrode, aside from its high cost is that the presence of small amounts of water or acid in the electrolyte leads to the reduction of hydrogen ion to form hydrogen gas at fairly modest negative potentials. This reduction interferes with any useful analytical signal. Gold (Au) electrodes have limited application in the positive potential range due to the ease of oxidation at their surface. Hence, this electrode is not generally preferred in electrochemical studies. Carbon (C) electrodes have advantages over platinum and gold electrodes because they enable scans to more negative potentials, and possess good anodic potential windows. The most prevalent form of carbon electrode is glassy carbon, which is relatively costly and difficult to machine. Carbon paste electrodes have also found usefulness in several applications. These electrodes are made from a paste of finely granulated carbon mixed with an oil substrate (usually Nujol or paraffin). The resulting paste is then packed into the cavity of an inert electrode body. These electrodes have the drawback of being susceptible to mechanical damage during use. Mercury (Hg) is another classic type of electrode material. Due to its high hydrogen overvoltage, it can extend the cathodic potential window. In addition, mercury electrodes possess a highly reproducible, renewable and smooth surface, which is very beneficial in electrochemical analyses. Among the mercury electrodes, the dropping mercury electrode (DME) is the most commonly preferred. This is because in these electrodes drops of mercury form and fall off continuously during a potential scan. This yields the advantage of self-renewal, so it does not need to be cleaned or polished before each experiment. However, the toxic nature of mercury has restricted the broader use of this electrode for electroanalytical studies.

Zeolite modified electrodes (ZMEs) belong to a class of the so called "chemically modified electrodes" (CMEs). From an electrochemical perspective, zeolites offer a nanostructured domain, where the physical structure and the chemical nature of the zeolite affects electron transfer reactions and influences known chemical steps coupled with the electron transfer at the electrode and solution interfaces. This results in the fabrication of electrodes with high sensitivity, high selectivity, and a wide dynamic range. The advent of zeolite modified electrodes (ZMEs) has over the past 15 years attracted the attention of researchers in the field of electrochemistry and other similar fields [Walcarius, A., P. Mariaulle, and L. Lamberts, *Zeolite-modified solid carbon paste electrodes*. Journal of Solid State Electrochemistry, 2003. 7(10): p. 671-677.—incorporated herein by reference in its entirety]. In addition, the incorporation of zeolites into carbon electrodes imparts a number of chemical, physical and structural features of high interest in the design and development of electroanalytical systems. These include shape, size and charge selectivities, physical and chemical stabilities, high ion exchange capacity as well as hydrophilic character [Walcarius, A., *Zeolite-modified electrodes in electroanalytical chemistry*. Analytica Chimica Acta, 1999. 384 (1): p. 1-16.—incorporated herein by reference in its entirety].

Zeolites are crystalline materials that afford molecular sized frames and pores for excellent steric control of reaction paths [Ojani, R., et al., *Electrochemical behavior of Ni(II) incorporated in zeolite Y-modified carbon electrode: application for electrocatalytic oxidation of methanol in alkaline solution*. Journal of Solid State Electrochemistry, 2011. 15(9): p. 1935-1941.—incorporated herein by reference in its entirety]. The major building units of zeolites are $[SiO_4]^{4-}$ and $[AlO_4]^{5-}$ tetrahedral. These units can link in several ways, resulting in arrays producing three-dimensional anionic networks. The extra negative charge on $[AlO_4]^{5-}$ tetrahedral is counter balanced by a cation, maintaining the overall neutrality of the zeolite. Zeolites have been used for various industrial and catalytic purposes, the most important of which is their use in fluid catalytic cracking (FCC) which supplies about 45% of the global gasoline pool by the cracking of larger hydrocarbons into the respective gasoline fractions [Taarning, E., et al., *Zeolite-catalyzed biomass conversion to fuels and chemicals*. Energy & Environmental Science, 2011. 4(3): p. 793-804.—incorporated herein by reference in its entirety]. Today, over 200 zeolite and zeotype structures are recognized by the International Zeolite Association (IZA), which includes MFI, BEA, MEL, MTW, MOR, FER, FAU, etc. [Pophale, R., P. A. Cheeseman, and M. W. Deem, *A database of new zeolite-like materials*. Physical Chemistry Chemical Physics, 2011. 13(27): p. 12407-12412.—incorporated herein by reference in its entirety].

In the past, the composition of zeolites was limited to aluminosilicate polymorphs. However, in recent years heteroatoms such as Ta, Ge, Fe, V, Sn, P, Ti, and B, among others are now incorporated into the zeolite structure alongside silicon and aluminum [Moliner, M., C. Martinez, and A. Corma, *Synthesis Strategies for Preparing Useful Small Pore Zeolites and Zeotypes for Gas Separations and Catalysis*. Chemistry of Materials, 2014. 26(1): p. 246-258.—incorporated herein by reference in its entirety]. This large chemical utility has enable the control of the physicochemical activities of zeolites (such as acidity, redox properties, or hydrophobic-hydrophilic nature), and as a result, there has been an increased number of applications of these materials [Davis, M. E. and R. F. Lobo, *Zeolite and molecular sieve synthesis*. Chemistry of Materials, 1992. 4(4): p. 756-768.—incorporated herein by reference in its entirety]. More recently, the introduction of additional rare earth (RE) elements such as La and Ce into zeolite compositions with the aim of improving the stability and enhancing the zeolite activity has been investigated [Sousa-Aguiar, E. F., F. E. Trigueiro, and F. M. Z. Zotin, *The role of rare earth elements in zeolites and cracking catalysts*. Catalysis Today, 2013. 218-219(0): p. 115-122.—incorporated herein by reference in its entirety].

Several authors have reported the improvement in the stability of zeolites after the addition of rare earth elements such as La, Ce, Nd, Sm, and Pr. Such properties have been attributed to the formation of hydroxyl rare earth cation species in zeolite channels [Bartlett, J. R., R. P. Cooney, and R. A. Kydd, *Hydrolysis of europium cations in zeolite X: A fourier transform infrared spectroscopic study*. Journal of Catalysis, 1988. 114(1): p. 53-57.—incorporated herein by reference in its entirety]. It was also found that the incorporation of rare earth element ions into zeolite frameworks tends to alter the Lewis acid sites in the framework, and this in turn enhances the zeolite's catalytic activity [Pang, X., et al., *Effects of metal modifications of Y zeolites on sulfur reduction performance in fluid catalytic cracking process*. Catalysis Today, 2007. 125(3-4): p. 173-177.—incorporated herein by reference in its entirety]. Zeolites are also made catalytically more active and thermally more stable at their operating temperatures by incorporating rare earth element ions in them [Gu, J., et al., *Hydrothermal incorporation of Ce(La) ions into the framework of ZSM-5 by a multiple pH-adjusting co-hydrolysis*. Journal of Porous Materials, 2013. 20(1): p. 7-13.—incorporated herein by reference in its entirety]. The introduction of rare earth elements is used to adjust the amount and intensity of distribution of the acid sites in the zeolites. For example in FCC, catalysts are generally used at high temperatures and in hydrothermal environments. These conditions usually induce a decline in the degree of crystallinity, deterioration of the aluminum leaching framework and consequent collapse in the zeolite structure, which result in the deactivation of the catalyst. The introduction of rare earth element ions into the zeolite framework was therefore reported to help stabilize the zeolite framework [Zhan, W., et al., *Current status and perspectives of rare earth catalytic materials and catalysis*. Chinese Journal of Catalysis, 2014. 35(8): p. 1238-1250.—incorporated herein by reference in its entirety].

Mordernite is an industrially important member of the zeolite family with the ideal composition of $Na_8Al_8Si_{40}O_{96} \cdot nH_2O$. Its framework is built on 5-membered rings arranged in columns parallel to the [001] axis. Hence, the framework includes elliptical micropore (6.7×7.0 Å) tunnels parallel to the c-axis and (2.6×5.7 Å) tunnels parallel to the b-axis [Aly, H. M., M. E. Moustafa, and E. A. Abdelrahman, *Synthesis of mordenite zeolite in absence of organic template*. Advanced Powder Technology, 2012. 23(6): p. 757-760; and Sano, T., et al., *Synthesis of large mordenite crystals in the presence of aliphatic alcohol*. Microporous and Mesoporous Materials, 2001. 46(1): p. 67-74.—each incorporated herein by reference in its entirety]. By virtue of the small nature of the latter axis, molecules are unable to pass through and as such mordenite is generally regarded as a one-dimensional zeolite [Li, X., R. Prins, and J. A. van Bokhoven, *Synthesis and characterization of mesoporous mordenite*. Journal of Catalysis, 2009. 262(2): p. 257-265.—incorporated herein by reference in its entirety]. Due to its high thermal and acid stabilities, mordenite has been used in several applications, such as in the separation of gas or liquid mixtures and in catalysis such as hydrocracking, hydro-isomerization, alkylation, reforming, dewaxing and in the synthesis of dimethyl amines [Lu, B., et al., *Direct synthesis of high-silica mordenite using seed crystals*. Microporous and Mesoporous Materials, 2004. 76(1-3): p. 1-7; and Fernandes, L. D., et al., *Ethylbenzene hydroisomerization over bifunctional zeolite based catalysts: The influence of framework and extraframework composition and zeolite structure*. Journal of Catalysis, 1998. 177(2): p. 363-377.—each incorporated herein by reference in its entirety]. Additionally, more recently, it has been considered for use in semiconductors, chemical sensors, and nonlinear optical materials. FIG. 8 shows the framework of mordenite zeolite [Baerlocher, C., L. B. McCusker, and D. H. Olson, *MOR—Cmcm*, in *Atlas of Zeolite Framework Types (Sixth Edition)*, C. Baerlocher and L. B. M. H. Olson, Editors. 2007, Elsevier Science B. V.: Amsterdam. p. 218-219.—incorporated herein by reference in its entirety].

Several reports have been published on the role played by metals in enhancing the electrocatalytic activity of zeolites [Kaur, B., M. U. Anu Prathap, and R. Srivastava, *Synthesis of Transition-Metal Exchanged Nanocrystalline ZSM-5 and Their Application in Electrochemical Oxidation of Glucose and Methanol*. ChemPlusChem, 2012. 77(12): p. 1119-1127; and Mojović, Z., et al., *Carbon monoxide electrooxidation on Pt and PtRu modified zeolite X*. Journal of Porous Materials, 2012. 19(5): p. 695-703; and Guzmán-Vargas, A., et al., *Efficient electrocatalytic reduction of nitrite species on zeolite modified electrode with Cu-ZSM-5*. Electrochimica Acta, 2013. 108(0): p. 583-590; and Raoof, J. B., et al., *Synthesis of ZSM-5 zeolite: Electrochemical behavior of carbon paste electrode modified with Ni (II)-zeolite and its application for electrocatalytic oxidation of methanol*. International Journal of Hydrogen Energy, 2011. 36(20): p. 13295-13300; and Li, Y.-J. and C.-Y. Liu, *Silver-exchanged zeolite Y-modified electrodes: size selectivity for anions*. Journal of Electroanalytical Chemistry, 2001. 517(1-2): p. 117-120; and Cao, L., J. Jia, and Z. Wang, *Sensitive determination of Cd and Pb by differential pulse stripping voltammetry with in situ bismuth-modified zeolite doped carbon paste electrodes*. Electrochimica Acta, 2008. 53(5): p. 2177-2182; and Kaur, B. and R. Srivastava, *Simultaneous electrochemical determination of nanomolar concentrations of aminophenol isomers using nanocrystalline zirconosilicate modified carbon paste electrode*. Electrochimica Acta, 2014. 141(0): p. 61-71.—each incorporated herein by reference in its entirety]. Table 2 summarizes some of these studies.

TABLE 2

Summary of zeolite literature

| Zeolite | Metal impregnated | Characterization Technique | Application | Reference |
|---|---|---|---|---|
| Zeolite Y | Ni | Cyclic voltammetry | Electroanalytic oxidation of methanol in alkaline solution | Ojani, et al. |
| ZSM-5 | Cu, Ni, Co, Fe, and Mn | Cyclic voltammetry | Electrochemical oxidation of glucose and methanol | Kaur, et al. |
| Zeolite X | Pt and Pt/Ru | Cyclic voltammetry | Carbon monoxide electrooxidation | Mojovic, et al. |
| ZSM-5 | Cu | Cyclic voltammetry | Electrocatalytic reduction of nitrite species | Guzman-Vargas, et al. |
| ZSM-5 | Ni | Cyclic voltammetry | Electrocatalytic oxidation of methanol | Raoof, et al. |
| Zeolite Y | Ag | Cyclic voltammetry | Electroactiviry in aqueous solutions of different anions | Li, et al. |
| Synthetic zeolite | Bi | Differential pulse square wave voltammetry | Determination of trace amounts of Cd and Pb | Cao, et al. |
| ZSM-5 | Zr | Cyclic voltammetry | Simultaneous electrochemical determination of nano-molar concentrations of aminophenol isomers | Kaur, et al. |

In one study, Li, et al. examined the electrochemical performance of an Ag ion-incorporated zeolite Y-modified electrode in aqueous solution containing different anions. It was shown that the Ag ion-exchanged zeolite Y-modified electrode has a high selectivity for Cl⁻ and Br⁻ anions. In other research, Kauer, et al. investigated the role played by various transition metals in the electrocatalytic oxidation of glucose on a ZSM-5 modified electrode. Metals studied included Cu, Ni, Co, Fe and Mn. It was found that a non-enzymatic electrochemical sensor based on a $Ni^{2+}$ exchanged nanocrystalline ZSM-5-modified electrode exhibited the highest sensing ability towards oxidation whereas the corresponding $Cu^{2+}$ exchanged electrode exhibits the highest current sensitivity for glucose oxidation. It was therefore concluded that the enhancement in the electrocatalytic activities of nanocrystalline ZSM-5 modified electrodes is due to the enhanced accessibility of glucose/methanol to M2+ active centers in the nanocrystalline ZSM-5 owing to its large specific surface area and intercrystalline mesopores.

Guzman, V., et al. also studied the effect of Cu(II) ion incorporation into ZSM-5 modified electrode in the reduction of nitrite species. It was found that the Cu(II) ion incorporated modified electrode exhibits good electrocatalytic activity towards the reduction of nitrite species. It was also found that the activity increases as the Si/Al ratio of the zeolite decreases. The influence of incorporating Ni(II) ion into the framework of zeolite Y for the electrocatalytic oxidation of methanol was also investigated by Ojani, et al. It was found that the modified electrode prepared by both methods of cation exchange and open circuit accumulation of Ni ion on the surface of the electrode displayed advantageous catalytic activity in alkaline solution. They also studied the effect of the ratio of graphite to zeolite on electrocatalytic current and found that the ratio of 3:1 of graphite to zeolite was the determined ratio for advantageous electrocatalytic activity.

In another study, the analytical performance of a Bi modified zeolite doped carbon paste electrode was investigated for trace analysis of Cd and Pb. Bi ion was incorporated into a commercial zeolite (synthetic zeolite) and this was used in the preparation of the modified electrode by mixing with graphite and silicone oil (binder). The electrochemical behavior of this electrode was studied by a stripping technique in 0.10 M sodium acetate buffer solution (pH 4.5) before its application for the determination of Cd an Pb levels. It was found that the in situ plated (zeolite/graphite powder/silicone, 10/190/80 w/w) exhibited the most sensitive response to Cd and Pb in 0.10 M acetate buffer, and the detection limits of 0.08 $\mu gL^{-1}$ and 0.10 $\mu gL^{-1}$ were obtained for Cd(II) and Pb(II), respectively. The results obtained were found to agree with those obtained by atomic absorption spectroscopy (AAS). The role played by metals such as Zr, Ti, and Al when incorporated into zeolite-modified electrodes was also studied by Kaur, et al. using nano-ZSM-5 zeolite. The electrochemical behavior of this electrode studied by cyclic voltammetry revealed that a nano-Zr-ZSM-5/carbon paste electrode exhibited excellent stability, high sensitivity and selectivity. This electrode was applied in the determination of nanomolar concentrations of aminophenol isomers and the detection limits were found to be 26 nM, 30 nM, and 30 nM for p-aminophenol, o-aminophenol, and m-aminophenol, respectively.

In view of the forgoing, one object of the present disclosure is to provide zeolite modified electrodes designed towards trace metal analysis, specifically rare earth metal impregnated zeolite modified carbon past electrodes (RE-ZMCPEs) such as lanthanum and cerium incorporated mordenite zeolite electrodes. This disclosure provides the synthesis and characterization of these materials and electrodes. An additional aspect of the present disclosure is application of these electrodes in methods of electroanalytical voltammetric detection and quantification of heavy metal ions in aqueous solutions, such as the square wave anodic stripping voltammetric determination of Cd(II) and Pb(II) in aqueous samples. It is envisioned that these electrodes will display low detection limits, at or below the maximum contaminant level, with good reproducibility. Overall, the electrodes of the present disclosure are envisaged to exhibit strong potential utility in the analysis of environmental samples due to their inexpensiveness, ease of fabrication and relative lack of toxicity compared to alternative electrodes, such as mercury based electrodes.

BRIEF SUMMARY OF THE INVENTION

According to a first aspect, the present disclosure relates to an electrode comprising: i) graphite powder, ii) paraffin oil, and iii) a zeolite impregnated with a rare earth metal.

In one embodiment, the zeolite is a mordenite zeolite which has a silica to alumina ratio in the range of 5 to 40.

In one embodiment, the rare earth metal is at least one selected from the group consisting of lanthanum and cerium.

In one embodiment, the zeolite impregnated with the rare earth metal has a weight percentage of the rare earth metal in the range of 1-15% relative to the total weight of the zeolite impregnated with the rare earth metal.

In one embodiment, the electrode has weight percentage of the graphite powder in the range of 45-75% relative to the total weight of the electrode.

In one embodiment, the electrode has a weight percentage of the zeolite impregnated with the rare earth metal in the range of 1-30% relative to the total weight of the electrode.

In one embodiment, the electrode has a weight percentage of the paraffin oil in the range of 20-40% relative to the total weight of the electrode.

In one embodiment, the electrode has a 10-40% greater electroactive surface area relative to a substantially similar electrode lacking the zeolite impregnated with the rare earth metal.

According to a second aspect, the present disclosure relates to a method for detecting and quantifying a heavy metal ion in an aqueous solution comprising: i) contacting the aqueous solution with the electrode in any of its embodiments, ii) generating a negative deposition potential at the electrode to reduce the heavy metal ion and form a reduced heavy metal that is deposited onto the electrode, iii) scanning a potential range from the negative deposition potential in the positive direction at the electrode to oxidize and strip the reduced heavy metal from the electrode, and iv) measuring the current during the scanning.

In one embodiment, the heavy metal ion is at least one selected from the group consisting of Pb(II) and Cd(II).

In one embodiment, the scanning and the measuring are performed with square wave voltammetry.

In one embodiment, the negative deposition potential is in the range of $-2.0$ V to $-0.2$ V.

In one embodiment, the scanning is performed at a scan rate of 2-500 mV s$^{-1}$.

In one embodiment, the reduced heavy metal is deposited over a time period in the range of 10-250 seconds.

In one embodiment, the rare earth metal is lanthanum and the heavy metal ion is Pb(II), and the method has a Pb(II) detection limit in the range of 0.15-0.30 µg L$^{-1}$.

In one embodiment, the rare earth metal is lanthanum and the heavy metal ion is Cd(II), and the method has a Cd(II) detection limit in the range of 0.05-0.20 µg L$^{-1}$.

In one embodiment, the rare earth metal is cerium and the heavy metal ion is Pb(II), and the method has a Pb(II) detection limit in the range of 0.02-0.15 µg L$^{-1}$.

In one embodiment, the rare earth metal is cerium and the heavy metal ion is Cd(II), and the method has a Cd(II) detection limit in the range of 0.01-0.10 µg L$^{-1}$.

In one embodiment, the method has a reproducibility as measured by a relative standard deviation in the range of 1-5%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

30 at an accumulation potential of −1.2 V, an accumulation time of 120 seconds, a potential step of 5 mV, and an amplitude of 300 mV.

Figure 64:
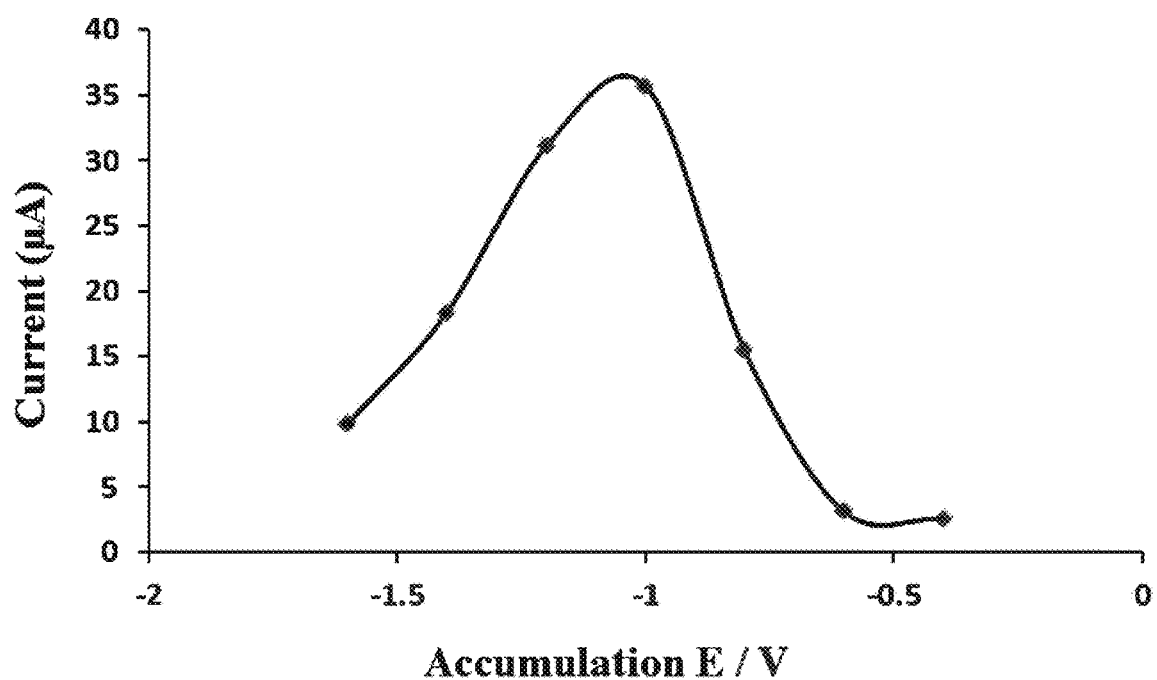

FIG. 64 is a plot of peak current versus deposition potential (accumulation potential) and illustrates the effect of varying deposition potential (−1.6 V to −0.4 V) of 500 ppb Pb(II) in 0.1 M phosphate buffer (pH=4) at a 2 wt % La-MOR-15 zeolite modified carbon paste composite B electrode with the graphite:zeolite:paraffin ratio of 65:5:30 at an accumulation time of 120 seconds, a potential step of 5 mV, an amplitude of 100 mV, and a frequency of 60 Hz.

Figure 65:
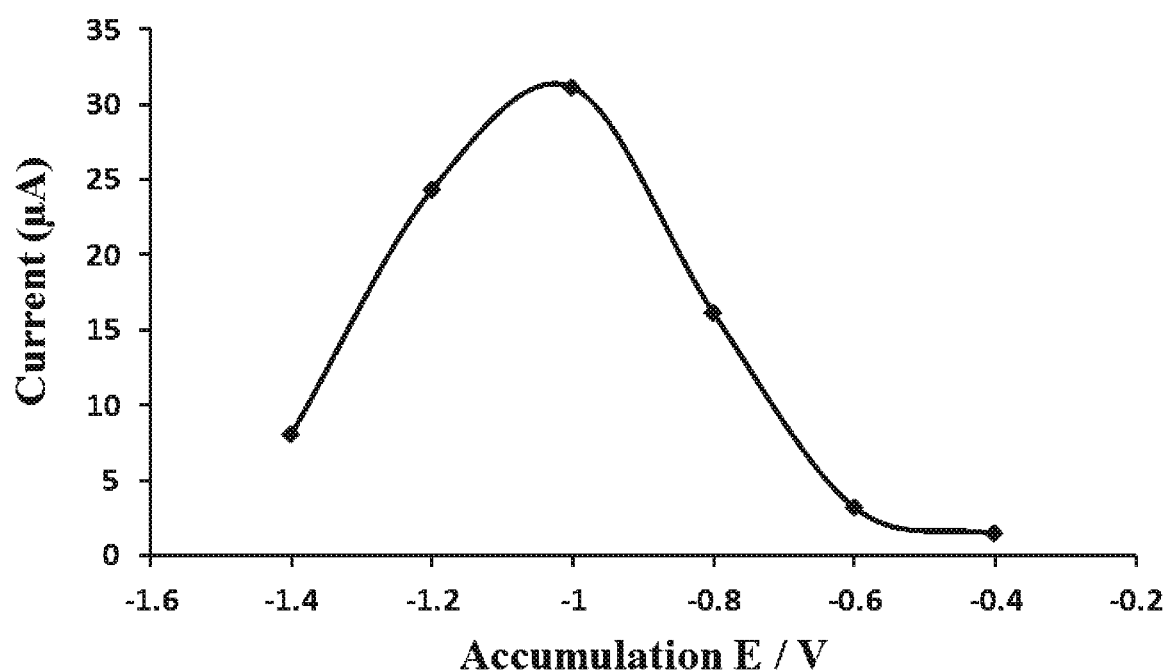

FIG. 65 is a plot of peak current versus deposition potential (accumulation potential) and illustrates the effect of varying deposition potential (−1.4 V to −0.4 V) of 500 ppb Pb(II) in 0.1 M phosphate buffer (pH=4) at a 10 wt % Ce-MOR-15 zeolite modified carbon paste composite G electrode with the graphite:zeolite:paraffin ratio of 65:5:30 at an accumulation time of 120 seconds, a potential step of 5 mV, an amplitude of 200 mV, and a frequency of 40 Hz.

Figure 66:
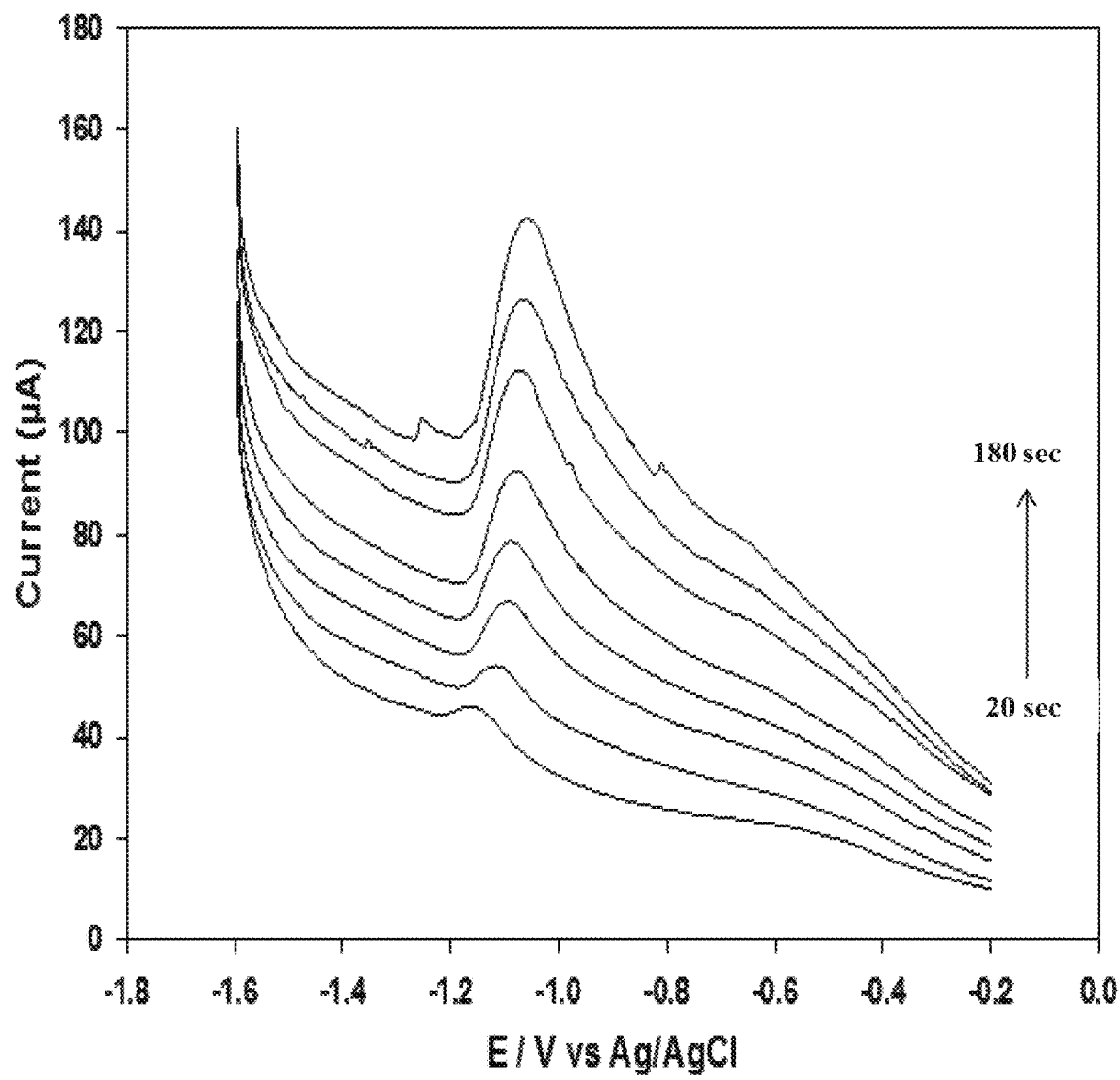

FIG. 66 illustrates the effect of varying deposition (accumulation) time (20-180 seconds) on the SWASV voltammograms of 500 ppb Pb(II) in 0.1 M phosphate buffer (pH=4) at a 2 wt % La-MOR-15 zeolite modified carbon paste composite B electrode with the graphite:zeolite:paraffin ratio of 65:5:30 at a deposition potential of −1.2 V, a potential step of 5 mV, an amplitude of 100 mV, and a frequency of 60 Hz.

Figure 67:
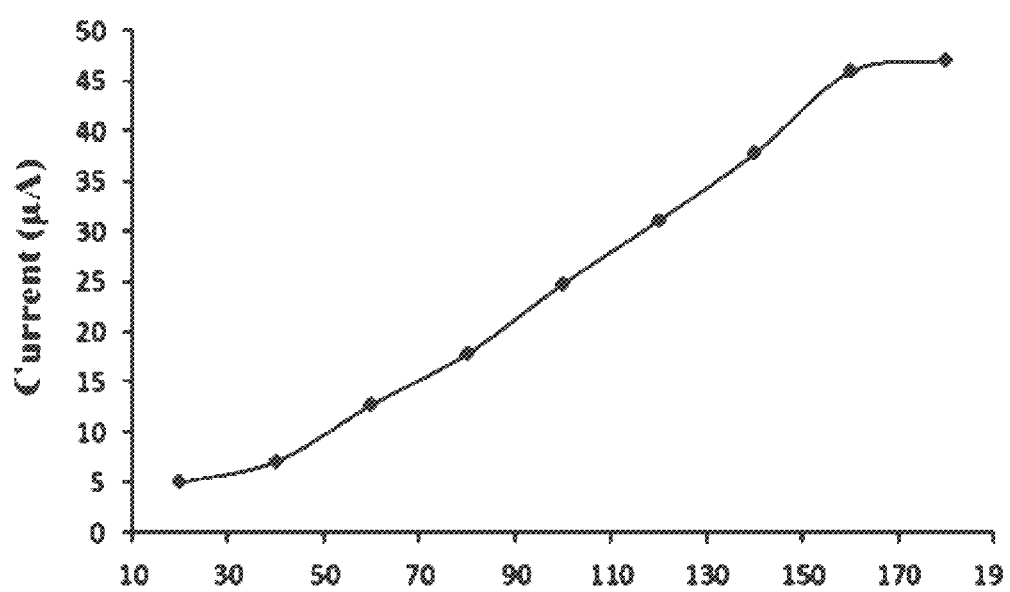

FIG. 67 is a plot of the current for a 2 wt % La-MOR-15 zeolite modified carbon paste composite B electrode with the graphite:zeolite:paraffin ratio of 65:5:30 versus deposition time (accumulation time).

Figure 68:
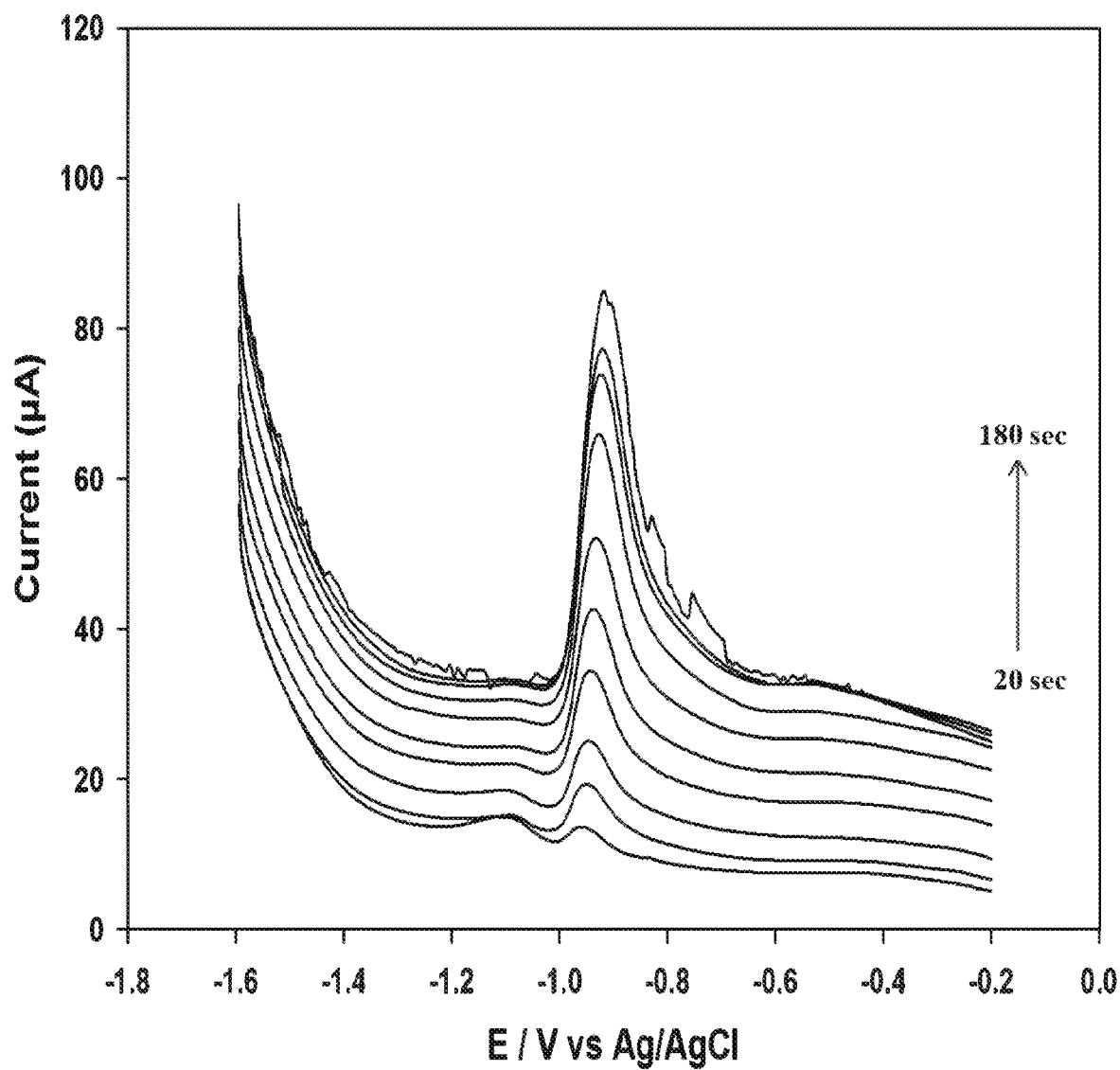

FIG. 68 illustrates the effect of varying deposition (accumulation) time (20-180 seconds) on the SWASV voltammograms of 500 ppb Pb(II) in 0.1 M phosphate buffer (pH=4) at a 10 wt % Ce-MOR-15 zeolite modified carbon paste composite G electrode with the graphite:zeolite:paraffin ratio of 65:5:30 at a deposition potential of −1.0 V, a potential step of 5 mV, an amplitude of 200 mV, and a frequency of 40 Hz.

Figure 69:
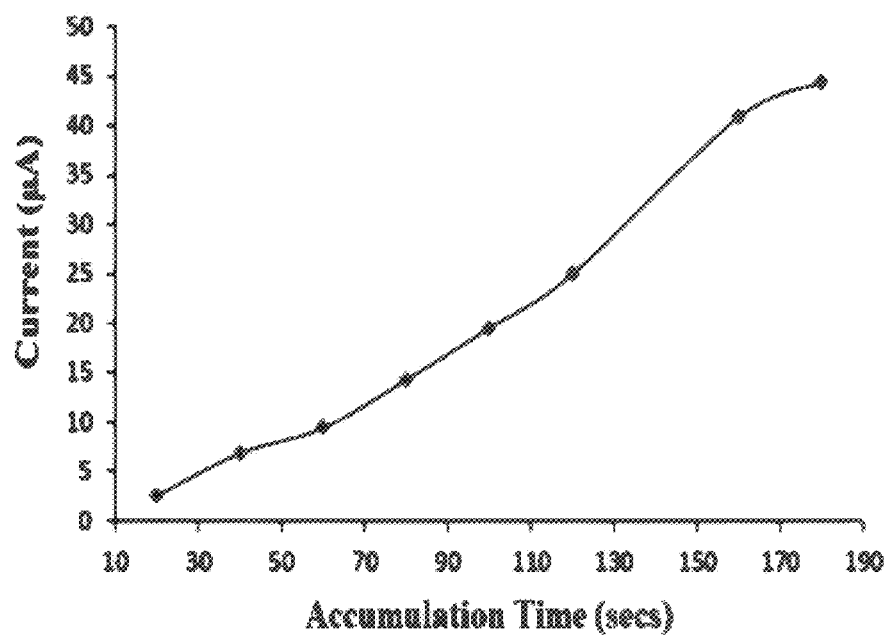

FIG. 69 is a plot of the current for a 10 wt % Ce-MOR-15 zeolite modified carbon paste composite G electrode with the graphite:zeolite:paraffin ratio of 65:5:30 versus deposition time (accumulation time).

Figure 70:
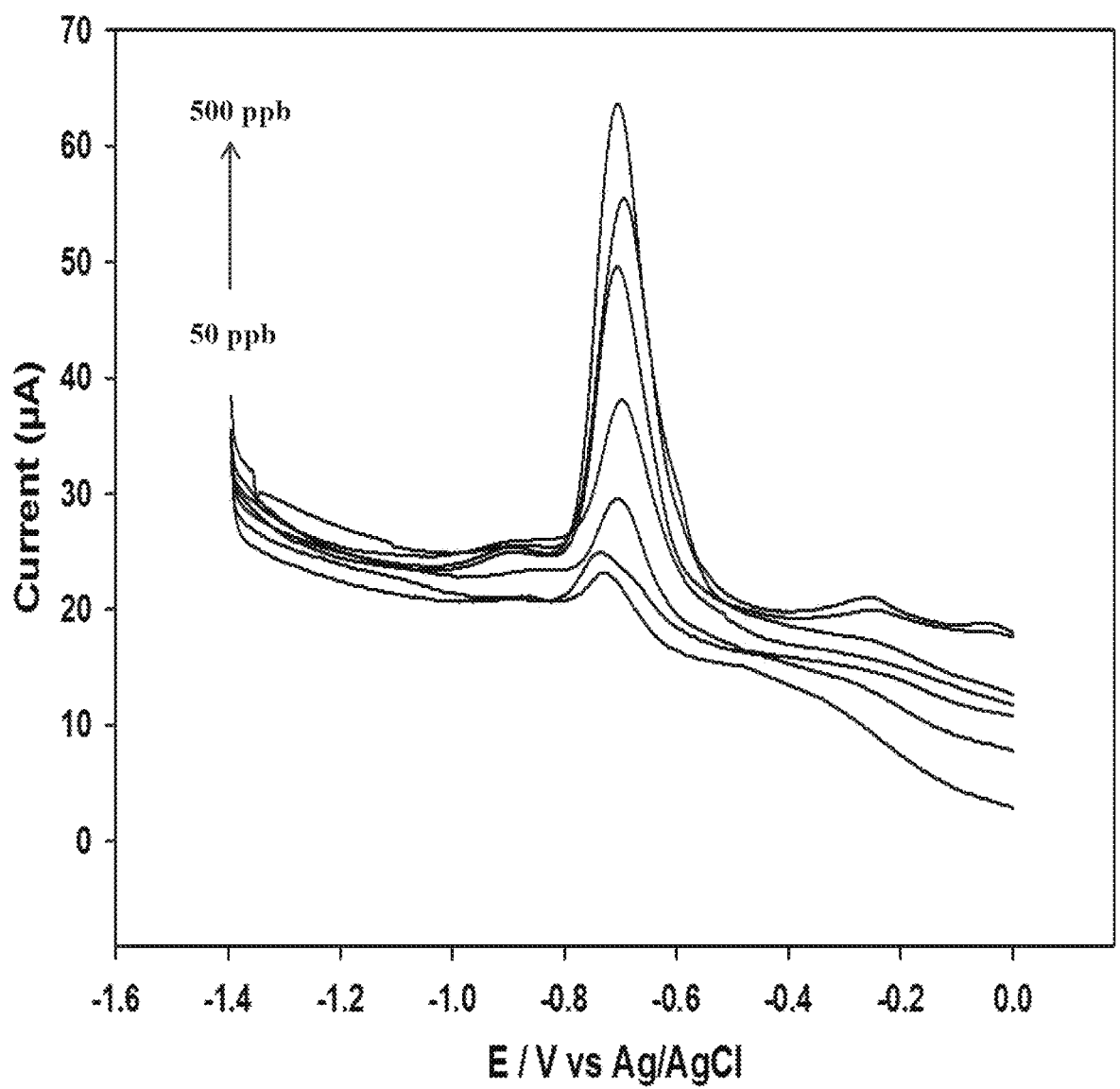

FIG. 70 illustrates the effect of varying Pb(II) concentration (50-500 ppb) on the square wave anodic stripping voltammetry (SWASV) voltammograms in 0.1 M phosphate buffer (pH=4) at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, an amplitude of 100 mV, and a frequency of 60 Hz.

Figure 71:
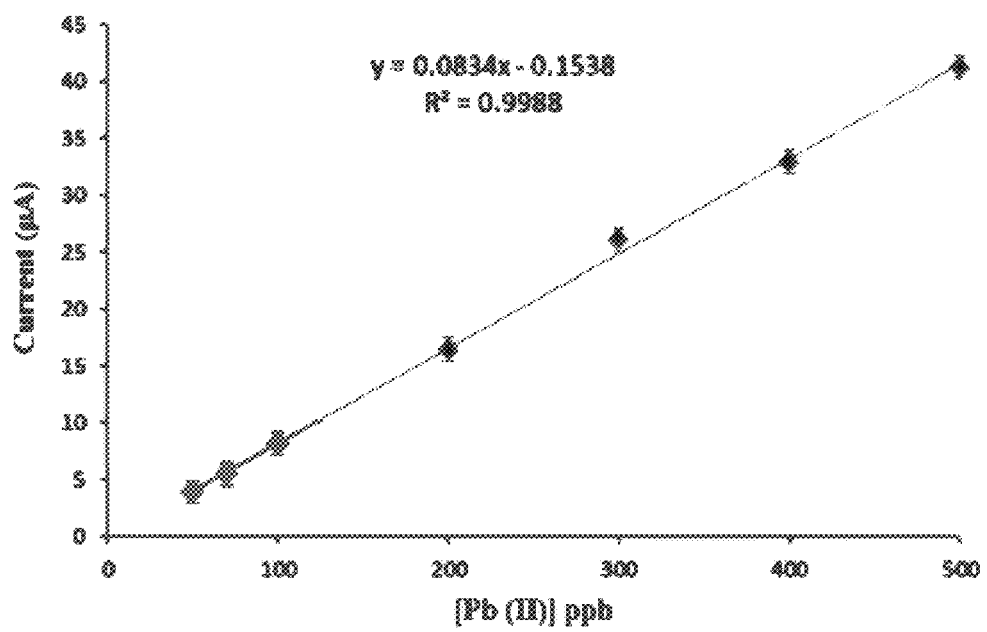

FIG. 71 is a calibration plot for a 2 wt % La-MOR-15 zeolite modified carbon paste composite B electrode with the graphite:zeolite:paraffin ratio of 65:5:30 of Pb(II) concentrations from 50-500 ppb.

Figure 72:
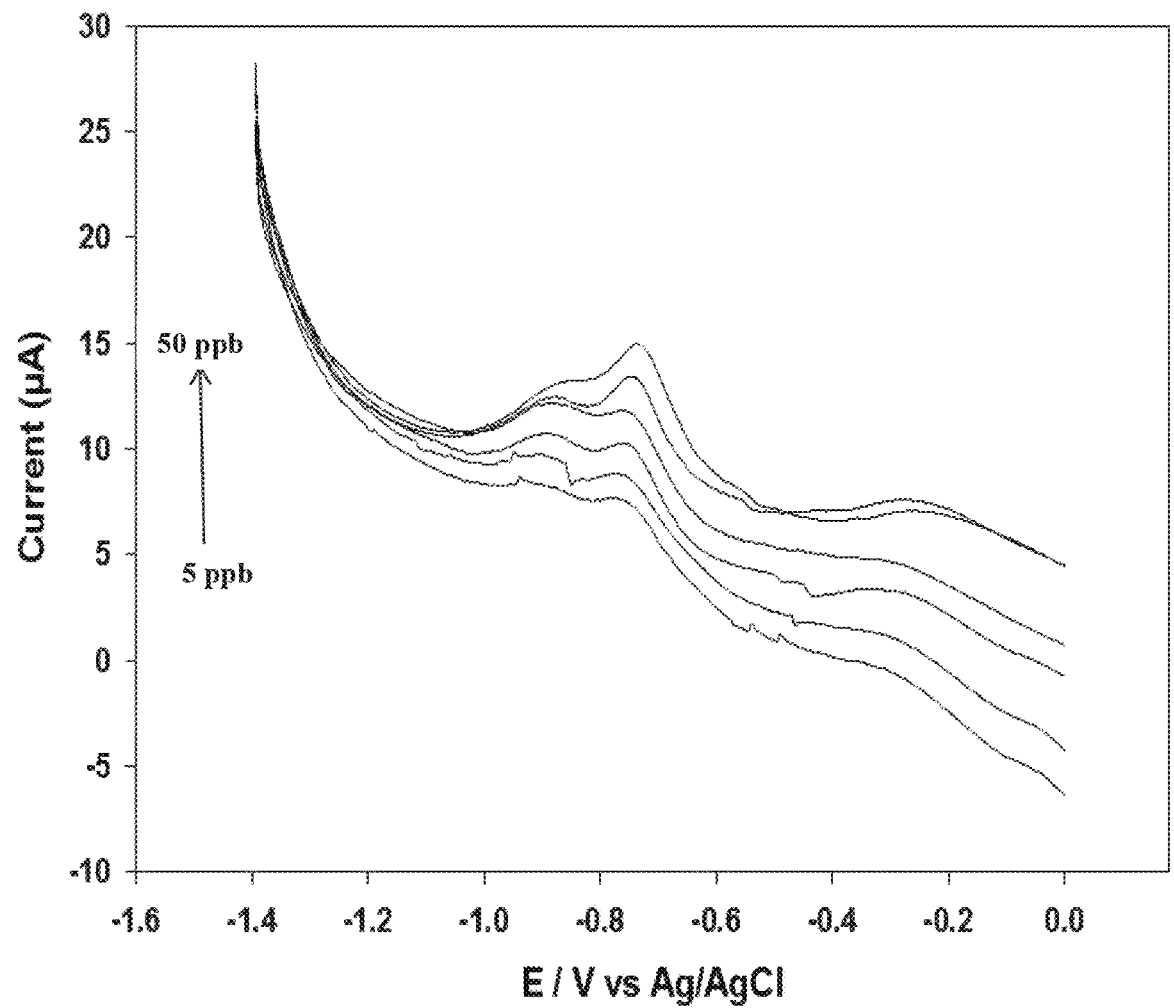

FIG. 72 illustrates the effect of varying Pb(II) concentration (5-50 ppb) on the square wave anodic stripping voltammetry (SWASV) voltammograms in 0.1 M phosphate buffer (pH=4) at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, an amplitude of 100 mV, and a frequency of 60 Hz.

Figure 73:
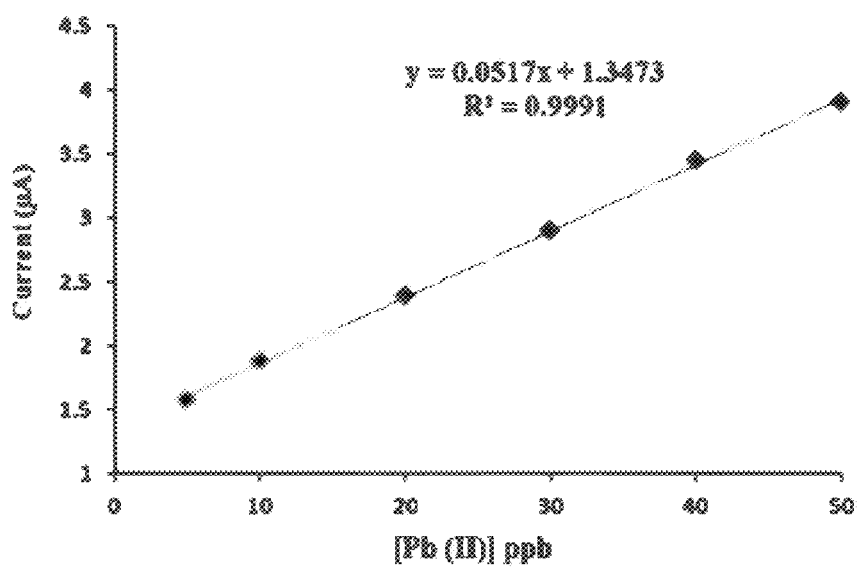

FIG. 73 is a calibration plot for a 2 wt % La-MOR-15 zeolite modified carbon paste composite B electrode with the graphite:zeolite:paraffin ratio of 65:5:30 of Pb(II) concentrations from 5-50 ppb.

Figure 74:
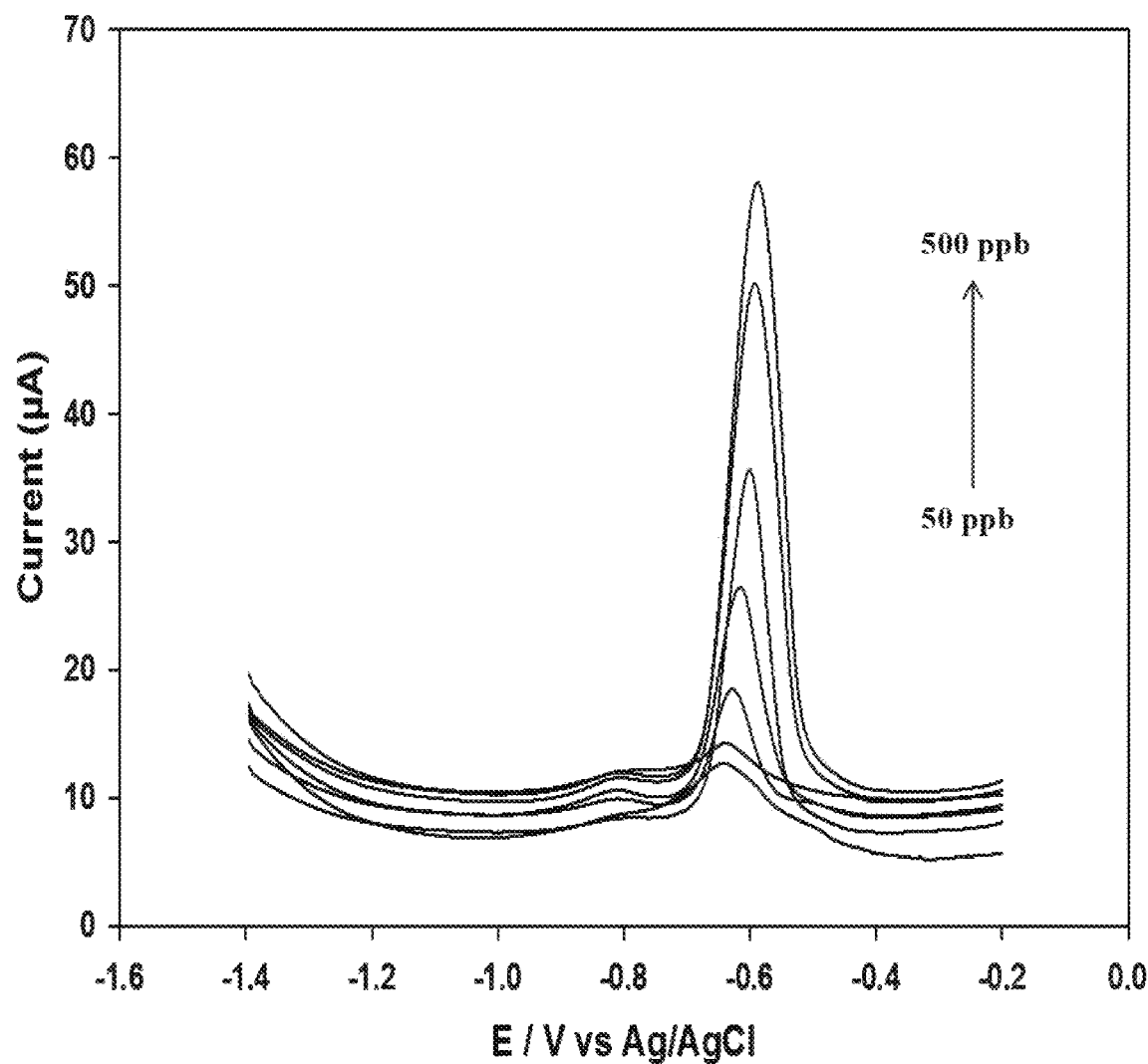

FIG. 74 illustrates the effect of varying Pb(II) concentration (50-500 ppb) on the square wave anodic stripping voltammetry (SWASV) voltammograms in 0.1 M phosphate buffer (pH=4) at a 10 wt % Ce-MOR-15 zeolite modified carbon paste composite G electrode with the graphite:zeolite:paraffin ratio of 65:5:30 at a deposition time of 120 seconds, a deposition potential of −1.2 V, a potential step of 5 mV, an amplitude of 200 mV, and a frequency of 40 Hz.

Figure 75:
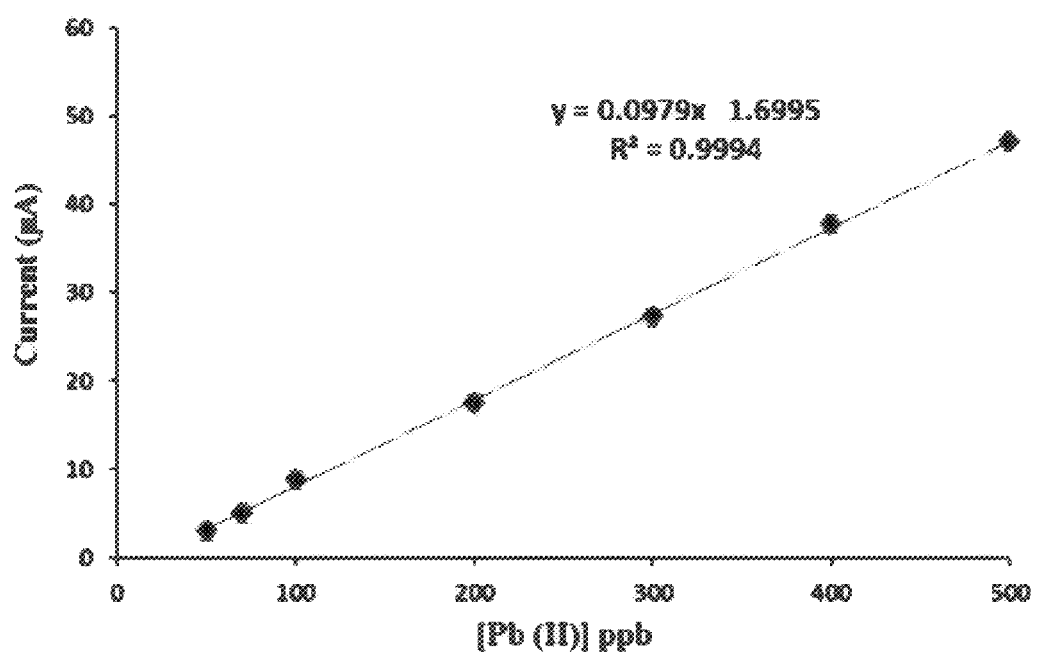

FIG. 75 is a calibration plot for a 10 wt % Ce-MOR-15 zeolite modified carbon paste composite G electrode with the graphite:zeolite:paraffin ratio of 65:5:30 of Pb(II) concentrations from 50-500 ppb.

Figure 76:
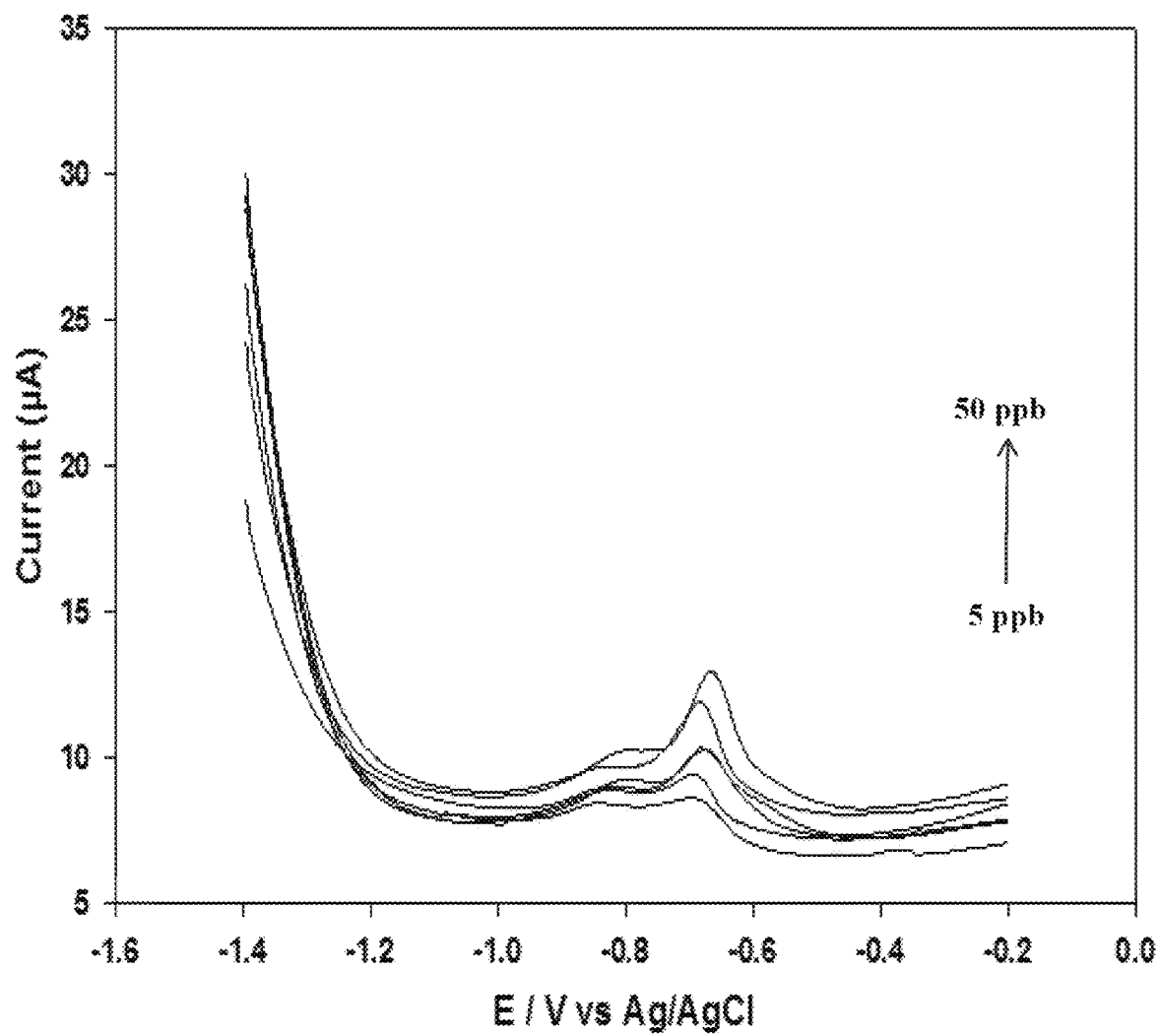

FIG. 76 illustrates the effect of varying Pb(II) concentration (5-50 ppb) on the square wave anodic stripping voltammetry (SWASV) voltammograms in 0.1 M phosphate buffer (pH=4) at a 10 wt % Ce-MOR-15 zeolite modified carbon paste composite G electrode with the graphite:zeolite:paraffin ratio of 65:5:30 at a deposition time of 120 seconds, a deposition potential of −1.2 V, a potential step of 5 mV, an amplitude of 200 mV, and a frequency of 40 Hz.

Figure 77:
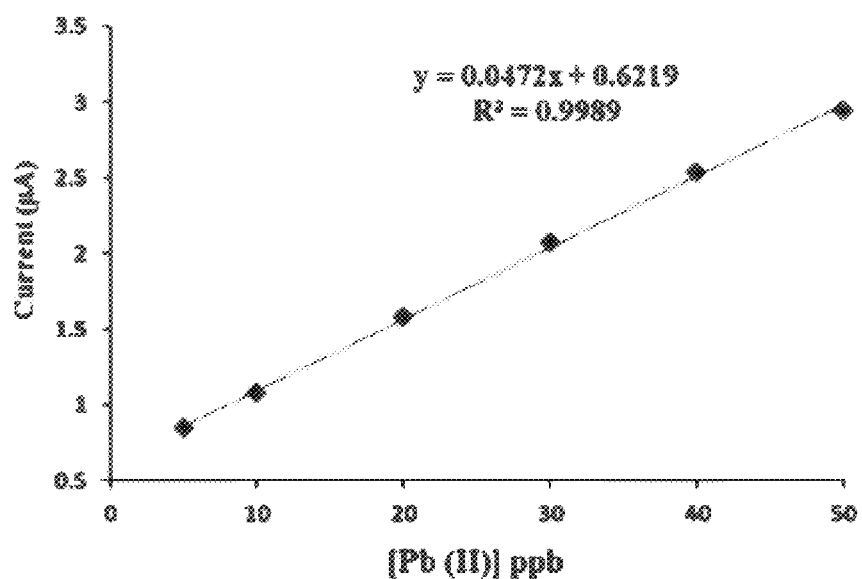

FIG. 77 is a calibration plot for a 10 wt % Ce-MOR-15 zeolite modified carbon paste composite G electrode with the graphite:zeolite:paraffin ratio of 65:5:30 of Pb(II) concentrations from 5-50 ppb.

Figure 78:
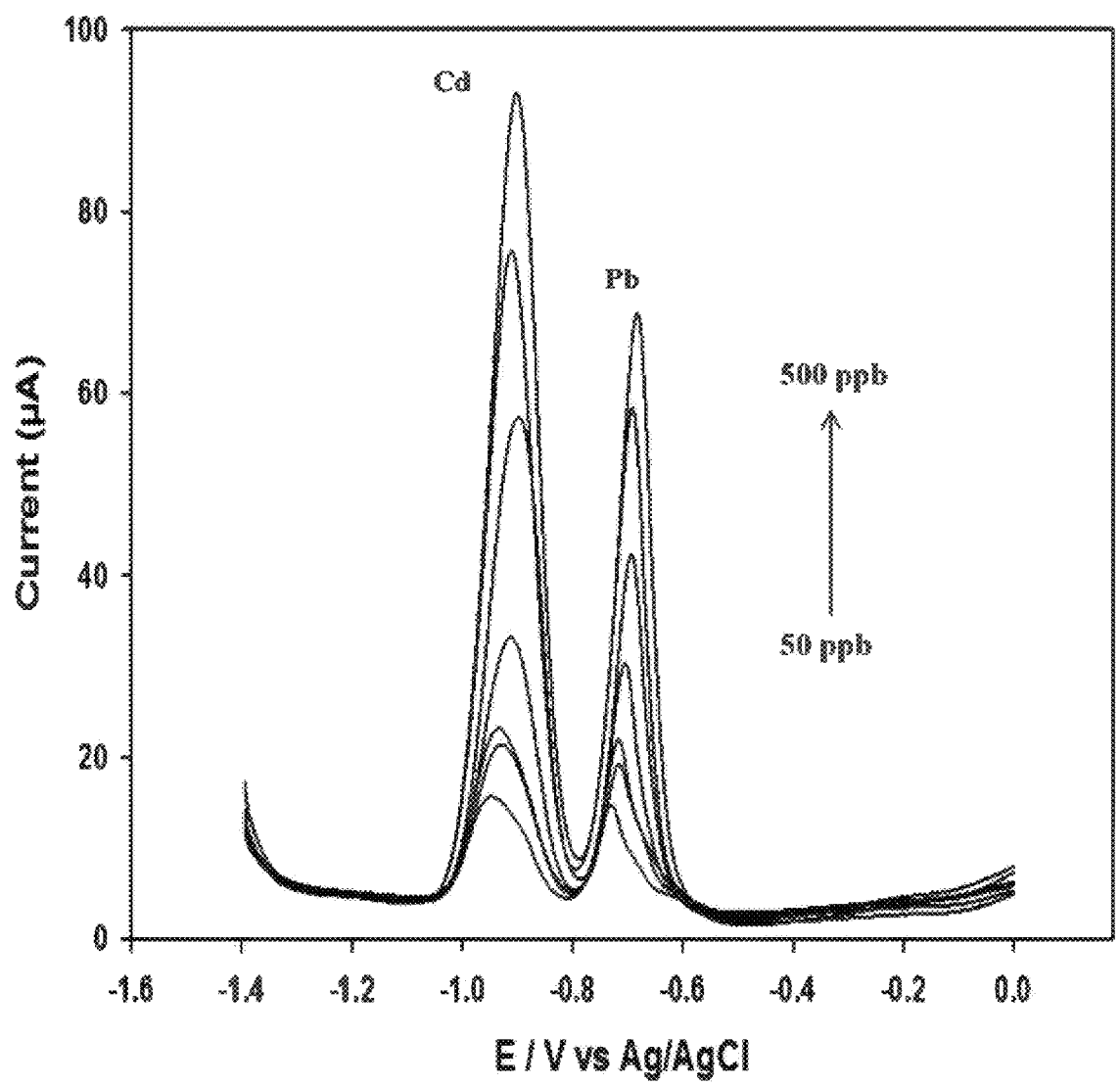

FIG. 78 illustrates the effect of varying Cd(II) concentration (50-500 ppb) and Pb(II) concentration (50-500 ppb) on the square wave anodic stripping voltammetry (SWASV) voltammograms in 0.1 M phosphate buffer (pH=4) at a 2 wt % La-MOR-15 zeolite modified carbon paste composite B electrode with the graphite:zeolite:paraffin ratio of 65:5:30 at a deposition time of 120 seconds, a deposition potential of −1.2 V, a potential step of 5 mV, an amplitude of 100 mV, and a frequency of 60 Hz.

Figure 79:
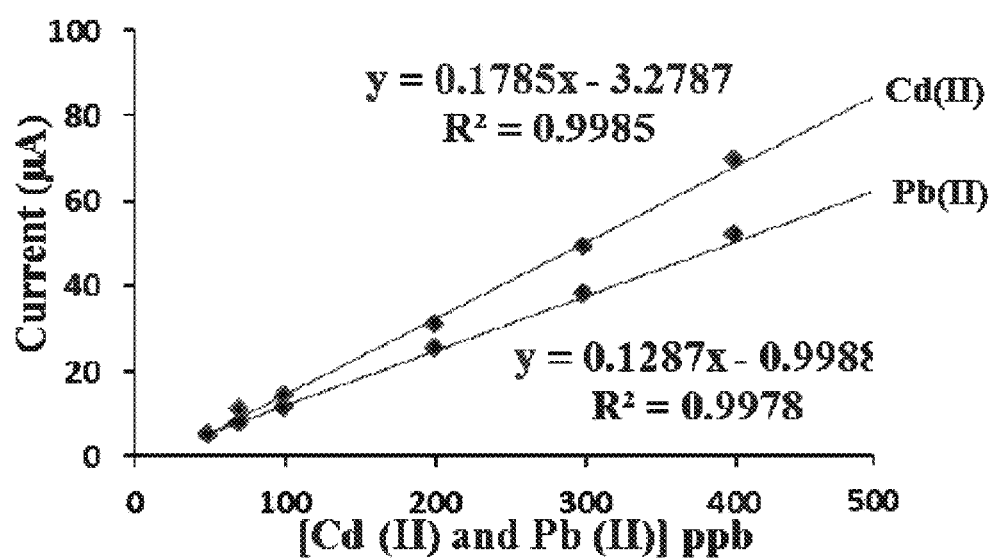

FIG. 79 is a calibration plot for a 2 wt % La-MOR-15 zeolite modified carbon paste composite B electrode with the graphite:zeolite:paraffin ratio of 65:5:30 of Cd(II) and Pb(II) concentrations from 50-500 ppb.

Figure 80:
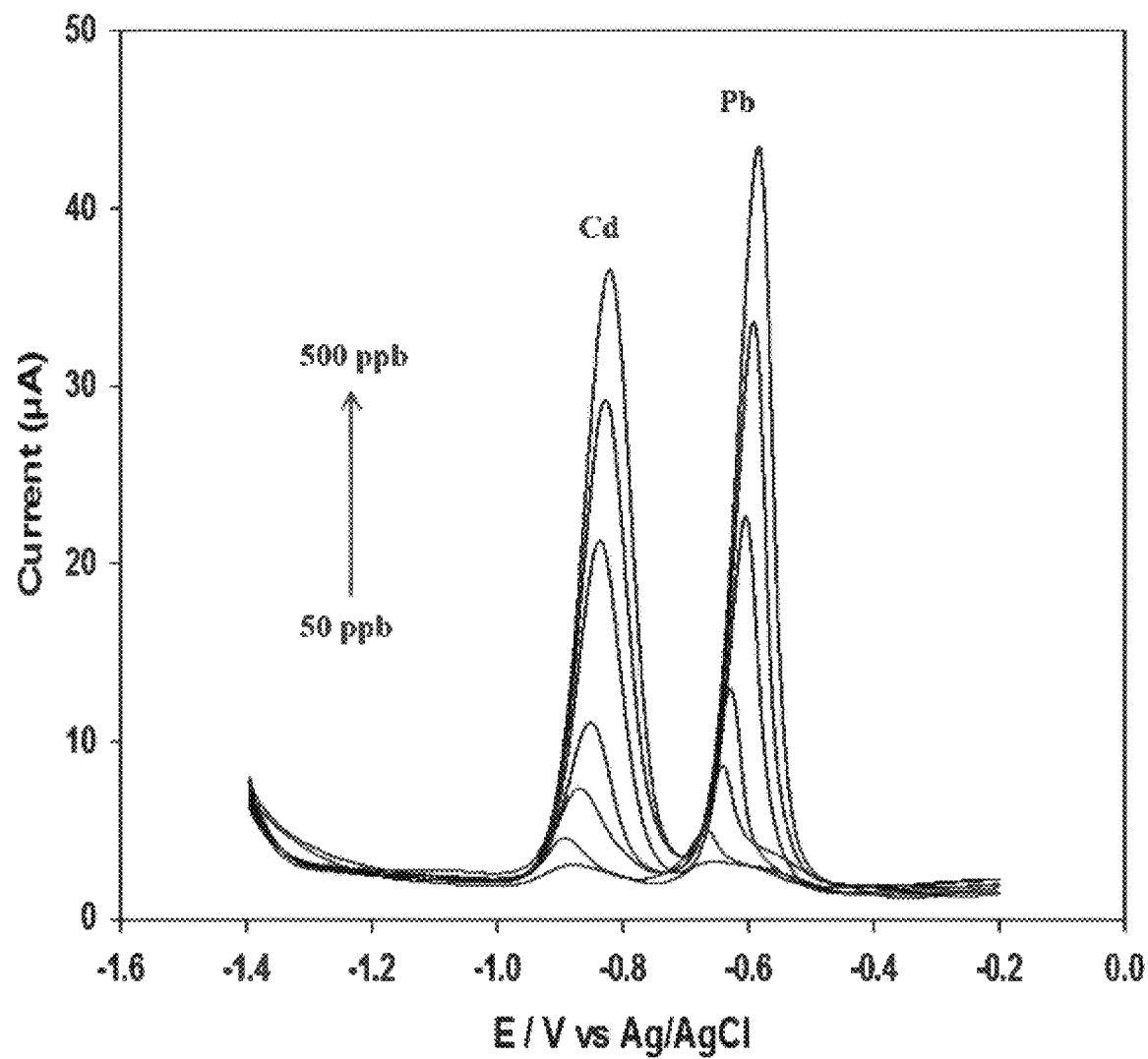

FIG. 80 illustrates the effect of varying Cd(II) concentration (50-500 ppb) and Pb(II) concentration (50-500 ppb) on the square wave anodic stripping voltammetry (SWASV) voltammograms in 0.1 M phosphate buffer (pH=4) at a 10 wt % Ce-MOR-15 zeolite modified carbon paste composite G electrode with the graphite:zeolite:paraffin ratio of 65:5:30 at a deposition time of 120 seconds, a deposition potential of −1.2 V, a potential step of 5 mV, an amplitude of 200 mV, and a frequency of 40 Hz.

Figure 81:
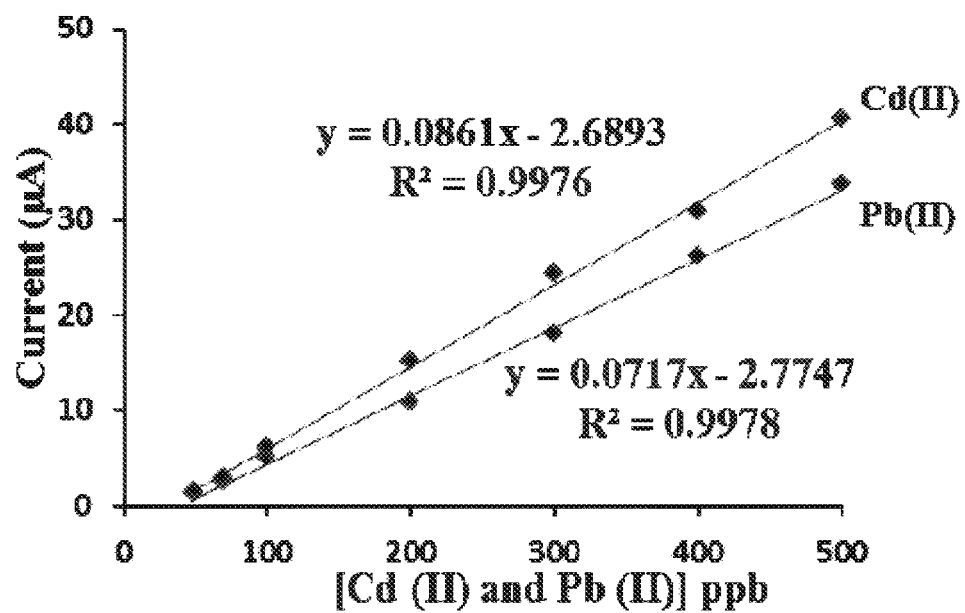

FIG. 81 is a calibration plot for a 10 wt % Ce-MOR-15 zeolite modified carbon paste composite G electrode with the graphite:zeolite:paraffin ratio of 65:5:30 of Cd(II) and Pb(II) concentrations from 50-500 ppb.

DETAILED DESCRIPTION OF THE EMBODIMENTS

Referring now to the drawings, wherein, like reference numerals designate identical or corresponding parts throughout the several views. Embodiments of the present disclosure will now be described more fully hereinafter with reference to the accompanying drawings, in which some, but not all of the embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more". The phrases "selected from the group consisting of", "chosen from", and the like include mixtures of the specified materials. Terms such as "contain(s)" and the like are open terms meaning "including at least" unless otherwise specifically noted.

According to a first aspect, the present disclosure relates to an electrode comprising: i) graphite powder, ii) paraffin oil, and iii) a zeolite impregnated with a rare earth metal.

As used herein, an electrode refers to an electrical conductor used to make contact with a nonmetallic part of a circuit (i.e. a semiconductor, an electrolyte, a vacuum or air), preferably an electrolyte. In certain embodiments, the term electrode may include the electroactive material of the electrode. In certain embodiments, the electrode of the present disclosure may be present in a holder or an electrochemical cell and the term electrode may refer to the full the electrode in the holder and/or the electrochemical cell. As used herein, an electrochemical cell refers to a device capable of either generating electrical energy from chemical reactions or facilitating chemical reactions through the introduction of electrical energy. The electrode in an electrochemical cell may be referred to as either an anode or a cathode. As used herein, an anode refers to the electrode at which electrons leave the cell and oxidation occurs, and a cathode refers to the electrode at which electrons enter the cell and reduction occurs. Each electrode may become either the anode or the cathode depending on the direction of current through the cell. In addition a bipolar electrode describes an electrode that functions as the anode of one cell and the cathode of another cell. Chemically modified electrodes are electrodes that have their surface chemically modified to change the electrode's physical, chemical, electrochemical, optical, electrical, and/or transport properties. These electrodes are used for advanced purposes in research and investigation.

As used herein, a chemically modified electrode (CME) is an electrical conductor (material that has the ability to transfer electricity) that has its surface or material modified for different electrochemical functions. At a modified electrode, an oxidation-reduction substance accomplishes electrocatalysis by transferring electrons from the electrode to a reactant, or a reaction substrate. Electrodes can be modified in a variety of ways including, but not limited to, adsorption (chemisorption), covalent bonding, polymer film coating, and composite formation. Composite formation refers to a method that has the chemical modifier mixed with an electrode matrix material (i.e. having a zeolite, the chemical modifier, mixed with carbon particles in a carbon paste electrode, the electrode matrix). Exemplary electrodes that can be chemically modified include, but are not limited to, carbon paste electrodes, glassy carbon paste electrodes, glassy carbon electrodes, pyrolytic carbon electrodes, and the like. Chemically modified electrodes have been employed for the analysis of a variety of organic and inorganic species.

In a preferred embodiment, the electrode of the present disclosure may be considered as a chemically modified electrode (CME), preferably a modified carbon paste electrode (CPE or MCPE), specifically a zeolite modified carbon paste electrode (ZMCPE). As used herein, a carbon paste electrode refers an electrode made from a mixture of conducting graphite powder and a pasting liquid (i.e. paraffin oil). These electrodes are simple to construct and offer an easily renewable surface for electron exchange. Carbon paste electrodes belong to a special group of heterogeneous carbon electrodes. These electrodes are widely used mainly for voltammetric measurements; however, carbon paste based sensors are also applicable in coulometry (both amperometry and potentiometry). In general, carbon paste electrodes are advantageous because carbon pastes are easily obtainable at minimal costs and are especially suitable for preparing an electrode material modified with admixtures (i.e. zeolites) of other compounds thus giving the electrode certain predetermined properties. Electrodes prepared in this way can serve as highly selective sensors for both inorganic and organic electrochemistry. Carbon paste electrodes, glassy carbon paste electrodes, glassy carbon electrodes (GCE), pyrolytic graphite electrodes (PyGE), etc. when modified are termed as chemically modified electrodes. Chemically modified electrodes have been employed for the analysis of inorganic and organic species. In a preferred embodiment the electrode is a rare earth metal impregnated zeolite modified carbon paste electrode representing a homogeneous mixture of the graphite powder, the paraffin oil, and the zeolite impregnated with a rare earth metal.

In a preferred embodiment, the electrode of the present disclosure comprises graphite powder as a conductive carbon. Graphite is essentially made up of hundreds, preferably thousands or tens to hundreds of thousands of layers of graphene. As used herein, graphite (or plumbago) refers to a crystalline form of carbon, a semimetal, a native element mineral, and one of the allotropes of carbon. Graphite is the most stable form of carbon under standard conditions. Graphite may be considered the highest grade of coal, just above anthracite and alternatively called meta-anthracite. Graphite has a layered, planar structure. In each layer the carbon atoms arranged in a honeycomb lattice with separation of 0.14-0.15 nm, preferably 0.14-0.145 nm or about 0.142 nm and a distance between planes of 0.3-0.35 nm, preferably 0.32-0.345 nm, preferably 0.33-0.34 nm, or about 0.335 nm. Atoms in the plane are bonded covalently, with only three of the four potential bonding sites satisfied. The fourth electron is free to migrate in the plane, making graphite electrically conductive; however, it does not conduct in a direction at right angles to the plane. Bonding between the layers is via weak van der Waals bonds, which allows layers of graphite to be easily separated, or to slide past each other. In one embodiment, the graphite material of the electrode described herein comprises 10-500000 layers of graphene, preferably 100-400000 layers of graphene, preferably 500-300000 layers of graphene, preferably 1000-250000 layers of graphene, preferably 5000-200000 layers of graphene, preferably 10000-150000 layers of graphene, preferably 25000-125000 layers of graphene, preferably 50000-100000 layers of graphene.

The two known forms of graphite are alpha (α, hexagonal) and beta (β, rhombohedral). The two forms have very similar physical properties, except the graphene layers stack slightly differently. The hexagonal graphite may be either flat or buckled. The alpha form can be converted to the beta form through mechanical treatment and the beta form reverts to the alpha form when heated to sufficiently high temperatures (~1300° C.). In terms of the present disclosure, the graphite material of the electrode described herein may be alpha, beta, or mixtures thereof.

There are three principal types of natural graphite, each occurring in different types of ore deposit. Crystalline flake graphite (or flake graphite) occurs as isolated, flat, plate-like particles with hexagonal edges if unbroken and when broken the edges can be irregular or angular. Amorphous graphite refers to very fine flake graphite. Lump graphite (or vein graphite) occurs in fissure veins or fractures and appears as massive platy intergrowths of fibrous or acicular crystalline aggregates. Highly ordered or oriented pyrolytic graphite (HOPG) refers to graphite with an angular spread between the graphite sheets of less than 1°. Graphite fiber is also sometimes used to refer to carbon/fiber and/or carbon fiber reinforced polymer. In terms of the present disclosure, the graphite material employed may be natural graphite, synthetic graphite, crystalline flake graphite, amorphous graphite, highly oriented pyrolytic graphite, lump graphite, graphite fiber, graphite nanofiber, chemically modified graphite, expanded graphite, intercalated graphite, and mixtures thereof, preferably graphite in the form of flakes, rods, or powder, most preferably commercially available graphite powder.

Exemplary commercially available graphite powders include, but are not limited to CR (Czech Republic), RW (Germany, Austria), BDH (Scandinavia and United Kingdom), SMMC (China), Acheson, UCP, GP, and SP (United States). In a preferred embodiment, the graphite powder has an average particle (grain) size in the ranges of micrometers or tens of micrometers, preferably 10-90 µm, preferably 10-50 µm, preferably 15-40 µm, preferably 20-30 µm and a relatively uniform particle size distribution (i.e. 5-20 µm). In some embodiments the graphite powder has an average particle (grain) size in the range of 20-100 nm, preferably 30-80 nm. In certain embodiments, the graphite powder is substantially free of impurities, such as oxygen, and possesses low adsorption capabilities, meaning the graphite powder pure graphite content is greater than 80% by weight graphite relative to the total weight of the graphite powder, preferably greater than 85% by weight, preferably greater than 90% by weight, preferably greater than 95% by weight, preferably greater than 96% by weight, preferably greater than 97% by weight, preferably greater than 98% by weight, preferably greater than 99% by weight, preferably greater than 99.5% by weight, preferably greater than 99.9% by weight, preferably greater than 99.99% by weight, preferably greater than 99.995% by weight pure graphite content relative to the total weight of the graphite powder.

In a preferred embodiment, the electrode of the present disclosure has a weight percentage of the graphite powder in the range of 45-75% relative to the total weight of the electrode, preferably 50-70% by weight, preferably 55-69% by weight, preferably 60-68% by weight, preferably 62-66% by weight, or about 65% by weight relative to the total weight of the electrode.

It is equally envisaged that the electrode of the present disclosure may further comprise or may be adapted to comprise additional carbonaceous materials as conductive carbon. Exemplary suitable carbonaceous materials include, but are not limited to, acetylene black (AB), obtained by controlled combustion of acetylene in inert atmosphere or chemical decomposition, carbon black, an amorphous material obtainable by the incomplete combustion of heavy petroleum fractions, colloidal graphite, hexagonal carbon with extremely fine flakes and enhanced conductivity, both natural and synthetic forms of diamond applied as fine powders, soot, activated charcoal, coal ("black coal"), lignite ("brown coal"), glassy carbon (GC), fullerene (C-60), carbon nanomaterials (carbon nanotubes, CNTs, carbon nanohorns, carbon nanoparticles, carbon nanofibers), porous carbon foam, porous carbon microspheres, template carbon, ordered mesoporous carbon (OMC) and the like.

Mechanical connection of the individual carbon particles into a uniform mass is not the only role of binders. Each pasting liquid, including highly chemically inert substances, codetermines principal physicochemical and electrochemical properties of the electrode. Typical parameters of a suitable pasting liquid or binder include, but are not limited to, chemical inertness and electroinactivity, low volatility, minimal solubility in water, and controlled miscibility with organic solvents.

In a preferred embodiment, the electrode of the present disclosure comprises paraffin (mineral) oils as a pasting liquid or binder. As used herein, mineral oil or paraffin oil refers to any of various colorless, odorless light mixtures of higher alkanes from a mineral source, particularly a distillate of petroleum. Most often, mineral oil is a liquid by-product of refining crude oil to make gasoline and other petroleum products. This type of mineral oil is a transparent, colorless oil composed mainly of alkanes and cycloalkanes related to petroleum jelly. The mineral oil or paraffin oil of the present disclosure may be light, medium or heavy grade in terms of density and viscosity. The mineral oil or paraffin oil preferably has a density of 0.75-0.92 g/mL, preferably 0.80-0.90 g/mL, preferably 0.81-0.89 g/mL, preferably 0.83-0.86 g/mL and a viscosity of 5-15 $mm^2/s$, preferably 7-13 $mm^2/s$, preferably 8.5-11 $mm^2/s$. Three basic classes of mineral oils exist: i) alkanes and alkane oils based on light n-alkanes, ii) naphthenic oils, based on cycloalkanes, and iii) aromatic oils, based on aromatic hydrocarbons (distinct from essential oils). In terms of the present disclosure, the mineral oil or paraffin oil may be an alkane oil, a naphthenic oil, an aromatic oil, and mixtures thereof. Typical paraffin oil is formed by a mixture of liquid aliphatic hydrocarbons and is often marketed under a tradename. Exemplary suitable products of this kind include, but are not limited to Nujol and Uvasol.

In a preferred embodiment, the electrode of the present disclosure has a weight percentage of the paraffin oil in the range of 20-40% relative to the total weight of the electrode, preferably 22-38% by weight, preferably 24-36% by weight, preferably 26-34% by weight, preferably 28-32% by weight, or about 30% by weight relative to the total weight of the electrode. In a preferred embodiment, the ratio of graphite to paraffin oil is in the range of 1.0 g graphite to 0.1-5.0 mL paraffin oil, preferably 1.0 g graphite to 0.2-2.0 mL paraffin oil, preferably 1.0 g graphite to 0.4-1.0 mL paraffin oil.

It is equally envisaged that the electrode of the present disclosure may further comprise or may be adapted to comprise additional pasting liquids or binders. Exemplary suitable pasting liquids or binders include, but are not limited to, aliphatic and aromatic hydrocarbons ($C_8$-$C_{20}$, $C_{10}$-$C_{14}$ such as for example benzene, naphthalene, phenanthrene, and hexadecane), silicone oils and greases (polymerized siloxanes optionally with organic side chains, halogenated hydrocarbons and similar derivatives (bromoform, carbon tetrachloride, α-bromonaphthalene, p-dichlorobenzene, and trans-1,2-dibromocyclohexane), 1,2,3-trichloropropane (TCP), dioctyl phthalate (DOP), di-iso-nonyl phthalate (DINP), 1-(2-nitrophenoxy)octane (NPOE), diphenyl ether, glycerol, castor oil, vaseline oil, polycationic electrolytes, room temperature ionic liquids (RTILs) and the like.

In a preferred embodiment, the electrode of the present disclosure is a chemically modified carbon paste electrode, preferably a zeolite modified carbon paste electrode, comprising a zeolite as an electroactive material, preferably a zeolite impregnated with a rare earth metal. As used herein, a zeolite refers to a microporous aluminosilicate mineral. Many zeolites occur naturally but are also produced industrially on a large scale. Zeolites are crystalline solid structures made of silicon, aluminum and oxygen that form a framework with cavities and channels inside where cations, water, and/or small molecules may reside. Zeolites have a porous structure that can accommodate a wide variety of cations, such as $Na^+$, $K^+$, $Ca^{2+}$, $Mg^{2+}$ and others. These positive ions are rather loosely held and can readily be exchanged for others in a contact solution. Alternatively, zeolites are the aluminosilicate members of the family of microporous solids known as "molecular sieves". Several varied unique zeolite frameworks have been discovered, at present there are nearly 200 unique zeolite frameworks identified and over 40 naturally occurring zeolite frameworks are known. Zeolites are crystalline materials that afford molecular sized frames and pores, the major building units of zeolites are $[SiO4]^{4-}$ and $[AlO4]^{5-}$ tetrahedra. Zeolites are crystalline aluminosilicates with open 3D framework structures built of $SiO_4$ and $AlO_4$ tetrahedra linked to each other by sharing all the oxygen atoms to form regular intra-crystalline cavities and channels of molecular dimensions. In a defining feature zeolite frameworks are made up of 4-coordinated atoms forming tetrahedra. These tetrahedra are linked together by their corners leading to a wide variety of structures. These units can link in several ways, resulting in arrays producing three-dimensional anionic networks. The extra negative charge on [AlO4]5– tetrahedra is counter balanced by a cation, maintaining the overall neutrality of the zeolite. The framework structure may contain linked cages, cavities, and/or channels which are big enough for small molecules to enter and/or occupy. The system of large voids explains the low specific density of these compounds.

In terms of the present disclosure a variety of zeolite mineral species may be suitable. The zeolite structural group (Nickel-Strunz classification) includes, but is not limited to, 09.GA zeolites, 09.GB zeolites, 09.GC zeolites, 09.GD zeolites, 09.GE zeolites and mixtures thereof. The 09.GA zeolites with $T_5O_{10}$ units (T=combined Si and Al) are known as the fibrous zeolites and include, but are not limited to, the natrolite framework (NAT; gonnardite, natrolite, mesolite, paranatrolite, scolecite, tetranatrolite), the edingtonite framework (EDI; edingtonite, kalborsite), the thomsonite framework (THO; thomsonite series), and mixtures thereof. The 09.GB zeolites with chains of single connected 4-membered rings include, but are not limited to, the analcime framework (ANA; analcime, leucite, pollucite, wairakite), laumontite (LAU), yugawaralite (YUG), goosecreekite (GOO), montesommaite (MON), and mixtures thereof. The 09.GC zeolites with chains of doubly connected 4-membered rings include, but are not limited to, the phillipsite framework (PHI; harmotome, phillipsite series), the gismondine framework (GIS; amicite gismondine, garronite, gobbinsite), boggsite (BOG), merlinoite (MER), the mazzite series (MAZ), the paulingite series (PAU), perlialite (Linde type L framework, zeolite L, LTL), and mixtures thereof. The 09.GD zeolites with chains of 6-membered rings are known as tabular zeolites and include, but are not limited to, the chabazite framework (CHA; chabazite series, herschelite, willhendersonite, SSZ-13), the faujasite framework (FAU; faujasite series, Linde type X, zeolite X, X zeolites, Linde type Y, zeolite Y, Y zeolites), the mordenite framework (MOR; maricopaite, mordenite), the offretite-wenkite subgroup 09.GD.25 such as offretite (OFF) and wenkite (WEN), belilbergite (TMA-E, Aiello and Barrer, framework type EAB), bikitaite (BIK), the erionite series (ERI), ferrierite (FER), gmelinite (GME), the levyne series (LEV), the dachiardite series (DAC), epistilbite (EPI), and mixtures thereof. The 09.GE zeolites with chains of $T_{10}O_{20}$ tetrahedra (T=combined Si and Al) include, but are not limited to, the heulandite framework (HEU; clinoptilolite, heulandite series), the stilbite framework (STI; barrerite, stellerite, stilbite series); brewsterite framework (BRE; brewsterite series), and mixtures thereof. Other acceptable structural group frameworks may include, but are not limited to, cowlesite, pentasil (also known as ZSM-5, framework type MFI), tschernichite (beta polymorph A, disordered framework, BEA), Linde type A framework (zeolite A, LTA), and the like. In terms of the present disclosure, the zeolite and/or the zeolite impregnated with a rare earth metal may have a 09.GA, 09.Gb, 09.GC, 09.GD, or 09.GE structural group framework, preferably a 09.GD structural group framework.

Often zeolites may be classified into groups according to the Si/Al ratio in their frameworks: i) "low silica" or aluminum rich zeolites A and X (silica to alumina molar ratio Si/Al ~1), ii) "intermediate silica" zeolites such as for example zeolite Y, mordenite, zeolite L, and natural zeolites (silica to alumina molar ratio Si/Al 2 to 5), and iii) "high silica" zeolites such as zeolite beta and ZSM-5 (silica to alumina molar ratio Si/Al≥10).

The "low silica" zeolites represent a fortunate balance of composition, pore volume, and channel structure. These zeolites are nearly "saturated" in aluminum in the framework composition with a molar ratio of Si/Al ~1, which is considered the highest aluminum content possible in tetrahedral aluminosilicate frameworks. Consequently, they contain the maximum number of cation exchange sites balancing the framework aluminum, and thus the highest cation contents and exchange capacities. These compositional characteristics provide the most highly heterogeneous surface known among porous materials, due to exposed cationic charges nested in an aluminosilicate framework which results in high field gradients. Their surfaces are highly selective for water, polar, and polarizable molecules. The "intermediate silica" zeolites represent superior stability characteristics reflecting higher Si/Al molar ratios (1.5-5, preferably 2.5-4, preferably 3-3.5) that improve both thermal and acid stability as aluminum positions in the zeolite frameworks pose a site of instability to attack by acid and water vapor. In addition to improvement in stability the difference in composition and structures provided additional catalysis benefits. The "high silica" zeolites are zeolites with molar Si/Al ratios from 10 to 100 or higher, with distinct surface characteristics. In contrast to the "low" and "intermediate" silica zeolites, representing heterogeneous hydrophilic surfaces within a porous crystal, the surface of the high silica zeolites is more homogeneous with an organophilic-hydrophobic selectivity. They generally adsorb stronger the less polar organic molecules and only weakly interact with water and other polar molecules. In terms of the present disclosure, the zeolite and/or zeolite impregnated with a rare earth metal may be a low silica zeolite, an intermediate silica zeolite, or high silica zeolite, preferably a high silica zeolite. In a preferred embodiment, the zeolite of the electrode of the present disclosure has a silica to alumina ratio in the range of 5 to 40, preferably 6 to 35, preferably 7 to 30, preferably 8 to 25, preferably 9 to 22, more preferably 10 to 20, more preferably 12 to 18, more preferably 14 to 16, or about 15.

In a preferred embodiment, the zeolite of the zeolite impregnated with a rare earth metal is a mordenite zeolite. As used herein, mordenite refers to a zeolite mineral with the general chemical formula $(Ca, Na_2, K_2)Al_2Si_{10}O_{24}.7H_2O$, preferably $Na_8Al_8Si_{40}O_{96}.n-H_2O$, preferably having the molar composition $6Na_2O:Al_2O_3 30SiO_2:780H_2O$. Mordenite is one of the six most abundant zeolites and is used commercially. Mordenite is orthorhombic (a,b,c are all unequal and all angles are 90 degrees). It often crystallizes in the form of fibrous aggregates, masses and vertically striated prismatic crystals. It may be colorless, white, or faintly yellow or pink. It typically has a Mohs hardness of 1-10, preferably 2-8, preferably 4-6, or about 5 and a density of 1.5-3.0 g/cm$^3$, preferably 1.75-2.5 g/cm$^3$, preferably 2.0-2.25 g/cm$^3$ or about 2.1 g/cm$^3$. In cases where mordenite forms well developed crystals they are often hairlike; very long, thin and delicate. Mordenite's molecular structure is a framework containing chains of five membered rings of linked silicate and aluminate tetrahedral (four oxygen atoms arranged at the points of a triangular pyramid about a central silicon or aluminum atom). Its framework is built on 5-membered rings arranged in columns parallel to the [001] axis. Hence, the framework includes elliptical micropore (6-7× 6.5-7.5 Å, preferably 6.7×7.0 Å) tunnels parallel to the c-axis and (2-3×5-6 Å, preferably 2.6×5.7Å) tunnels parallel to the b-axis. By virtue of the small nature of the latter axis, molecules are unable to pass through, and as such mordenite is generally regarded as a one-dimensional zeolite. Mordenite's high ratio of silicon to aluminum atoms makes it relatively more resistant to attack by acids than many other zeolites. Mordenite is one of the most abundant zeolites in altered volcanic deposits; it is found in volcanic rock such as rhyolite, andesite, and basalt. It may be associated with other zeolites such as stilbite and heulandite.

In a preferred embodiment, the zeolite of the zeolite impregnated with a rare earth metal is a mordenite zeolite. In a preferred embodiment, the zeolite of the zeolite impregnated with a rare earth metal is a mordenite zeolite, preferably having the molar composition 6Na$_2$O:Al$_2$O$_3$30SiO$_2$: 780H$_2$O, which has a silica to alumina molar ratio (Si/Al) in the range of 5 to 40, preferably 6 to 35, preferably 7 to 30, preferably 8 to 25, preferably 9 to 22, more preferably 10 to 20, more preferably 12 to 18, more preferably 14 to 16, or about 15. Several morphologies of the mordenite zeolite are suitable including, but not limited to spherical, circular pie, flat prismic, ellipsoidal, hexagonal star-like prism, and the like. In a preferred embodiment, the zeolite of the zeolite impregnated with a rare earth metal is a mordenite zeolite which has a flat prismic crystal with an average crystal size estimated using the Scherer equation and defined as an average crystal dimension perpendicular to the reflection plane, of 2-15 µm, preferably 2.5-12 µm, preferably 3-10 µm, preferably 4-9.5 µm, preferably 5.5-8 µm, preferably 6-7 µm.

In certain embodiments, the zeolite of the zeolite impregnated with a rare earth metal is a mordenite zeolite and is prepared by a sol-gel method. Sol-gel processing refers to a process of slow crystallization of a silica-alumina gel in the presence of alkalis and/or organic templates. The product properties depend on the reaction mixture composition, pH of the system, operating temperature, pre-reaction "seeding time" reaction time as well as templates used. The silicate sol formed by the hydrothermal method is very stable. The method of preparation of the mordenite zeolite is not viewed as particularly limiting. The method of preparation of the rare earth metal impregnated zeolite is not viewed as particularly limiting. These methods should be known to those of ordinary skill in the art.

In a preferred embodiment, the electrode of the present disclosure comprises a zeolite, preferably mordenite impregnated with a rare earth metal, preferably cerium and/or lanthanum. As used herein, "impregnated", "incorporated" or "exchanged" describes being completely or partially filled throughout, permeated, and/or infused. The rare earth metal elements or cations may be affixed inside of and/or on an outer surface of the zeolite. The rare earth metal cations or elements may be affixed on one or more surfaces of the zeolite. The rare earth metal cations or elements may be affixed to the zeolite in any reasonable chemical or physical manner, such as affixed to one or more surfaces of the zeolite, incorporated into the chemical framework of the zeolite, or alternatively, at least partially embedded within cavities and/or pore spaces of the zeolite. In a preferred embodiment, the rare earth metal ions are incorporated into the chemical framework of the zeolite, preferably mordenite. In certain embodiments, some of the Al atoms have been replaced by the rare earth metal element in the framework of the zeolite. After impregnation with rare earth metal ions the crystallinity of the zeolite, preferably mordenite, as well as the crystal morphology of the zeolite, preferably mordenite is retained. In certain embodiments, scanning electron microscopy (SEM) analysis reveals several spots on the rare earth metal impregnated zeolite indicating the binding between the zeolite crystal and the impregnated rare earth metals (FIG. 37 through FIG. 42). In certain embodiments, introduction of rare earth elements into a zeolite framework tends to alter the Lewis acid sites in the framework and can be used to adjust the amount and intensity of distribution of the acid sites. This may be attributed to the formation of hydroxyl rare earth cation species in zeolite channels which helps stabilize the zeolite framework.

As used herein, a rare earth metal or rare earth element may refer to any member of the lanthanide series (lanthanum, cerium, praseodymium, neodymium, promethium, samarium, europium, gadolinium, terbium, dysprosium, holmium, erbium, thulium, ytterbium, lutetium), the actinide series (actinium, thorium, protactinium, uranium, neptunium, plutonium, americium, curium, berkelium, californium, einsteinium, fermium, mendelevium, nobelium, lawrencium), as well as scandium, yttrium and mixtures thereof. As used herein, the terms rare earth (RE), rare earth element (REE), rare earth metal (REM), rare earth oxides (REO), rare earth elements and yttrium (REY), light rare earth elements (LREE, Sc, La, Ce, Pr, Nd, Pm, Sm, Eu, and Gd; also known as the cerium group), and heavy rare earth elements (Y, Tb, Dy, Ho, Er, Tm, Yb, and Lu; also known as the yttrium group) are used synonymously. In a preferred embodiment, the rare earth metal is at least one selected from the group consisting of lanthanum and cerium. It is equally envisaged that any rare earth metal as described herein may be employed in addition to, or in lieu, of lanthanum and/or cerium.

In a preferred embodiment, the zeolite impregnated with the rare earth metal has a weight percentage of the rare earth metal in the range of 1-15 wt % relative to the total weight of the zeolite impregnated with the rare earth metal, preferably 1.5-12 wt % preferably 2-10 wt %, preferably 4-9 wt %, preferably 5-8 wt % relative to the total weight of the zeolite impregnated with the rare earth metal. In certain embodiments, the zeolite is mordenite and the rare earth metal is lanthanum and the mordenite zeolite impregnated with lanthanum has a weight percentage of lanthanum in the range of 1-15 wt % relative to the total weight of the mordenite zeolite impregnated with lanthanum, preferably 1.25-10 wt %, preferably 1.5-5 wt %, preferably 1.75-3 wt %, or about 2 wt % relative to the total weight of the mordenite zeolite impregnated with lanthanum. In certain embodiments, the zeolite is mordenite and the rare earth metal is cerium and the mordenite zeolite impregnated with cerium has a weight percentage of cerium in the range of 1-15 wt % relative to the total weight of the mordenite zeolite impregnated with cerium, preferably 4-14 wt %, preferably 6-13 wt %, preferably 8-12 wt %, or about 10 wt % relative to the total weight of the mordenite zeolite impregnated with cerium.

In a preferred embodiment, the electrode of the present disclosure has a weight percentage of the zeolite impregnated with the rare earth metal in the range of 1-30% relative to the total weight of the electrode, preferably 2-25% by weight, preferably 3-20% by weight, preferably 4-15% by weight, preferably 5-10% by weight, or about 5% by weight relative to the total weight of the electrode.

Figure 1:
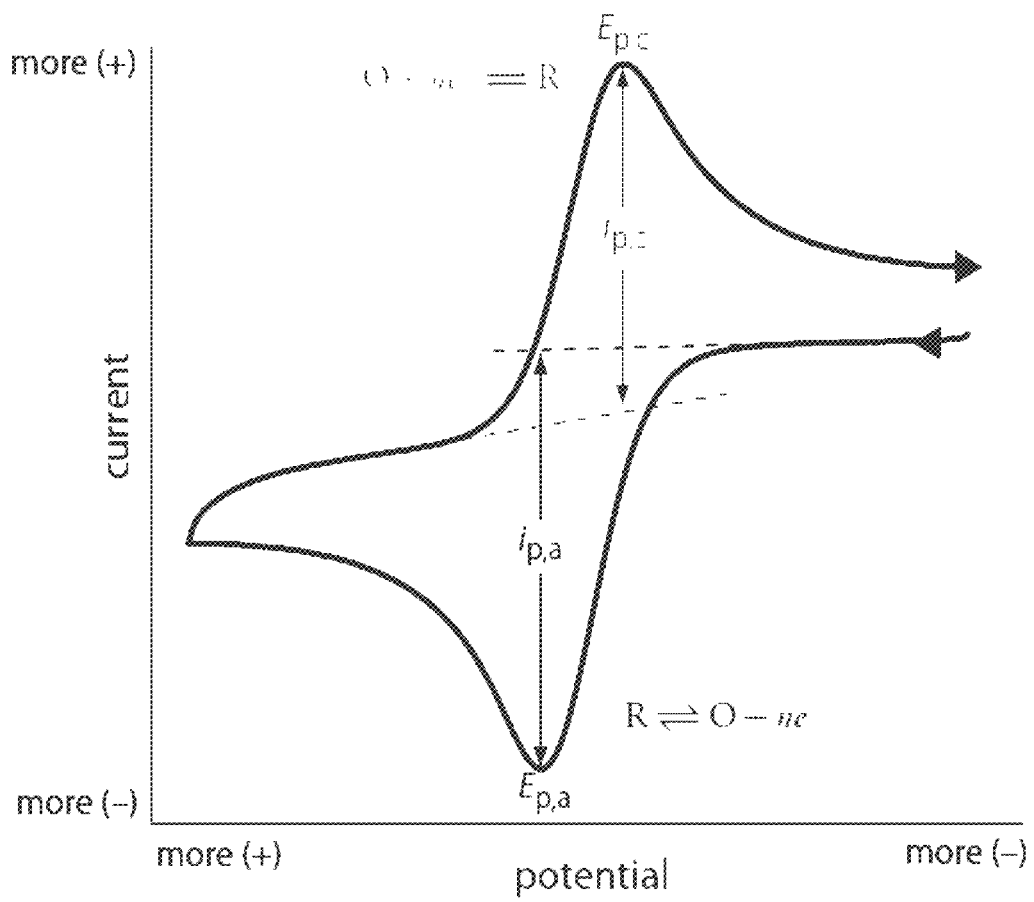
FIG. 1 is an exemplary cyclic voltammetry (CV) voltammogram of a single electron redox system.
Figure 2:
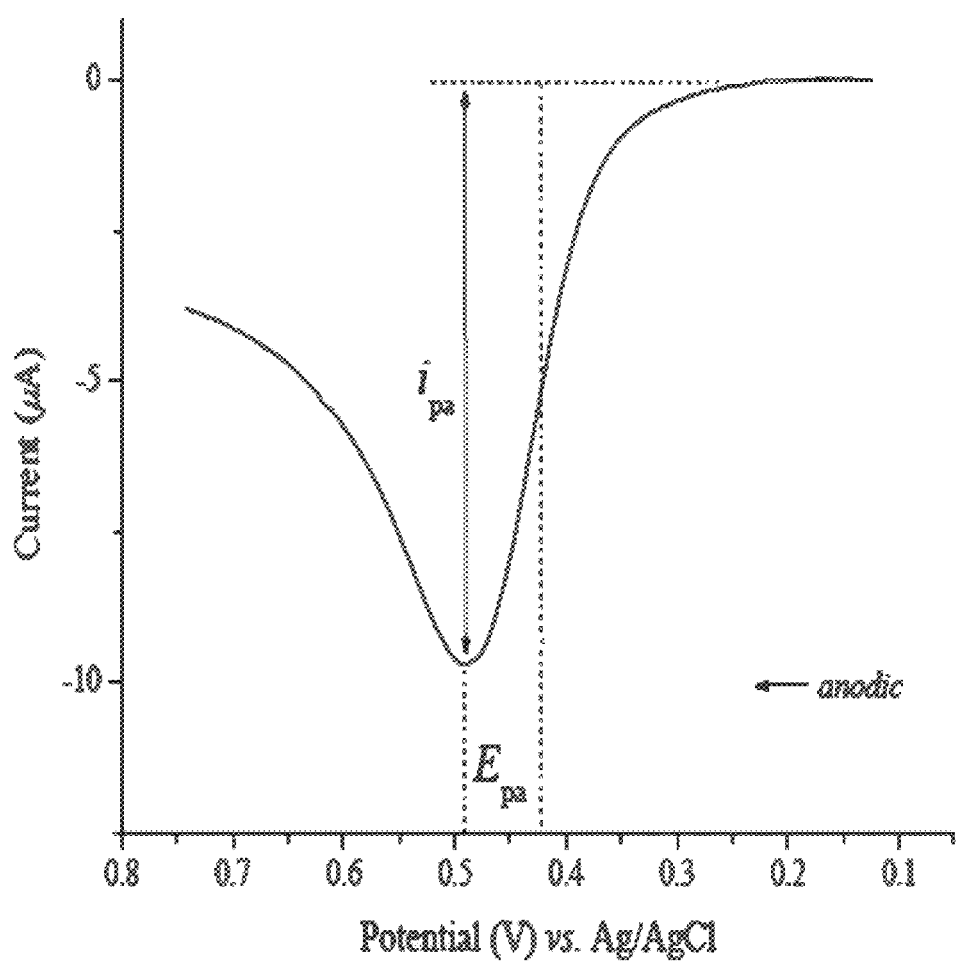
FIG. 2 is an exemplary linear sweep voltammetry (LSV) voltammogram of ferrocene.
Figure 3:
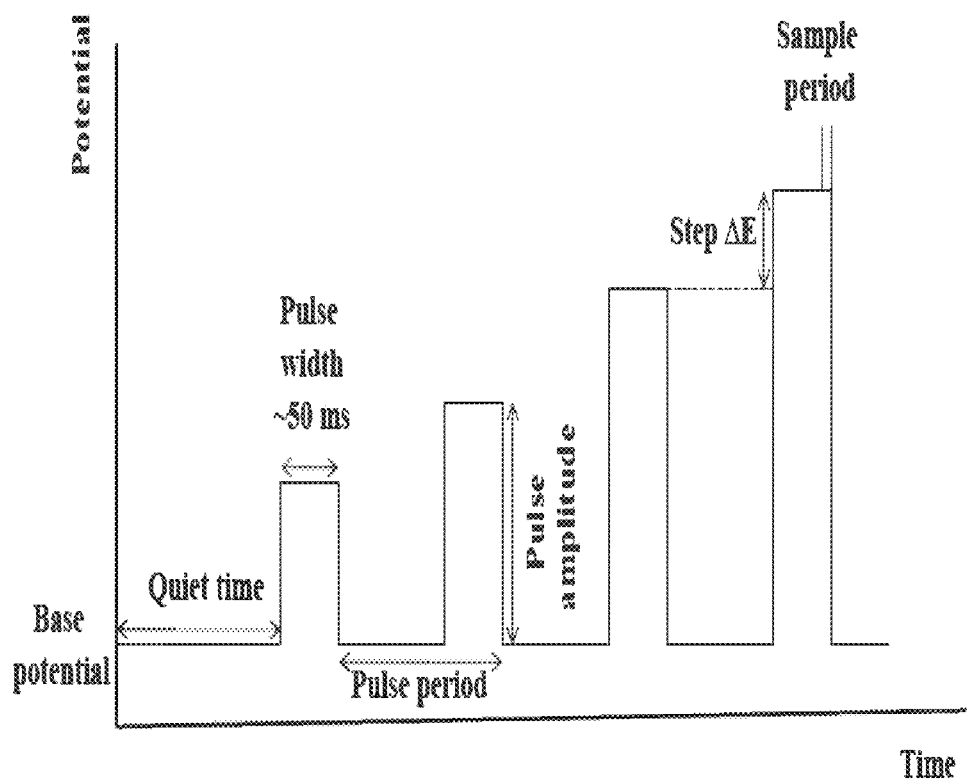
FIG. 3 is an exemplary normal pulse voltammetry (NPV) signal.
Figure 4:
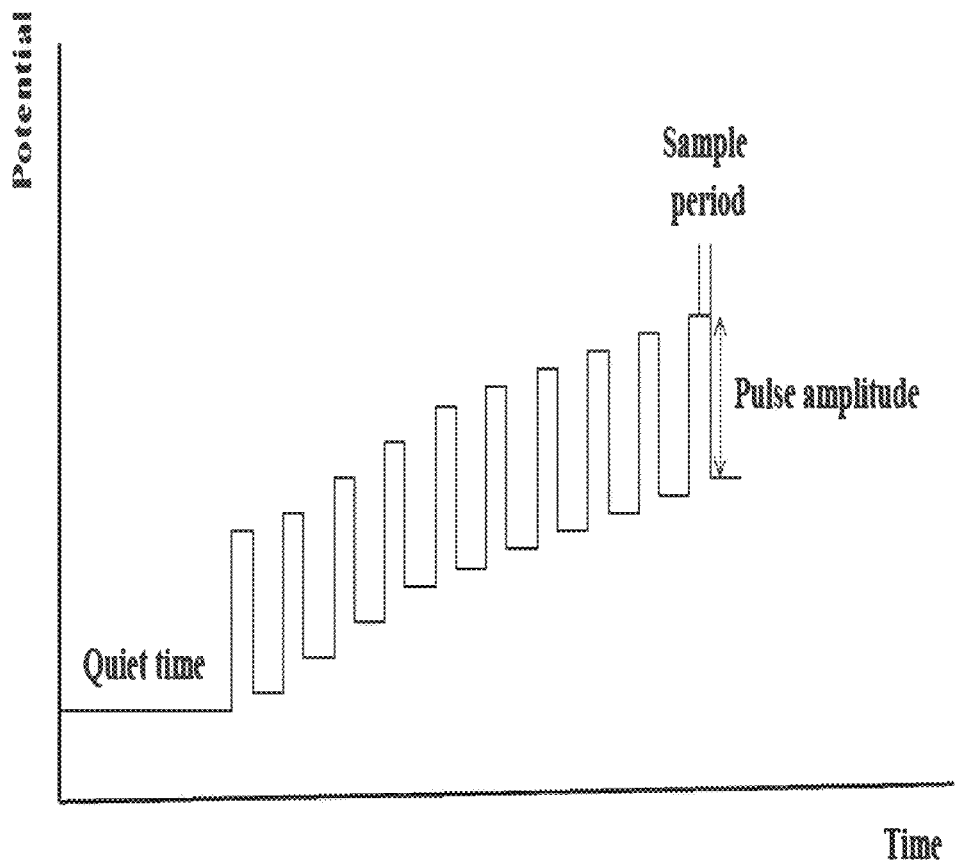
FIG. 4 is an exemplary differential pulse voltammetry (DPV) signal.
Figure 5:
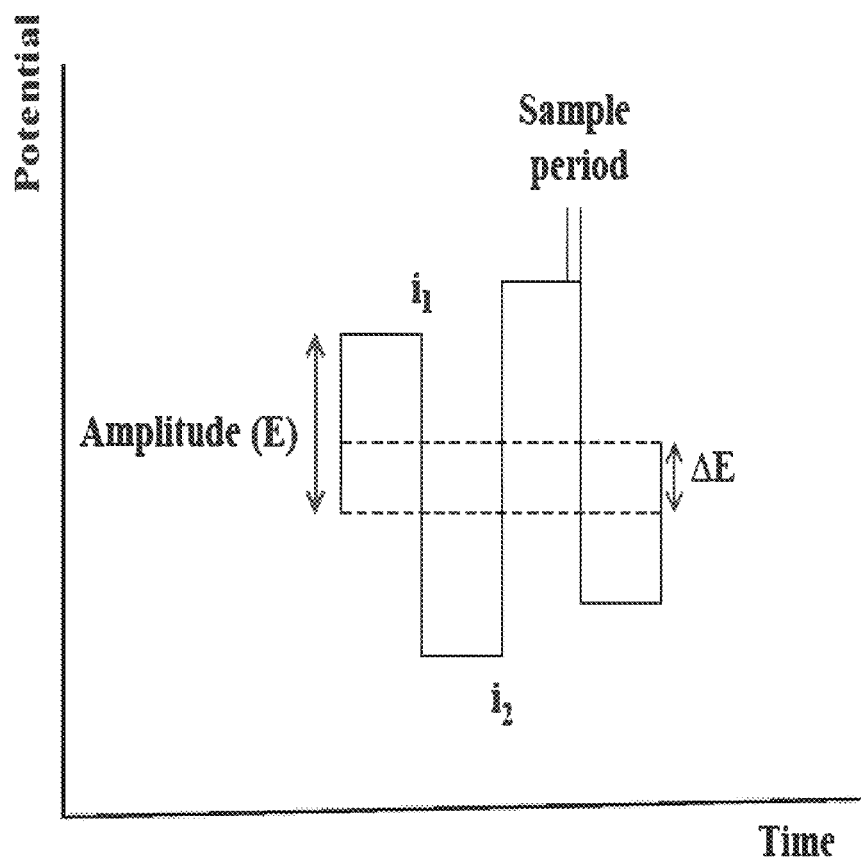
FIG. 5 is an exemplary square wave cycle waveform.
Figure 6:
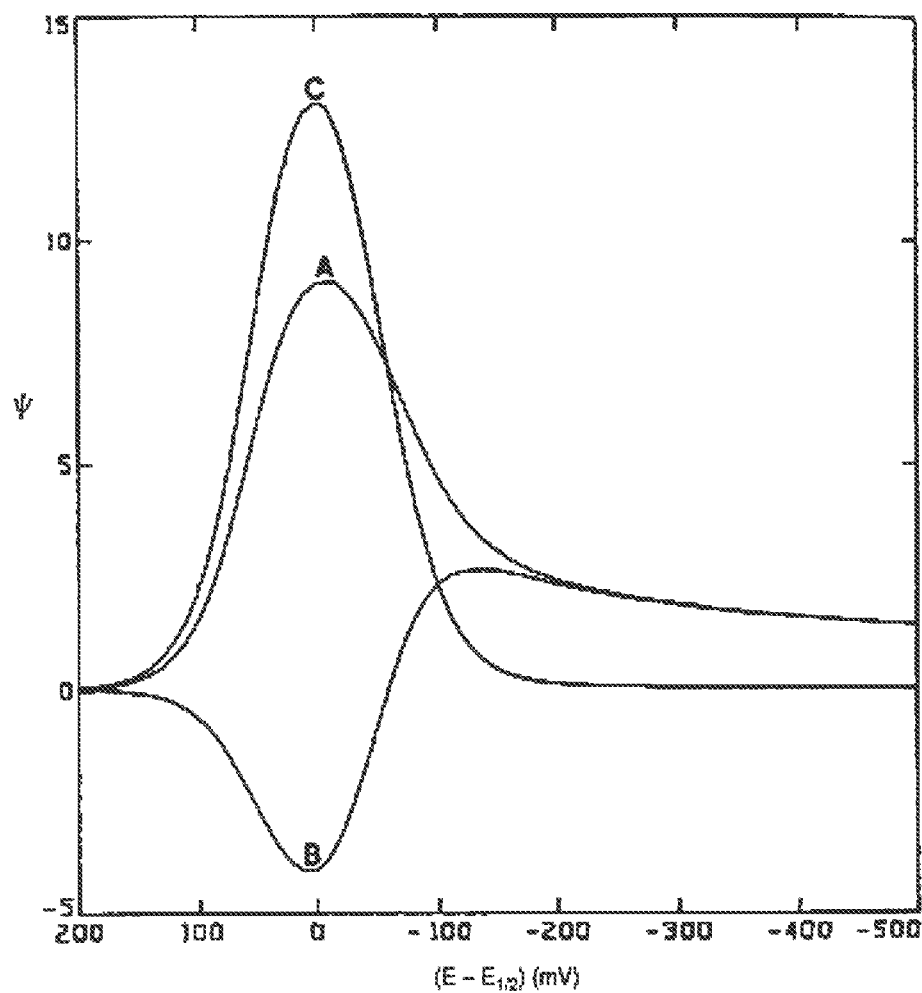
FIG. 6 is exemplary square wave voltammograms for a reversible electron transfer including forward current (A), reverse current (B), and net difference current (C).
Figure 7:
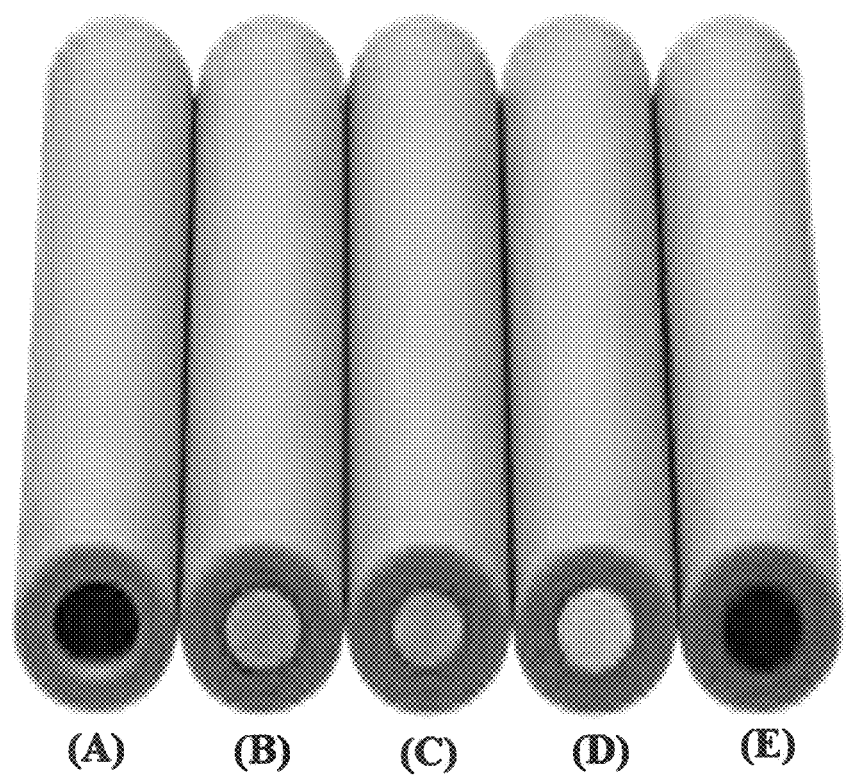
FIG. 7 is a depiction of exemplary working electrodes including empty tip (A), platinum (B), gold (C), silver (D), and glassy carbon (E).
Figure 8:
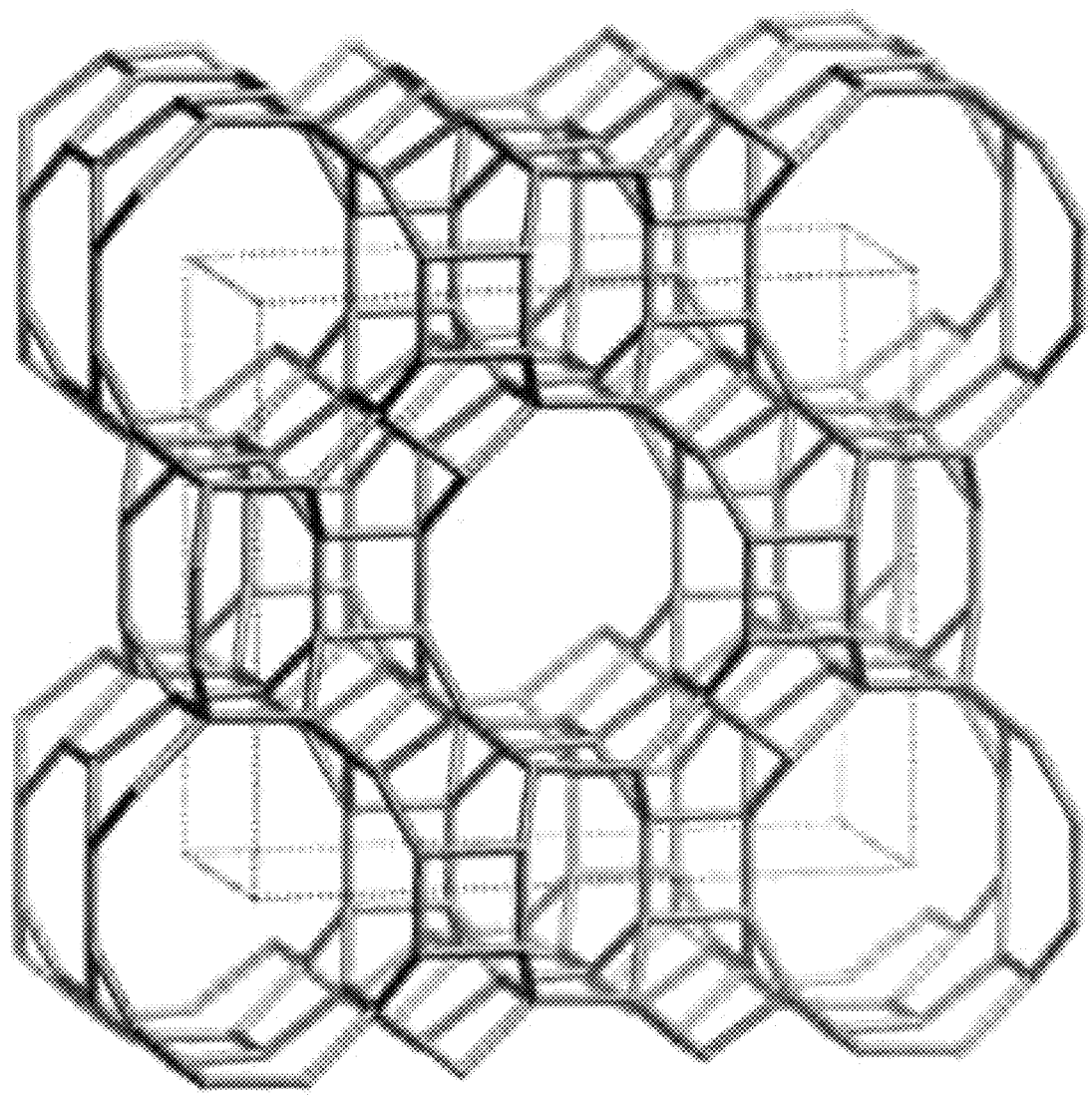
FIG. 8 is a depiction of the mordenite zeolite framework.
Figure 9:
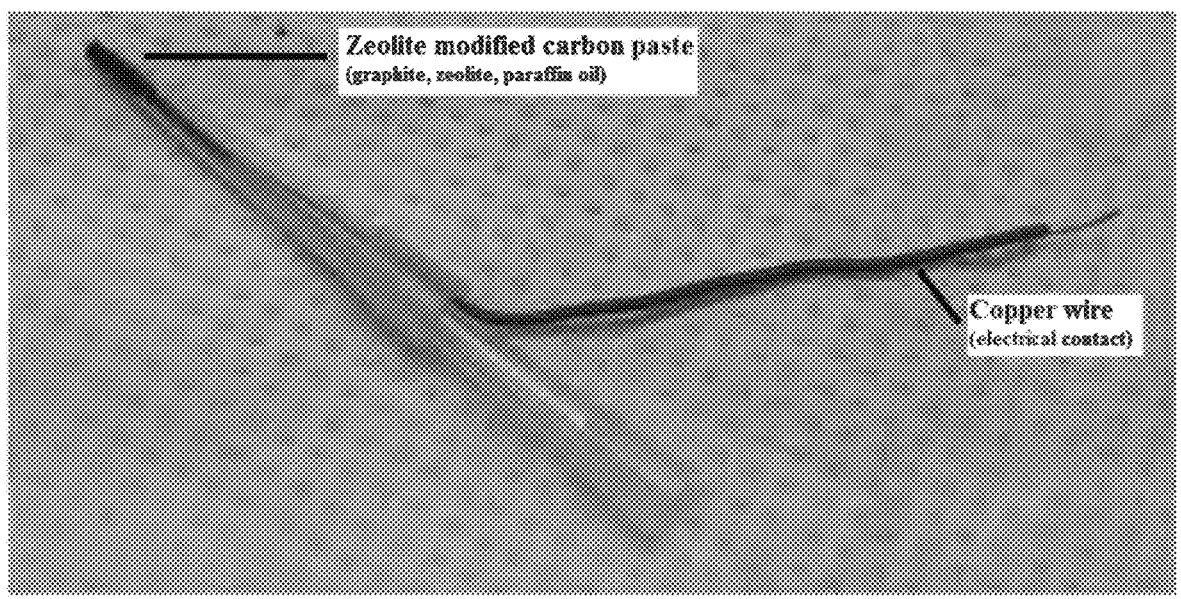
FIG. 9 is a composite electrode used as working electrode comprising rare earth impregnated zeolite modified carbon paste and copper wire as an electrical contact.

The construction of the actual physical electrode and holders or housings is not viewed as particularly limiting. Exemplary holders and/or housings include, but are not limited to tubings and rods (plugs) with hollow ends, rotated disc electrodes, piston-driven electrode holders, and a variety of commercially available electrode holders. In certain embodiments, the electrode material (i.e the electrode) in the form of a paste may be packed into a plastic micropipette tip (10-100 mm long, preferably 20-75 mm long, preferably 30-50 mm long, or about 40 mm long an 0.01-1.0 mm in diameter, preferably 0.05-0.5 mm in diameter, or about 0.01 mm in diameter). The working electrode held or housed in this manner may further comprise an electrical contact, such as for example a copper wire (FIG. 9). A variety of operational set ups for the electrode are well known to those of ordinary skill in the art.

In a preferred embodiment, the rare earth impregnated zeolite modified electrode of the present disclosure in any of its embodiments has a greater electroactive surface area relative to a substantially similar electrode lacking the zeolite impregnated with the rare earth metal, such as an electrode comprising a substantially similar zeolite free of rare earth metal exchange or incorporation. In a preferred embodiment, the rare earth impregnated zeolite modified electrode of the present disclosure in any of its embodiments has a 10-40% greater electroactive surface area relative to a substantially similar electrode lacking the zeolite impregnated with the rare earth metal, preferably 15-35%, preferably 20-30% greater electroactive surface area relative to a substantially similar electrode lacking the zeolite impregnated with the rare earth metal. In a preferred embodiment, the rare earth impregnated zeolite modified electrode of the present disclosure in any of its embodiments has an electroactive surface area of greater than 5 $mm^2$, preferably greater than 10 $mm^2$, preferably greater than 15 $mm^2$, preferably greater than 20 $mm^2$, preferably greater than 22 $mm^2$, preferably greater than 24 $mm^2$, preferably greater than 26 $mm^2$, preferably greater than 28 $mm^2$, preferably greater than 30 $mm^2$, preferably greater than 35 $mm^2$, preferably greater than 40 $mm^2$, preferably greater than 50 $mm^2$.

It is equally envisaged that the rare earth metal impregnated zeolite modified electrode of the present disclosure in any of its embodiments may be further modified in addition to zeolite impregnation. Additional suitable chemical modifications include, but are not limited to intrinsic modification, extrinsic modification (surface modification and bulk modification, chemical modifiers including, but not limited to, inorganic materials (Prussian-blue derivatives, polyoxometallates, clays, zeolites, molecular sieves, metal oxides and sol-gel derived inorganic materials), organic and organometallic compounds (organic ligands, organic catalysts, organometallic complexes, surfactants, amphiphilic modifiers, lipophilic modifiers, organic polymers and macromolecules), organic-inorganic hybrid materials, nanomaterials, surface treatments, coatings, and alterations. Additional suitable biological modifications include, but are not limited to, enzymes (oxidases, dehydrogenases, hydrolases, auxiliary enzymes), nucleic acids, immunosensors, tissues, cells, and other biomolecules.

According to a second aspect, the present disclosure relates to a method for detecting and quantifying a heavy metal ion in an aqueous solution comprising: i) contacting the aqueous solution with the electrode in any of its embodiments, ii) generating a negative deposition potential at the electrode to reduce the heavy metal ion and form a reduced heavy metal that is deposited onto the electrode, iii) scanning a potential range from the negative deposition potential in the positive direction at the electrode to oxidize and strip the reduced heavy metal from the electrode, and iv) measuring the current during the scanning. In general, the rare earth metal impregnated zeolite modified electrode in any of its embodiments is contacted with an aqueous sample and in electrical communication with a reference electrode. A potential is applied between the reference electrode and the rare earth metal impregnated zeolite modified electrode produce a current. Changes in the current as a result of reduction/oxidation/decomposition of detected analytes (i.e. heavy metal ions) can be used to determine the amount of the analyte in the sample into which the electrode is placed.

Non-limiting examples of aqueous solutions (i.e. heavy metal contaminated and/or Cd(II)/Pb(II) contaminated aqueous solutions), water sources and systems include, but are not limited to, surface water that collects on the ground or in a stream, aquifer, river, lake, reservoir or ocean, ground water that is obtained by drilling wells, run-off, industrial water, public water storage towers, public recreational pools and/or bottled water. Methods for the detection and quantification of heavy metals in aqueous solutions according to the present disclosure include contacting the rare earth metal impregnated zeolite modified electrode of the present disclosure in any of its embodiments with heavy metal contaminated water sources and systems. The methods may be carried out in tanks, containers, or small scale applications in both batch mode and fixed-bed or column mode. In a preferred embodiment, the aqueous solution comprises greater than 80% v/v of water, preferably greater than 85% v/v water, preferably greater than 90% v/v water, preferably greater than 95% v/v water, preferably greater than 99% v/v water.

In a preferred embodiment, the rare earth metal impregnated zeolite modified electrode of the present disclosure in any of its embodiments may be utilized to detect analytes. As used herein, the term "analyte" refers to a substance that is (or whose chemical constituents are) being identified, detected, and/or measured by the rare earth metal impregnated zeolite modified electrode described herein. An analyte may be a component of a fluid (i.e. vapor or liquid) sample in which the rare earth metal impregnated zeolite modified electrode is immersed or contacted with. The analyte may be various organic (i.e. uric acid and biologically important catecholamines) and inorganic species (i.e. toxic metals), preferably metal ions, more preferably heavy metal ions, in various matrices. In one embodiment, the aqueous solution is an environmental sample such as for example drinking water and the analyte is a heavy metal ion and the electrodes described herein display a lack of toxicity compared to traditional mercury electrodes. In a preferred embodiment, the aqueous solution has an initial analyte concentration of $10^{-3}$ to $10^{-12}$ M, preferably $10^{-4}$ to $10^{-10}$ M, preferably $10^{-5}$ to $10^{-9}$ M, or alternatively 1-1000 ppb, preferably 5-500 ppb, preferably 50-250 ppb.

The metal ions that are detected and/or quantified are preferably heavy metal ions. In a preferred embodiment, a heavy metal ion has a density of greater than 3.5 g/cm³ and/or an atomic weight of greater than 20. Exemplary metal ions that can be detected and/or quantified by the electrode and method of the present disclosure in any of their embodiments are of a wide range and include, but are not limited to ions of Ag, Ca, K, Zn, Na, Pb, Mn, Fe, Co, Ni, Al, Cu, Sn, Cd, Hg, Cr, Fe, Bi, Ga, Ge, Au, In, TI, Rb, Cs, As, Sb, Cr, Zn, V, Pt, Pd, Rh, and mixtures thereof. Further, these metal ions may be of any oxidation state $M^{+1}$, $M^{+2}$, $M^{+3}$, etc. In a preferred embodiment, the heavy metal is at least one selected from the group consisting of Co, Cu, Zn, Hg, As, Sr, Mo, Cd, and Pb, most preferably the heavy metal ion is at least one selected from the group consisting of lead (II), Pb (II) and cadmium (II), Cd (II). It is equally envisaged that the rare earth metal impregnated zeolite modified carbon paste electrode may be adapted or chemically modified to detect and/or quantify one or more additional metal ions in addition to, or in lieu of lead (II) and cadmium (II). In one embodiment, the additional metal ion may be any ion which is detected and/or quantified selectively or collectively by the electrode in any of its embodiments. Exemplary additional metal ions include, but are not limited to, an alkali metal (Li, Na, K, etc.), an alkaline earth metal (Mg. Ca, Sr, etc.) a lanthanide metal (La, Ce, Eu, Yb, etc.), an actinide metal (Ac, Th, etc.), or a post-transition metal (Al, Sn, Pb, In, etc.). Preferably the additional metal ion is a transition metal ion, preferably a heavy metal ion. Exemplary additional transition metals of the metal ion include, but are not limited to, Sc, Ti, Cr, Mn, Fe, Co, Ni, Cu, Zn, Y, Zr, Pd, Ag, W, Os, Au, and Hg.

In preferred embodiments, the method can be described as voltammetric or as a voltammetry method. As used herein, voltammetry refers to a category of electroanalytical methods used in analytical chemistry and various industrial processes. In voltammetry, information about an analyte (i.e. a heavy metal ion) is obtained by measuring the current as the potential is varied. In general, voltammetry experiments or voltammetry methods investigate the half-cell reactivity of an analyte. Voltammetry is a study of current as a function of applied potential. The corresponding curves (I=f(E)) are referred to as voltammograms. The potential may be varied arbitrarily step by step or continuously, and the actual current value is measured as the dependent variable. The opposite (i.e. amperometry) is also possible but uncommon. The shape of the voltammogram curves depends on the speed of the potential variation (nature of driving force) and on whether the solution is stirred or quiescent (mass transfer). Most experiments and methods control the potential (volts) of an electrode in contact with the analyte while measuring the resulting current (amperes). Exemplary voltammetric methods that may characterize the method of the present disclosure in any of its embodiments, often in terms of applied waveform of the applied biasing potential include, but are not limited to, linear sweep voltammetry, staircase voltammetry, squarewave voltammetry, cyclic voltammetry, anodic stripping voltammetry, cathodic stripping voltammetry, adsorptive stripping voltammetry, alternating current voltammetry, polarography, rotated electrode voltammetry, normal pulse voltammetry, differential pulse voltammetry, chronoamperometry, and the like. In a preferred embodiment, the method of the present disclosure is a stripping voltammetry method, most preferably an anodic stripping voltammetry method.

Voltammetry is an electrochemical technique in which the current-potential behavior at an electrode surface is measured. The potential is varied in a systematic manner to cause electroactive chemical species to be reduced or oxidized at the electrode. The resultant current is proportional to the concentration of the chemical species. Stripping voltammetry is a two-step technique in which the first step consists of the electrolytic deposition of a chemical species or analyte onto an inert electrode surface at a constant potential. This preconcentration step can involve either an anodic or cathodic process. The most common use of stripping voltammetry involves a anodic and/or cathodic process in which a metal ionic species is reduced from the solution onto an electrode. The second step consists of the application of a voltage scan to the electrode that causes an electrolytic dissolution, or "stripping", of the various species deposited at the electrode back into solution at characteristic potentials.

The remarkable sensitivity of stripping voltammetry is attributable to the preconcentration that takes place during deposition. For preconcentration to take place, the deposited material must adhere to the electrode surface, stripping voltammetry can be used to determine those chemical species that will be retained by the electrode. Stripping voltammetry is primarily a trace analytical technique. It can be used to make routine analytical determination at the sub-ppm level. In a preferred embodiment, the method is an anodic stripping voltammetry (ASV) method. As used herein anodic stripping voltammetry is a voltammetric method for quantitative determination of specific ionic species. Anodic stripping voltammetry is used to determine the concentration of trace metals. The analyte of interest (i.e. one or more heavy metal ions in an aqueous solution) is contacted with the electrode of the present disclosure in any of its embodiments, the analyte of interest is electroplated on the working electrode during a deposition (or accumulation) step, and oxidized from the electrode during a stripping step. Anodic stripping voltammetry consists of a deposition potential that is more negative than the half-wave potential of the analytes or metals to be determined and an anodic (positive going) scan to oxidize the reduced analyte or metal back into solution. The current is measured during the stripping step. The oxidation of a species is registered as a peak in the current signal at the potential at which the species begins to be oxidized. The stripping step can be either linear, staircase, squarewave, or pulse. In certain embodiments, it is equally envisaged that the working electrode or method of the present disclosure may be adapted to a cathodic stripping voltammetry (CSV) method wherein a relatively positive potential is applied during the deposition and stripping consists of a cathodic (negative going) to reduce the analyte back into solution. Exemplary analytes detected by cathodic stripping voltammetry include, but are not limited to arsenic, chloride, bromide, iodide, selenium (IV), sulfide, mercaptans (RSH), thiocyanate (SCN), and thio compounds.

This type of method or experiment generally requires at least two electrodes to perform. The working electrode, which makes contact with the analyte, must apply the desired potential in a controlled way and facilitate the transfer of charge to and from the analyte. In a preferred embodiment, the working electrode is the rare earth impregnated zeolite modified carbon paste electrode (RE-ZMCPE) described herein in any of its embodiments. A second electrode, or counter electrode, acts as the other half of the cell. This second electrode, or counter electrode, must have a known potential with which to gauge the potential of the working electrode, furthermore it must balance the charge added or removed by the working electrode. While this is a viable setup it suffers from it being difficult for a single electrode to maintain a constant potential while passing current to counter redox events at the working electrode. In a solution to this problem, the roles of supplying electrons and providing a reference potential are divided between two separate electrodes. Anodic stripping voltammetry generally incorporates three electrodes, a working electrode, an auxiliary electrode (also referred to as a counter electrode) and a reference electrode. The reference electrode is a half cell with a known reduction potential. Its only role is to act as reference in measuring and controlling the working electrode's potential and at no point does it pass any current. The auxiliary (second or counter) electrode passes all the current needed to balance the current observed at the working electrode. In order to achieve this current, the auxiliary electrode will often swing to extreme potentials at the edges of the solvent window, where it oxidizes or reduces the solvent or supporting electrolyte. These electrodes the working, reference, and auxiliary make up the modern three electrode system. In a preferred embodiment, the method is performed in a three electrode system, comprising a working electrode, an auxiliary (or counter) electrode and a reference electrode.

In a preferred embodiment, the rare earth impregnated zeolite modified carbon paste electrode (RE-ZMCPE) described herein in any of its embodiments functions as a working electrode. The auxiliary or counter electrode is not viewed as particularly limiting as long as it does not react with the bulk of the analyte solution and conducts well. In a preferred embodiment, the counter electrode comprises or is fabricated from electrochemically inert materials including, but not limited to, platinum, gold or carbon, in a most preferred embodiment the counter electrode is a platinum wire. In another embodiment, the counter or auxiliary electrode may be isolated from the working electrode, such as by means of a glass flit. Such isolation prevents any byproducts generated at the auxiliary electrode from contaminating the main test solution. The reference electrode is preferably an aqueous electrode. Exemplary reference electrodes include, but are not limited to, a standard hydrogen electrode (SHE), a normal hydrogen electrode (NHE), a reversible hydrogen electrode (RHE), a saturated calomel electrode (SCE), a copper-copper(II) sulfate electrode (CSE), a silver chloride (Ag/AgCl) electrode, a pH buffered solution pH electrode, a palladium-hydrogen electrode, a dynamic hydrogen electrode (DHE), a mercury-mercurrous sulfate electrode (MSE), and the like. In a most preferred embodiment, the reference electrode is a silver chloride (Ag/AgCl) electrode.

In certain embodiments, the aqueous solution may further comprise a supporting electrolyte. As used herein, a supporting electrolyte in electrochemistry refers to an electrolyte containing chemical species that are not electroactive (within the range of potentials used). Supporting electrolytes are widely used in electrochemical measurements when control of electrode potentials is required. This may increase the conductivity of the solution, eliminate the transport of electroactive species by ion migration in the electric field, maintain constant ionic strength or maintain constant pH. In a preferred embodiment, the aqueous solution further comprises a buffer solution as a supporting electrolyte. As used herein, a buffer solution (more precisely, pH buffer or hydrogen ion buffer) refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications. In certain embodiments, the aqueous sample further comprises a buffer solution selected from the group consisting of citrate buffer, phthalate buffer, acetate buffer, phosphate buffer, and sulphate buffer, more preferably phosphate buffer. In a preferred embodiment, the concentration of the buffer in the aqueous solution may range from 0.01-1.0 M, preferably 0.01-0.5 M, preferably 0.05-0.25 M, preferably 0.08-0.2 M, or about 0.1 M. In a preferred embodiment, the aqueous sample has a pH in the range of 3-5, preferably 3.2-4.8, preferably 3.4-4.6, preferably 3.5-4.5, preferably 3.6-4.4, preferably 3.8-4.2 or about 4.0.

In one step of the method for detecting and quantifying a heavy metal ion in an aqueous solution, the aqueous solution is contacted with the rare earth metal impregnated zeolite modified electrode of the present disclosure in any of its embodiments. Preferably at least one end of the electrode is in contact with the aqueous solution or sample, preferably the length of the electrode material immersed in the aqueous solution may range from 10-100 mm, preferably 20-80 mm, preferably 30-70 mm, preferably 40-60 mm. In certain embodiments, the method may further comprise a deaerating step subsequent to the contacting wherein the aqueous solution is purged for 1-15 minutes, preferably 2-10 minutes with a purified inert gas (i.e. nitrogen, argon) to eliminate interferences from oxygen. Optionally the inert gas may be passed through a scrubbing tower filled with supporting electrolyte in order to allow the nitrogen stream to be saturated with the electrolyte solution to eliminate the possibility of pH changes or volatilization in the cell. In certain embodiments, the method may further comprise a conditioning or cleaning step subsequent to the deaerating. As used herein, conditioning is a term that denotes electrolytic cleaning of the electrode surface. A specified potential, preferably a more oxidizing potential than the analyte of interest, is applied to the electrode for a controlled time in order to remove contaminants or materials not removed during a stripping step from the electrode. In certain embodiments, conditioning is not required with the electrode of the present disclosure as a new electrode is fabricated for each determination or analysis. In contrast, conditioning may be a necessity when the same electrode surface is used in subsequent determinations or analyses. In embodiments where the electrode is used to detect and quantify metals, the conditioning potential should be positive with respect to the half-wave potential of the analyte to ensure the oxidation of metals back into solution. In a preferred embodiment, the conditioning potential is greater than −0.5 V, preferably greater than −0.4 V, preferably greater than −0.3 V, preferably greater than −0.2 V, preferably greater than 0.1 V, preferably greater than 0.0 V and is generally suitable for removing any such contaminants without affecting the electrode. The solution is optionally stirred during conditioning, preferably stirred, and in preferred embodiments the conditioning time is 10-360 seconds, preferably 20-240 seconds, preferably 30-180 seconds, preferably 60-120 seconds.

In one step of the method for detecting and quantifying a heavy metal ion in an aqueous solution, a negative deposition potential is generated at the rare earth metal impregnated zeolite modified electrode of the present disclosure in any of its embodiments to reduce the heavy metal ion and form a reduced heavy metal that is deposited onto the electrode. Briefly, the potential is held at a lowered potential, low enough to reduce the analyte and deposit it on the electrode.

In the deposition step, the deposition potential is applied to the working electrode (i.e. the rare earth metal impregnated zeolite modified electrode) to cause the material of interest to be deposited onto the surface of the working electrode. The solution is optionally and preferably stirred during deposition to maximize analyte-electrode contact, preferably stirred at 100-1000 rpm, preferably 200-800 rpm, preferably 400-700 rpm, or about 600 rpm. Generally, the selection of the deposition potential depends upon whether the material to be determined is oxidized or reduced. For a reducible metal, the deposition potential should be negative with respect to the half-potential of the metal. In contrast, for oxidizable materials, the deposition potential should be selected such that it is positive with respect to the half-wave potential. The choice of the deposition potential can provide some selectivity in the measurement. For example, a dc polarogram of lead and cadmium shows a first plateau as the diffusion-limited current due to the reduction of lead and a second plateau due to the diffusion-limited current of both lead and cadmium. Deposition at a certain potential may only yield a stripping peak for lead. There is no contribution to the stripping voltammogram from the cadmium also present in solution since deposition at this potential reduces lead only. Deposition at a more negative potential yields a somewhat higher stripping peak still with no contribution from cadmium. Deposition at an even more negative potential (more negative than −0.6 V) yields two stripping peaks since deposition at this potential is negative enough to reduce cadmium and lead simultaneously. In this manner, multiple heavy metal ions, 2-12, preferably 2-8, preferably 2-6, preferably 2-3 may be simultaneously detected and/or quantified. In a preferred embodiment, the deposition potential is negative, and the negative deposition potential is in the range of −2.0 V to −0.2 V, preferably −1.8 V to −0.4 V, preferably −1.6 V to −0.6 V, preferably −1.5 V to −0.8 V, preferably −1.4 V to −1.0 V, preferably −1.3 V to −1.1 V, or about −1.2 V.

The deposition time is an important experimental parameter that is unique to stripping voltammetry. If more sensitivity is required, an analyst may increase the deposition time. This increases the degree of preconcentration, making a greater amount of deposited analyte available at the electrode during the stripping step. In a preferred embodiment, the reduced heavy metal is deposited over a time period (i.e. the deposition time) in the range of 10-250 seconds, preferably 15-225 seconds, preferably 20-200 seconds, preferably 30-180 seconds, preferably 50-175 seconds, preferably 75-150 seconds, preferably 100-140 seconds, preferably 110-125 seconds, or about 120 seconds. In certain embodiments, this deposition step may further comprise an equilibration period. During equilibration, the deposition potential is applied to the working electrode, but stirring is halted. This may allow convection currents from the stirring to decrease to a negligible level and also allow time for the deposited material to stabilize. In a preferred embodiment, the equilibration time is 1-120 seconds, preferably 10-60 seconds, preferably 20-40 seconds, or about 30 seconds.

In one step of the method for detecting and quantifying a heavy metal ion in an aqueous solution, a potential range is scanned from the negative deposition potential in the positive direction at the rare earth metal impregnated zeolite modified electrode of the present disclosure in any of its embodiments to oxidize and strip the reduced heavy metal from the electrode and the current is measured during the scanning.

In the stripping step, an excitation waveform is applied which electrolyzes the deposited material back into the solution. The current is then measured versus the applied potential. The materials deposited at the electrode will strip at potentials very close to their half-wave potentials. The measured current at these potentials is proportional to the concentration of the analyte in the original sample. Increases in sensitivity may be noted for different waveforms of the biasing or striping potential, the biasing or stripping potential may have a waveform of linear voltammetry, linear sweep voltammetry, square wave voltammetry, cyclic voltammetry, or pulse voltammetry. In a preferred embodiment, the scanning and the measuring are performed with square wave voltammetry and the biasing potential or stripping potential has the waveform of square wave voltammetry. In a preferred embodiment, the waveform has amplitude ranging from 0.01-1.0V, preferably 0.05-0.5 V, preferably 0.08-0.4 V, preferably 0.1-0.35 V, preferably 0.15-0.3 V and the waveform has a frequency of 1-150 Hz, preferably 5-100 Hz, preferably 10-80 Hz, preferably 15-60 Hz, preferably 20-50 Hz. In a preferred embodiment, the stripping is performed without stripping. A slow (2-5 mV/sec) or a more rapid (10-100 mV/sec) scan rate may be applied to the electrode. In a preferred embodiment, the scanning is performed at a scan rate of 2-500 mV/s, preferably 5-400 mV/s, preferably 10-350 mV/s, preferably 15-300 mV/s, preferably 20-250 mV/s, preferably 25-200 mV/s, preferably 50-150 mV/s. The scanning range must span the potential region where the chemical specie(s) of interest are electrolyzed back into solution and the current of peaks corresponding to the analytes that are present are measured, thus each metal phase species is selectively oxidized during the anodic potential sweep, such as for example −2.0 to 0.0 V, preferably −1.8 to 0.0 V, preferably −1.6 to 0.0 V, preferably −1.4 to 0.0 V.

In certain embodiments, the rare earth metal impregnated zeolite modified electrode of the present disclosure in any of its embodiments is not reused and a new electrode is fabricated for each determination or analysis. In certain embodiments, the rare earth metal impregnated zeolite modified electrode of the present disclosure in any of its embodiments may be reusable and may be capable of repeated detection without calibration or replacement. In certain embodiments, the electrode may be polished before immersion in the aqueous solution or reuse, such as for example with alumina particles with a size ranging from 0.05-0.5 μm, preferably 0.1-0.5 μm, more preferably 0.2-0.3 μm. The electrode may further be rinsed with solvents before immersion in the aqueous solution or reuse such as for example ethanol, acetone, and water to remove impurities.

In one or more embodiments, the heavy metal ion detection and quantification method described herein may further comprise and/or be preceded by calibration procedures with steps including measuring the voltammogram of a plurality of calibration samples comprising a series of known amounts of the analyte or heavy metal ion in the same medium as the aqueous solution to be tested, in order to obtain a calibration curve for the rare earth metal impregnated zeolite modified electrode. In a preferred embodiment, the calibration is performed over two concentration ranges of the analyte, such as for example 50-500 ppb and 5-50 ppb. Preferably, the square wave stripping voltammetry shows a linear relationship between the stripping current and the concentration of the analyte or heavy metal ion. In a preferred embodiment the concentration limits of detection for many metals is in the low ppb to high ppt range (S/N=3) and compares favorably with atomic absorption spectroscopy (AAS) or inductively coupled plasma (ICP) analysis In a preferred embodiment the method and the rare earth metal impregnated zeolite modified electrode has a limit of detection in the range of 0.005-0.5 μg $L^{-1}$, preferably 0.01-0.45 μg $L^{-1}$, preferably 0.02-0.4 μg $L^{-1}$, preferably 0.03-0.35 μg L$^{-1}$, preferably 0.035-0.3 µg L$^{-1}$, preferably 0.05-0.25 µg L$^{-1}$, preferably 0.10-0.20 µg L$^{-1}$. In a preferred embodiment the method and the rare earth metal impregnated zeolite modified electrode has a limit of quantitation in the range of 1-15 µg L$^{-1}$, preferably 2-12 µg L$^{-1}$, preferably 3-10 µg L$^{-1}$, preferably 3.5-8 µg L$^{-1}$, preferably 4-6 µg L$^{-1}$.

In a preferred embodiment, the rare earth metal is lanthanum and the heavy metal ion is Pb(II), and the method has a Pb(II) detection limit in the range of 0.15-0.30 µg L$^{-1}$, preferably 0.18-0.28 µg L$^{-1}$, preferably 0.20-0.25 µg L$^{-1}$, preferably 0.21-0.24 µg L$^{-1}$, or about 0.225 µg L$^{-1}$. In a preferred embodiment, the rare earth metal is lanthanum and the heavy metal ion is Cd(II), and the method has a Cd(II) detection limit in the range of 0.05-0.20 µg L$^{-1}$, preferably 0.08-0.18 µg L$^{-1}$, preferably 0.10-0.15 µg L$^{-1}$, preferably 0.11-0.14 µg L$^{-1}$, or about 0.122 µg L$^{-1}$. In a preferred embodiment, the rare earth metal is cerium and the heavy metal ion is Pb(II), and the method has a Pb(II) detection limit in the range of 0.02-0.15 µg L$^{-1}$, preferably 0.04-0.12 µg L$^{-1}$, preferably 0.05-0.10 µg L$^{-1}$, preferably 0.06-0.08 µg L$^{-1}$, or about 0.07 µg L$^{-1}$. In a preferred embodiment, the rare earth metal is cerium and the heavy metal ion is Cd(II), and the method has a Cd(II) detection limit in the range of 0.01-0.10 µg L$^{-1}$, preferably 0.02-0.08 µg L$^{-1}$, preferably 0.03-0.07 µg L$^{-1}$, preferably 0.04-0.06 µg L$^{-1}$, preferably 0.04-0.05 µg L$^{-1}$, or about 0.046 µg L$^{-1}$.

In addition to the sensitivity of the method is preferably highly reproducible. As used herein, relative standard deviation (RSD) or coefficient of variation (CV) refers to a standardized measure of dispersion of a probability distribution or frequency distribution. It is often expressed as a percentage, and is defined as the ratio of the standard deviation to the mean (or its absolute value). The CV or RSD is widely used in analytical chemistry to express the precision and repeatability of an assay, technique, or method. In a preferred embodiment, the method of the present disclosure in any of its embodiments and the rare earth metal impregnated zeolite modified electrode of the present disclosure in any of its embodiments has a reproducibility as measured by a relative standard deviation in the range of 1-5%, preferably 1.5-4%, preferably 1.75-3.5%, preferably 2-3%, preferably 2.2-3.8%.

According to another aspect, the present disclosure relates to a sensing device. The electrode of the present disclosure described herein in any of its embodiments may be part of (i.e. integrated in) the sensing device which may further comprise an aforementioned reference electrode, counter electrode, or both. A number of voltammetric systems are produced commercially for the determination of specific species that are of interest in industry and research. Although these devices may sometimes be called electrodes, they are in fact more often complete voltammetric cells that are better referred to as sensors. These sensors or sensing devices can be employed for the analysis of various organic and inorganic analytes, preferably heavy metal ions, in various matrices and may take the form of inexpensive and field deployable instrumentation. The sensing device may also include a housing that comprises the electrode of the present disclosure in any of its embodiments and a fluid distribution manifold that comprises a fluid flow path that is in fluid communication with the electrode of the present disclosure in any of its embodiments, the counter electrode, and/or the reference electrode. In certain embodiments, the fluid flow path can bring a fluid comprising at least one analyte, preferably a metal ion, preferably a heavy metal ion, most preferably a Pb(II) and/or Cd(II) heavy metal ion into contact with the electrode of the present disclosure in any of its embodiments for sensing.

In certain embodiments, the sensing device may be in communication with at least one readout device that may generally be capable of measuring the current and/or potential at the electrode of the present disclosure in any of its embodiments. In most preferred embodiments, the readout device may be a set of electronics. An electronic readout device, for example, may be capable of detecting current changes. Moreover, the readout device may be a component of the sensing device or may be remotely separated from the sensing device. Furthermore, the readout device may also be linked to an adapter that can interface with a controller device. Preferably, a readout circuit is employed to enable determination of the presence and/or amount of an analyte, preferably a heavy metal ion, and may form part of the readout device.

In certain embodiments, the readout circuit may be configured to measure the current and/or the potential at the rare earth metal impregnated zeolite described herein. Further, the readout circuit may also be configured to indicate the current and/or potential value(s) to a user of the sensing device such that said user can detect the presence of the analyte, preferably a heavy metal ion, and quantify it based on this measurement. In certain embodiments, to achieve this, the readout circuit may comprise an electronic display and/or loudspeaker or other interface for presenting the current and/or potential value(s) to the user, and may further comprise a transmitter and/or transceiver for transmitting the data to another device. This latter feature is envisaged to enable the user to monitor the environment from a remote location. In another embodiment, the readout circuit may be configured to determine the presence and/or amount of analyte, preferably a heavy metal ion, using the current and/or potential value(s) and indicate the result to the user, with or without the current and/or potential value(s). In such embodiments, the user is provided with the end result without requiring derivation from the raw data.

In certain embodiments, the practice of this analysis may be performed by a processor in combination with a storage medium. For example, a processor may be configured to receive the current and/or potential value(s) from the readout circuit and compare this with predetermined calibration data (i.e. predetermined measurements of current and/or potential difference versus analyte concentration) from the storage medium to determine the presence and/or amount of analyte.

It is equally envisaged that the method, detectors and sensors described herein may be adapted to a variety of electroanalysis, including, but not limited to, the determination of inorganic ions, complex species, and molecules including, but not limited to, noble metals, heavy metals, metalloids, metals of the iron, manganese, chromium, and vanadium groups, platinum metals and uranium, metal of the fourth and third groups, metals of rare earths, metals of alkaline earths and alkaline metals, non-metallic ions, complexes, and neutral molecules, the determination of organic substances and environmental pollutants, pharmaceutical and clinical analysis, and the determination of biologically important compounds including, but not limited to alcohols, aldehydes, ketones and acids, amino compounds (i.e. amides, amines, amino acids), antioxidants and phenolic compounds, carbohydrates and related compounds, coenzymes, enzymes, proteins and related compounds, hormones, phytohormones and related compounds, purines, pyridines, and pyrimidines, vitamins, and to employ whole cells, microorganisms, tissues, and tissue extracts as modifiers.

The present embodiments are being described with reference to specific example embodiments included to illustrate not limit the scope of the invention. The examples below are intended to further illustrate methods protocols for preparing and characterizing the rare earth metal impregnated zeolite modified electrodes of the present disclosure. Further, they are intended to illustrate assessing the properties and applications of these electrodes. They are not intended to limit the scope of the claims.

Example 1

General Materials and Methods of Characterization for Prepared Electrodes

All solvent and reagents used were of standard purity and of analytical grade. The chemicals include: NaOH (PRS codex, Panreac Qumica), silica gel (pore size 60 Å, 70-230 mesh, Sigma-Aldrich), colloidal silica (LUDOS, 40 wt %, Sigma-Aldrich), sodium silicate (reagent grade, Lot: MKBG3583, Sigma-Aldrich), fumed silica (175-225 m$^2$/g surface, 99.8%, Sigma-Aldrich), NaAlO$_2$ (anhydrous, Sigma-Aldrich), NaH$_2$PO$_4$ and Na$_2$HPO$_4$ (fluka), K$_4$Fe(CN)$_6$ (BDH chemicals), KCl (anhydrous, Sigma-Aldrich), phosphoric acid (BDH, analar grade), NH$_4$OH (Fisher scientific), H$_2$SO$_4$ (Panreac Quimica), glacial acetic acid and ammonium acetate (Fisher scientific). Solutions of Pb(II) and Cd(I) were prepared from 1000 ppm stock solutions (spectroscopic grade, BDH chemicals). All solutions were freshly prepared with double distilled water obtained from labstrong nanopure water distiller (Thermoscientific).

Powder X-ray diffraction (XRD) pattern of the crystal was recorded on Rigaku miniflex II X-ray diffractometer using CuKα radiation (?=1.5418 Å) with 2θ from 5° to 50° and a scanning step of 0.02. Morphology of the crystal was obtained by field emission scanning electron microscopy (FESEM) LYRA 3 dual beam, Tescan. Samples were coated with gold prior to analysis. Solid state $^{27}$Al and $^{29}$Si MAS NMR were carried out on a JEOL Lambda-500 Multi Nuclear Magnetic Resonance spectrometer with a solid state MAS probe. The $^{29}$Si MAS Spectra were taken at a pulse interval of 10 s with 20,000 scans per sample and a spin of 4 kHz. The spectra were processed with 40 Hz line broadening and chemical shifts were determined relative to TMS as an external reference. Electrochemical experiments were performed on a CHI 760E electrochemical work station (CH instruments, US). An Ag/AgCl electrode was used as reference electrode and a platinum wire as the auxiliary electrode. The working electrode was a carbon paste electrode modified or unmodified with zeolite.

The present disclosure will be better understood with reference to the following abbreviations: atomic absorption spectrometry (AAS), anodic stripping voltammetry (ASV), cyclic voltammetry (CV), cathodic stripping voltammetry (CSV), chemically modified electrode (CME), differential pulse voltammetry (DPV), dropping mercury electrode (DME), double deionized water (DDW), environmental protection agency (EPA), energy dispersive X-ray spectrometry (EDX), fluid catalytic cracking (FCC), graphite furnace atomic absorption spectrometry (GFAAS), inductively coupled plasma optical emission spectrometry (ICP-OES), inductively coupled plasma mass spectrometry (ICP-MS), international zeolite association (IZA), linear sweep voltammetry (LSV), limit of detection (LOD), maximum contaminant level (MCL), mordenite (MOR), magic angle spinning (MAS), normal pulse voltammetry (NPV), nuclear magnetic resonance spectrometry (NMR), parts per million (ppm), parts per billion (ppb), rare earth (RE), revolutions per minute (rpm), square wave voltammetry (SWV), scanning electron microscopy (SEM), square wave anodic stripping voltammetry (SWASV), working electrode (WE), X-ray diffraction spectrometry (XRD), zeolite modified electrode (ZME), and zeolite modified carbon paste electrode (ZMCPE).

Example 2

General Fabrication of Prepared Electrodes

In one step the mordenite zeolite (MOR) was synthesized. A gel having the molar composition 6Na$_2$O:Al$_2$O$_3$:30SiO$_2$:780H$_2$O was synthesized according to the following procedure; 2.10 g of NaOH was dissolved in 20 g of double deionized water (DDW). To this solution, 0.63 g of NaAlO$_2$ was added and the mixture was stirred until dissolution. Thereafter, 34.13 g of DDW was added while stirring. Finally, 6.95 g of SiO$_2$ was added and the mixture was stirred for 1 hour (aging time). The resulting gel was then transferred to a Teflon-lined stainless steel autoclave and crystallization was carried out under hydrothermal conditions at 180° C. for 48 h. The material resulting after crystallization was centrifuged and washed with DDW until the pH dropped below 9. The sample was allowed to dry overnight at room temperature in order to obtain the crystal powder. The crystal was calcined at 550° C. to expel all organic matter present. The zeolite whose molar composition was 6Na$_2$O:Al$_2$O$_3$:30SiO$_2$:780H$_2$O was characterized by X-ray diffraction (XRD), scanning electron microscopy (SEM), energy-dispersive X-ray spectroscopy (EDX) and nuclear magnetic resonance (NMR).

This zeolite was further impregnated with rare earth metal. An appropriate amount of the metal precursors (La(NO$_3$)$_3$.6H$_2$O and/or Ce(NO$_3$)$_3$.6H$_2$O) required to make 2 wt %, 5 wt % and 10 wt % of La and/or Ce impregnated zeolites was dissolved in ethanol (40 g) and was mixed with 2 g of the prepared mordenite zeolite under vigorous stirring. The resulting slurry was dried overnight in a fume hood and was later calcined at 550° C. for 4 h in static air (temperature ramp 20° C./min). The metal impregnated zeolite was used in the fabrication of the final electrode.

The zeolite modified carbon paste electrode (ZMCPE) was prepared by mixing an appropriate amount of graphite, zeolite and paraffin oil in order to form a paste according to various ratios as described below. The paste was packed into the end of the tip of a micropipette (40 mm long, 0.1 mm in diameter) with copper wire as an electrical contact. The electrode was renewed after every experiment by packing in a fresh paste and smoothening by polishing the surface on a weighing paper. Bare carbon paste electrode was prepared in the same manner without the addition of zeolite (graphite and paraffin oil only) and was used for comparison. FIG. 9 shows the finished composite electrode.

Example 3

Synthesis and Characterization of a Prepared Lanthanum Impregnated Zeolite Modified Carbon Paste Electrode (La-ZMCPE)

Figure 10:
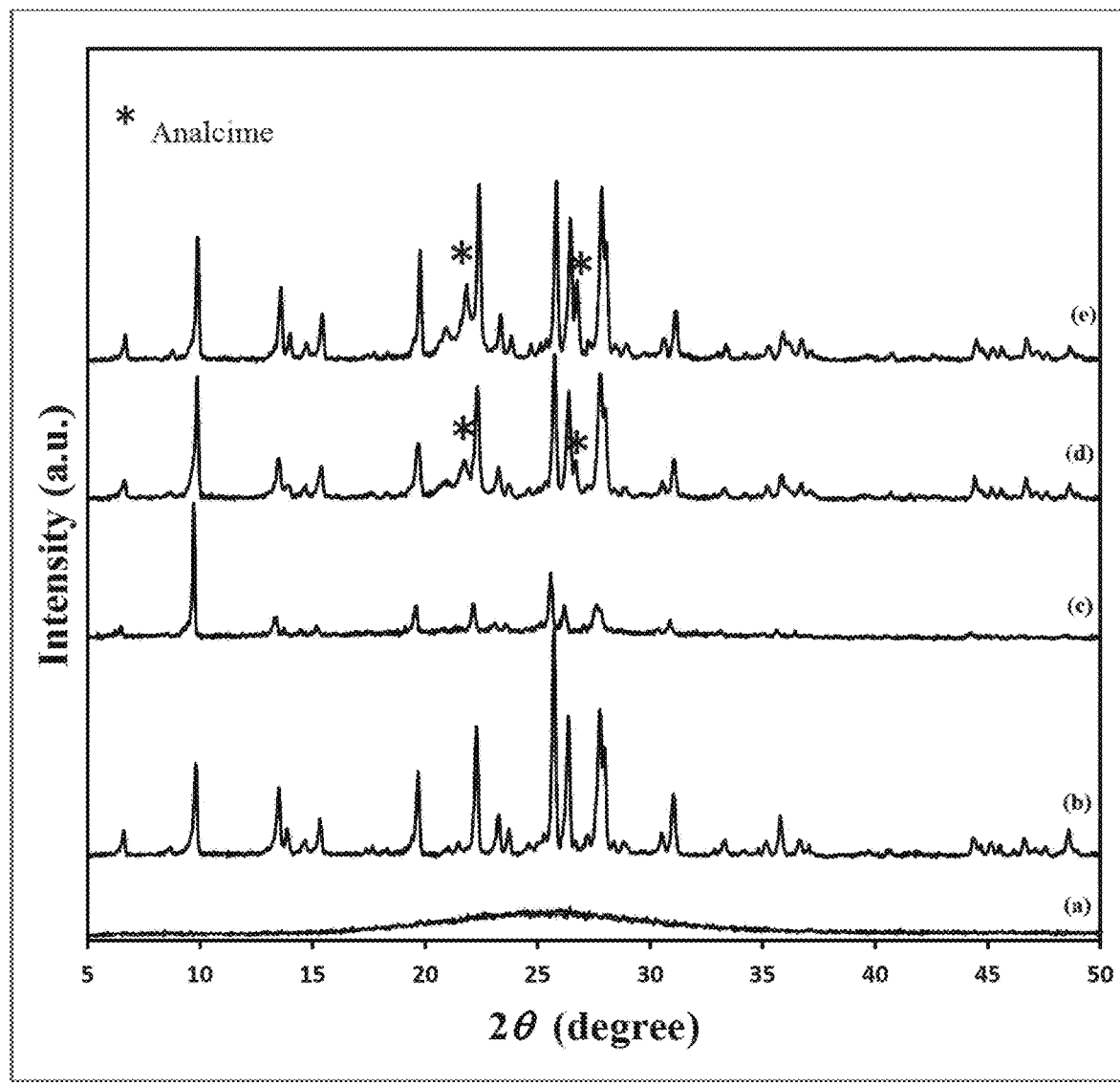
FIG. 10 is X-ray diffraction (XRD) patterns of mordenite zeolite synthesized at 180° C. for 48 h with different silica to alumina ratios including 10 (a), 15 (b), 20 (c), 25 (d), and 30 (e).
Figure 11:
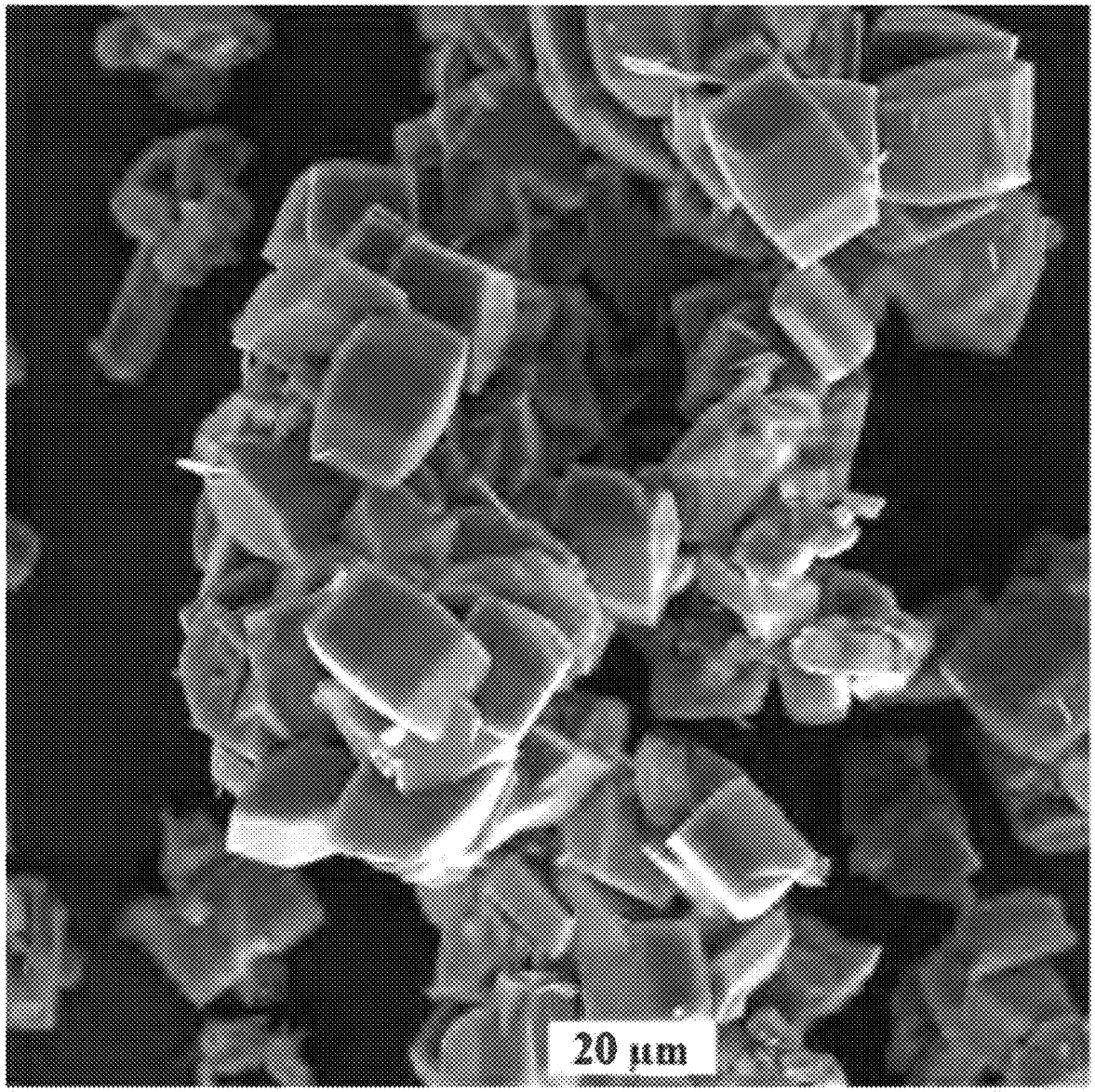
FIG. 11 is a scanning electron microscopy (SEM) micrograph of mordenite zeolite crystals with a silica to alumina ratio of 15.
Figure 12:
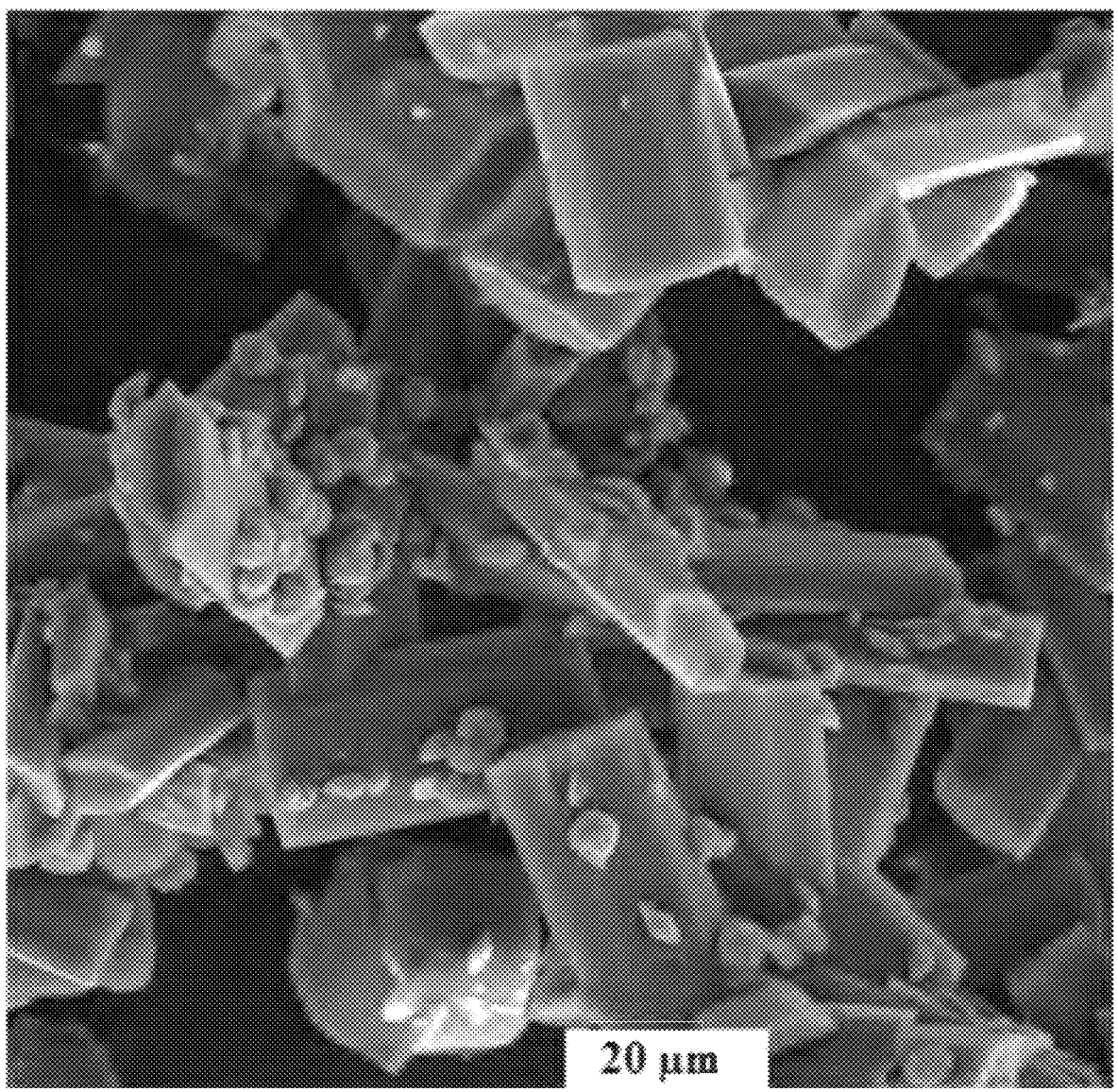
FIG. 12 is a scanning electron microscopy (SEM) micrograph of mordenite zeolite crystals with a silica to alumina ratio of 20.
Figure 13:
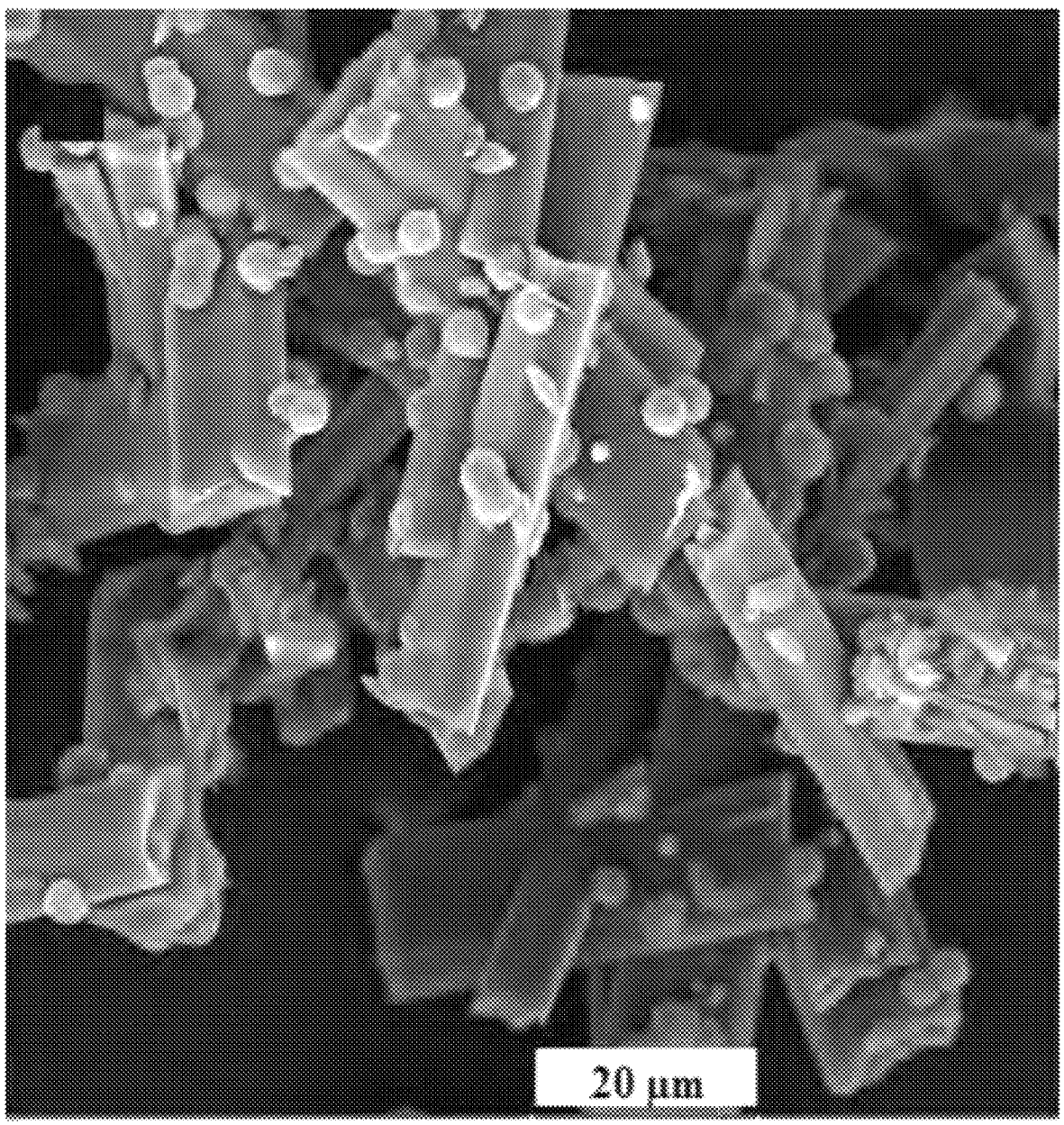
FIG. 13 is a scanning electron microscopy (SEM) micrograph of mordenite zeolite crystals with a silica to alumina ratio of 25.
Figure 14:
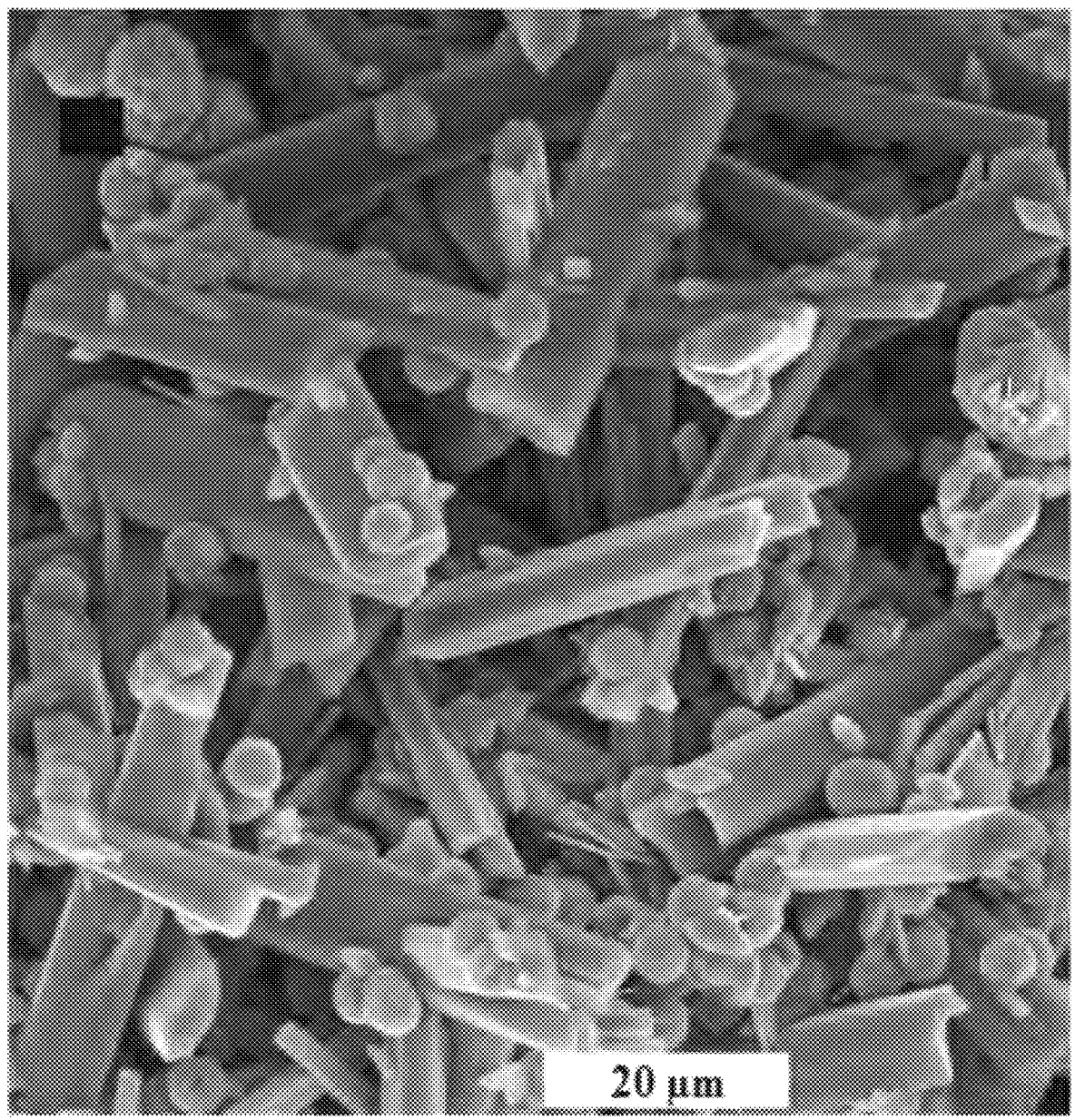
FIG. 14 is a scanning electron microscopy (SEM) micrograph of mordenite zeolite crystals with a silica to alumina ratio of 30.

Mordenite with different silica to alumina ratios was synthesized hydrothermally in the absence of organic template as previously described and investigated by X-ray diffraction (XRD). The XRD pattern is shown in FIG. 10. FIG. 10 shows the XRD patterns of samples synthesized with silica to alumina ratios in the range of 10-30, which reveals that an amorphous material was obtained for the sample with a silica to alumina ratio of 10 (a), while the rest gave crystalline materials. At higher silica to alumina ratios (greater than 20) (d) and (e) another phase, which was confirmed to be analcime was observed along with the mordenite crystal. The formation of analcime along with mordenite at higher silica to alumina ratios has been reported by Hincapie, et al. [Hincapie, B. O., et al., *Synthesis of mordenite nanocrystals*. Microporous and Mesoporous Materials, 2004. 67(1): p. 19-26.—incorporated herein by reference in its entirety]. It was also observed that the area of the XRD peaks for the prepared mordenite samples was higher than that of standard mordenite reported in the literature. This can be attributed to the high crystallinity of the prepared samples as can be confirmed from the size of the crystals obtained.

Several morphologies of this crystal have been synthesized in the literature, which includes; spherical, circular pie, flat prism, ellipsoidal, hexagonal star-like prism and the like [Mao, Y., et al., *Morphology-controlled synthesis of large mordenite crystals*. New Journal of Chemistry, 2014. 38(7): p. 3295-3301.—incorporated herein by reference in its entirety]. Scanning electron microscopy (SEM) micrographs of the prepared mordenite crystals are shown in FIG. 11, FIG. 12, FIG. 13, and FIG. 14. The SEM results reveal that a flat prism crystal was formed in the current work. The formation of the analcime growing phase at higher silica to alumina ratios was also confirmed by the SEM results. The relatively most pure form of mordenite was achieved with a silica to alumina ratio of 15 and it was adopted for the purpose of further study. It will subsequently be referred to as MOR-15.

Figure 15:
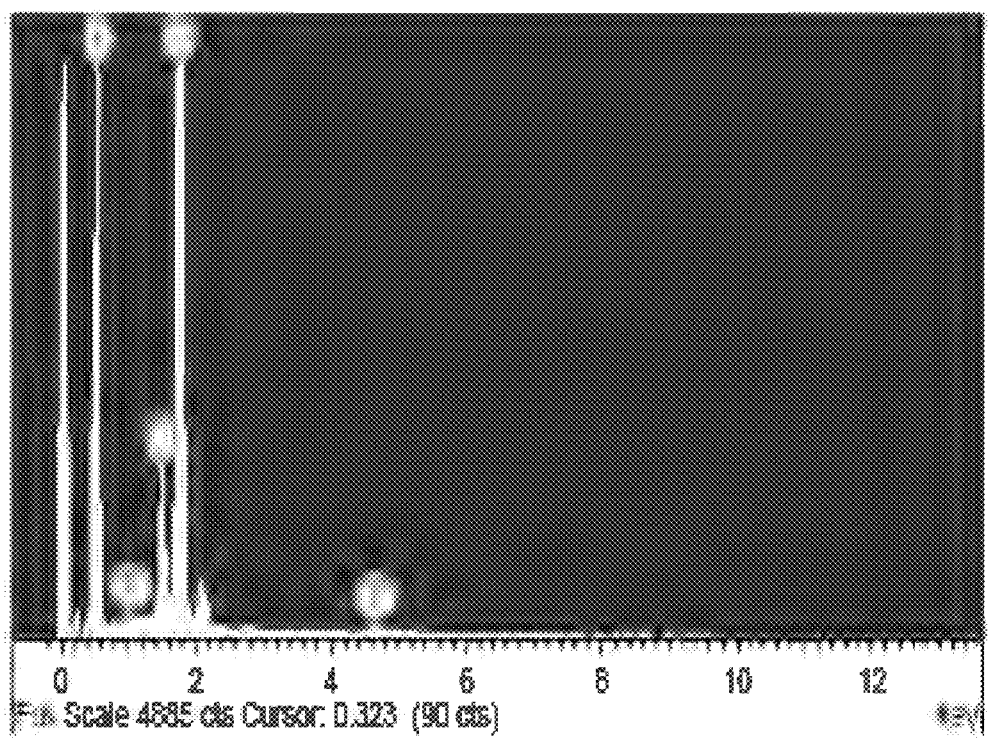
FIG. 15 is an energy dispersive X-ray (EDX) spectrum of a lanthanum impregnated mordenite zeolite (La-MOR-15).
Figure 16:
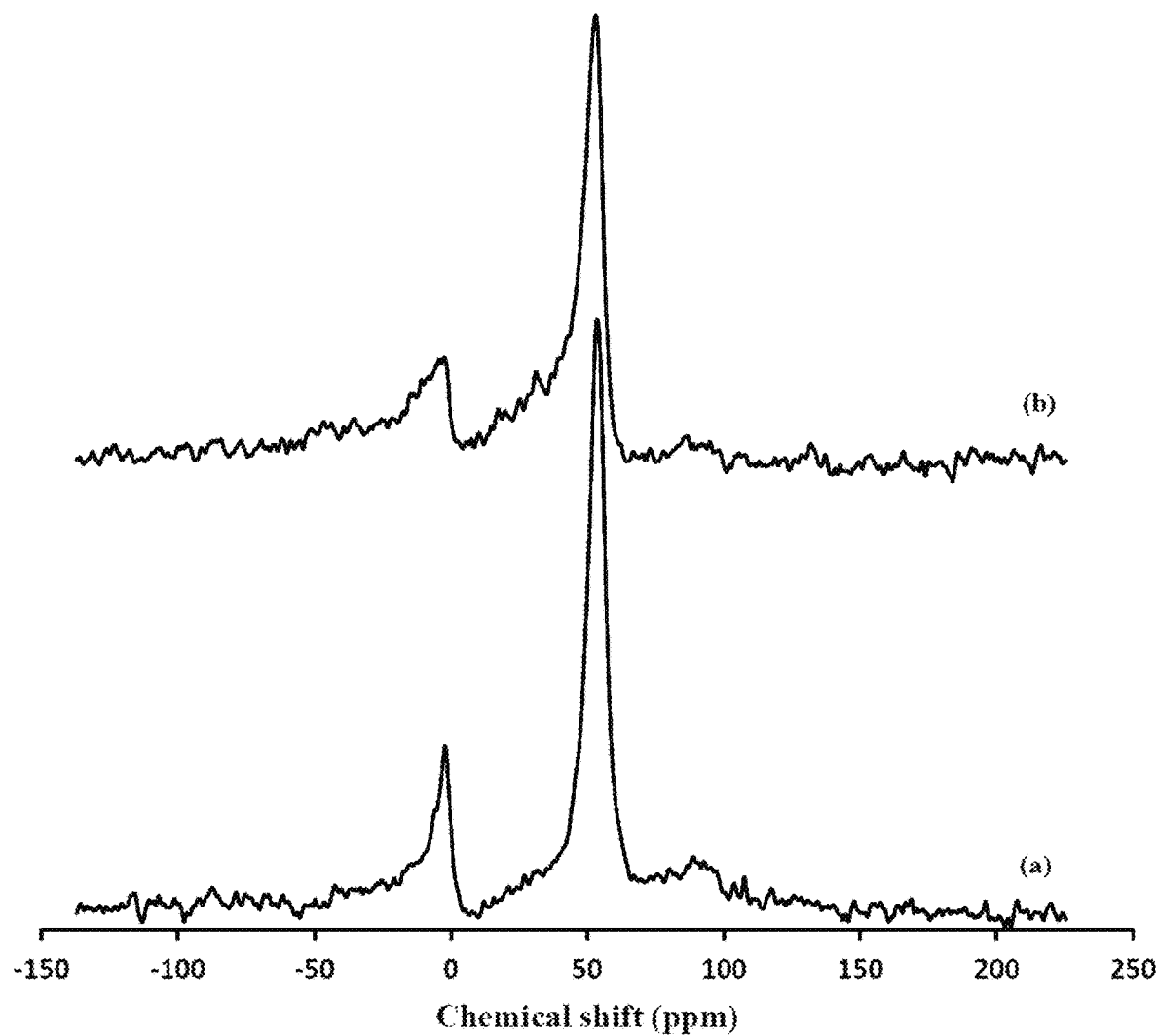
FIG. 16 is $^{27}$Al magic angle spinning nuclear magnetic resonance (MAS NMR) spectra of a mordenite zeolite (MOR-15) before rare earth metal impregnation (a) and after lanthanum (La) impregnation (b).

Following characterization of the MOR-15 mordenite zeolite, it was impregnated with 2 wt % lanthanum (La) and energy dispersive X-ray (EDX) spectroscopy was performed. The EDX results (Table 3 and FIG. 15) show that an average of 1.68 wt/o of the metal exists on the surface of the zeolite. The incorporation of La into the framework of the zeolite was also supported by $^{27}Al$ magic angle spinning nuclear magnetic resonance (MAS NMR, FIG. 16), which shows two distinct peaks at approximately 50 ppm and 0 ppm. The peak near 50 ppm could be assigned to the tetrahedral coordinated framework of Al atoms, while the peak at around 0 ppm is due to the octahedral coordinated extra framework [Barras, J., J. Klinowski, and D. W. McComb, *27Al and 29Si solid-state NMR studies of dealuminated mordenite*. Journal of the Chemical Society, Faraday Transactions, 1994. 90(24): p. 3719-3723.—incorporated herein by reference in its entirety]. FIG. 15 shows that the intensity of the peak corresponding to the tetrahedral coordinated Al atoms (50 ppm) decreases after La impregnation (b). This implies that some of the Al atoms have been replaced by La in the framework of the zeolite. This lanthanum metal impregnated zeolite will henceforth be denoted as La-MOR-15.

TABLE 3

Energy dispersive X-ray (EDX) results for La-MOR-15

| Spectrum | Oxygen (wt %) | Aluminum (wt %) | Silicon (wt %) | Lanthanum (wt %) | Total (wt %) |
|---|---|---|---|---|---|
| Mean | 56.48 | 4.39 | 37.45 | 1.68 | 100 |

Example 4

Electrochemical Characterization of a Prepared Lanthanum Impregnated Zeolite Modified Carbon Paste Electrode (La-ZMCPE)

Figure 17:
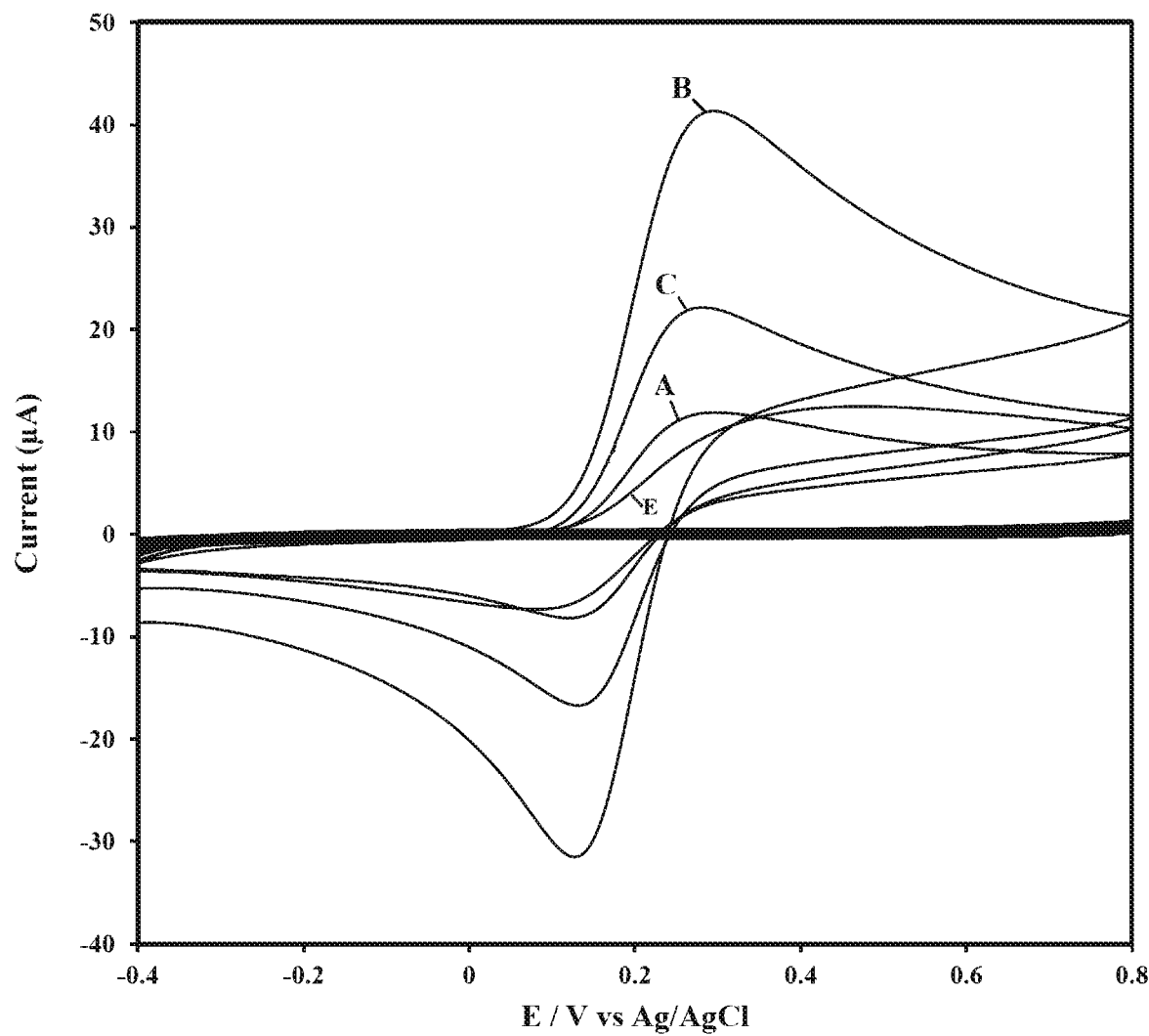
FIG. 17 is cyclic voltammetry (CV) voltammograms for a 10 mM K$_4$Fe(CN)$_6$ solution and 0.1 M KCl at a scan rate of 100 mV s$^{-1}$ (pH=7) at La-MOR-15 composites with the graphite:zeolite:paraffin ratio of 70:0:30 (A), 65:5:30 (B), 60:10:30 (C), and 50:20:30 (E).
Figure 18:
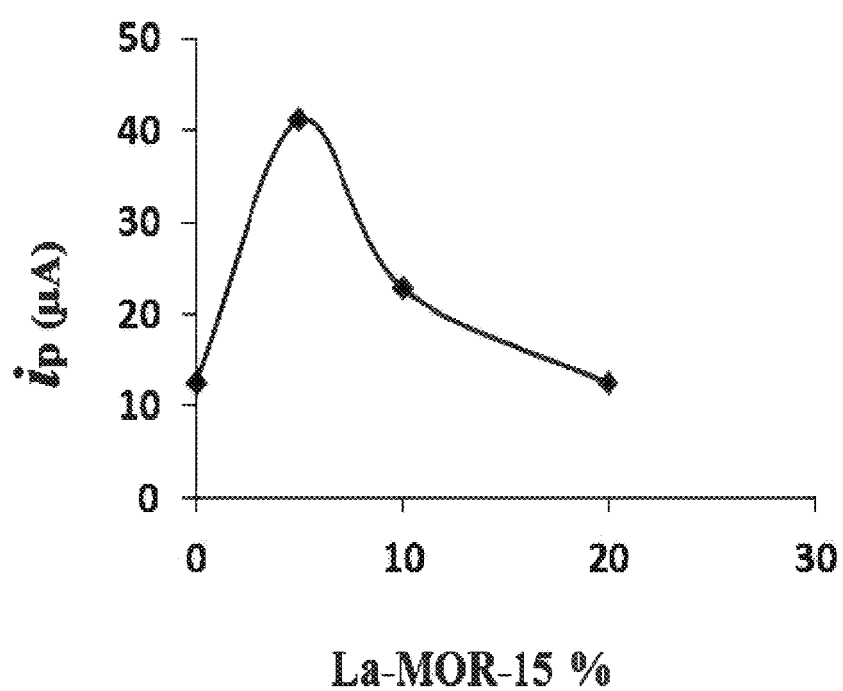
FIG. 18 is a plot of peak current for La-MOR-15 composites versus La-MOR-15 content percentage for zeolite modified carbon paste electrodes.

Cyclic voltammetry was employed for the investigation of the electrochemical properties of the zeolite modified carbon paste electrode (ZMCPE) synthesized as previously described where 10 mM potassium ferrocyanide ($K_4Fe(CN)_6$) and 0.1 M KCl were used as the electroactive specie and the supporting electrolyte, respectively. The La-impregnated zeolite (La-MOR-15, La-ZMCPE) and the unmodified zeolite (MOR-15, ZMCPE) were mixed separately with carbon graphite and paraffin oil in the ratios shown in Table 4 to obtain five composite electrodes (A, B, C, D, and E). The resulting homogeneous paste was packed into the tip of a micropipette and cyclic voltammetry was carried out in potassium ferrocyanide. The cyclic voltammograms show that composite electrode (B) with the ratio 65:5:30 (graphite: zeolite:paraffin) has the highest anodic peak current as show in FIG. 17. FIG. 18 is a plot of peak current versus the La-MOR percentage.

TABLE 4

Composite ratio of prepared zeolite modified carbon paste electrodes

| Designation | Graphite (wt %) | Zeolite (wt %) | Paraffin (wt %) |
|---|---|---|---|
| A | 70 | 0 | 30 |
| B | 65 | 5 | 30 |
| C | 60 | 10 | 30 |
| D | 55 | 15 | 30 |
| E | 50 | 20 | 30 |

The obtained results demonstrated reproducible anodic and cathodic peaks ascribed to $Fe(CN)_6^{3-}/Fe(CN)_6^{4-}$ redox couples at the surface of the zeolite modified carbon paste electrode. This was confirmed to be a quasi-reversible system that showed a peak separation potential ($\Delta Ep=Ep_a-Ep_c$) equal to 163 mV (0.294-0.131) which is greater than the 59 mV often seen for reversible systems [Hassaninejad-Darzi, S. and M. Rahimnejad, *Electrocatalytic oxidation of methanol by ZSM-5 nanozeolite-modified carbon paste electrode in alkaline medium*. Journal of the Iranian Chemical Society, 2014. 11(4): p. 1047-1056.—incorporated herein by reference in its entirety].

Figure 19:
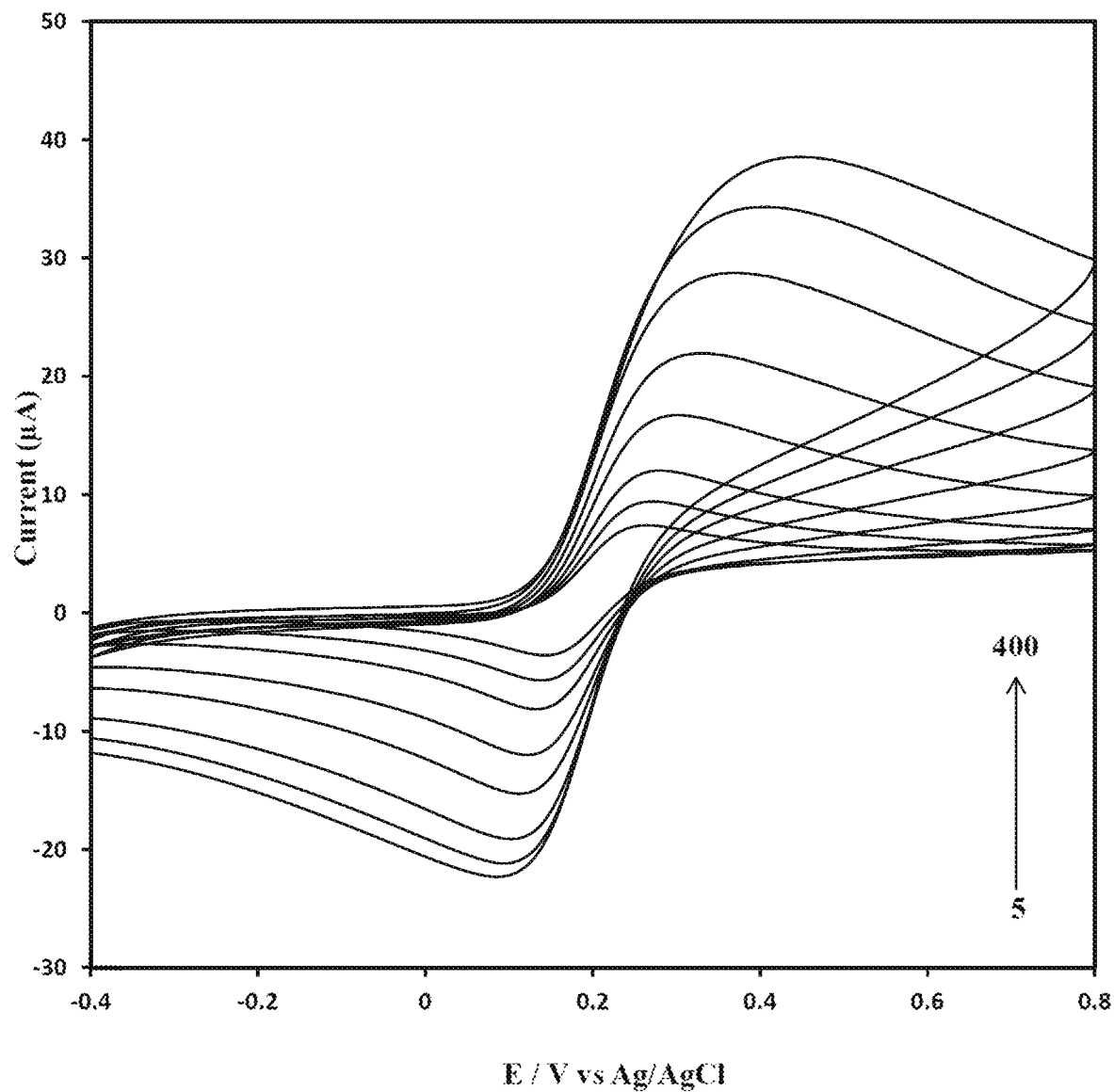
FIG. 19 illustrates the effect of scan rate (5-400 mV s$^{-1}$) on the peak current of a La-MOR-15 composite B electrode with the graphite:zeolite:paraffin ratio of 65:5:30 in the presence of 10 mM $K_4Fe(CN)_6$ solution and 0.1 M KCl (pH=7).
Figure 20:
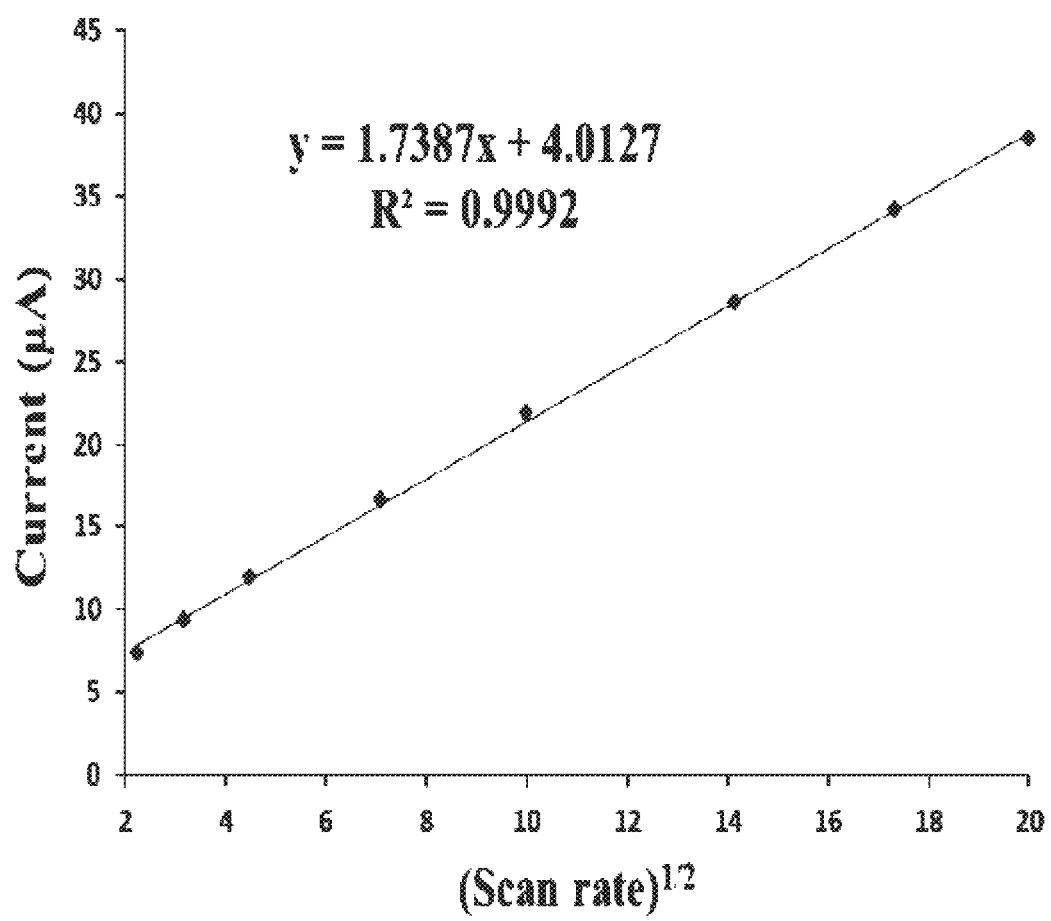
FIG. 20 is a plot of the peak current for the La-MOR-15 composite B electrode with the graphite:zeolite:paraffin ratio of 65:5:30 versus the square root of the scan rate.
Figure 21:
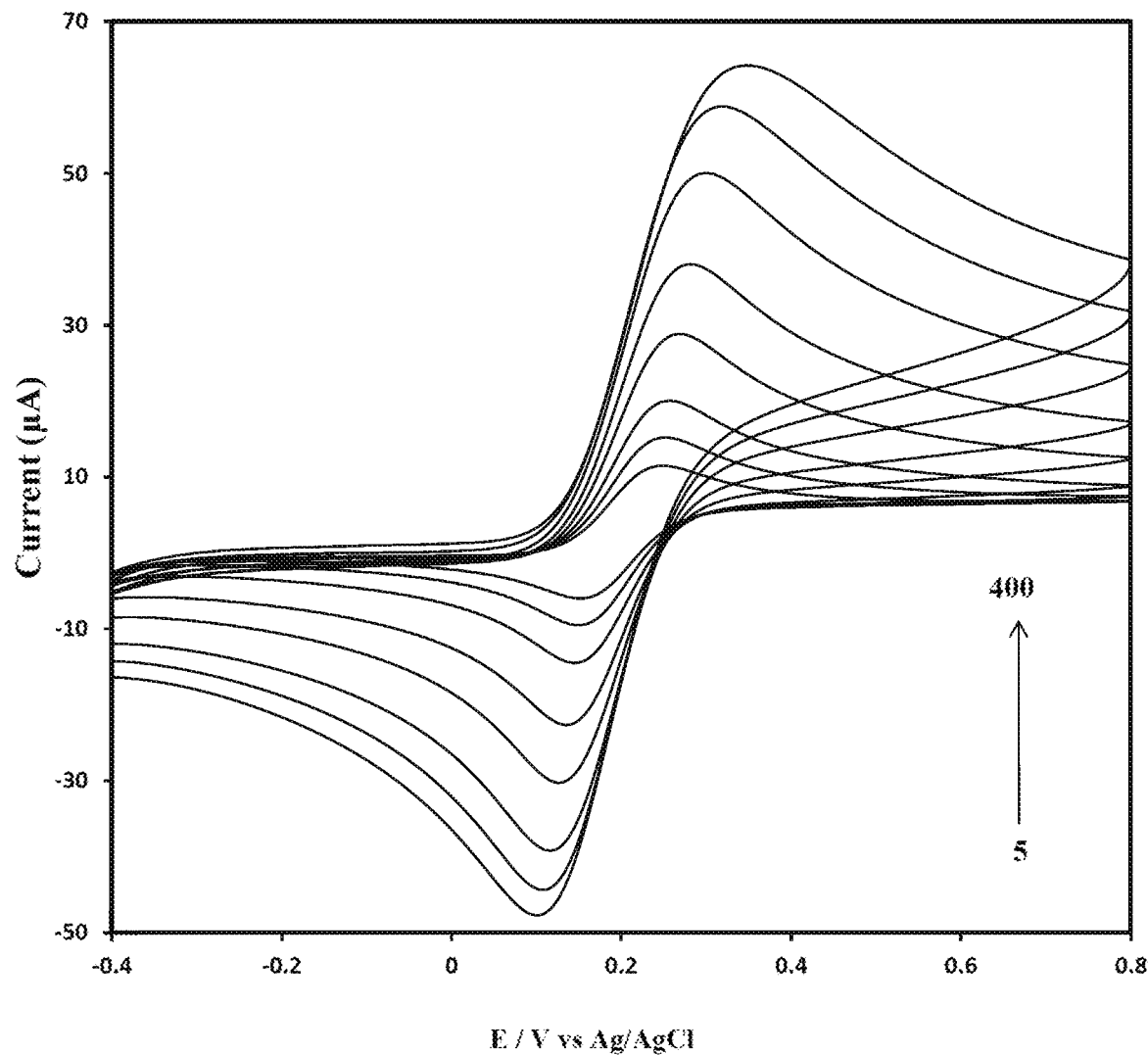
FIG. 21 illustrates the effect of scan rate (5-400 mV s$^{-1}$) on the peak current of a La-MOR-15 composite A electrode with the graphite:zeolite:paraffin ratio of 70:0:30 in the presence of 10 mM $K_4Fe(CN)_6$ solution and 0.1 M KCl (pH=7).
Figure 22:
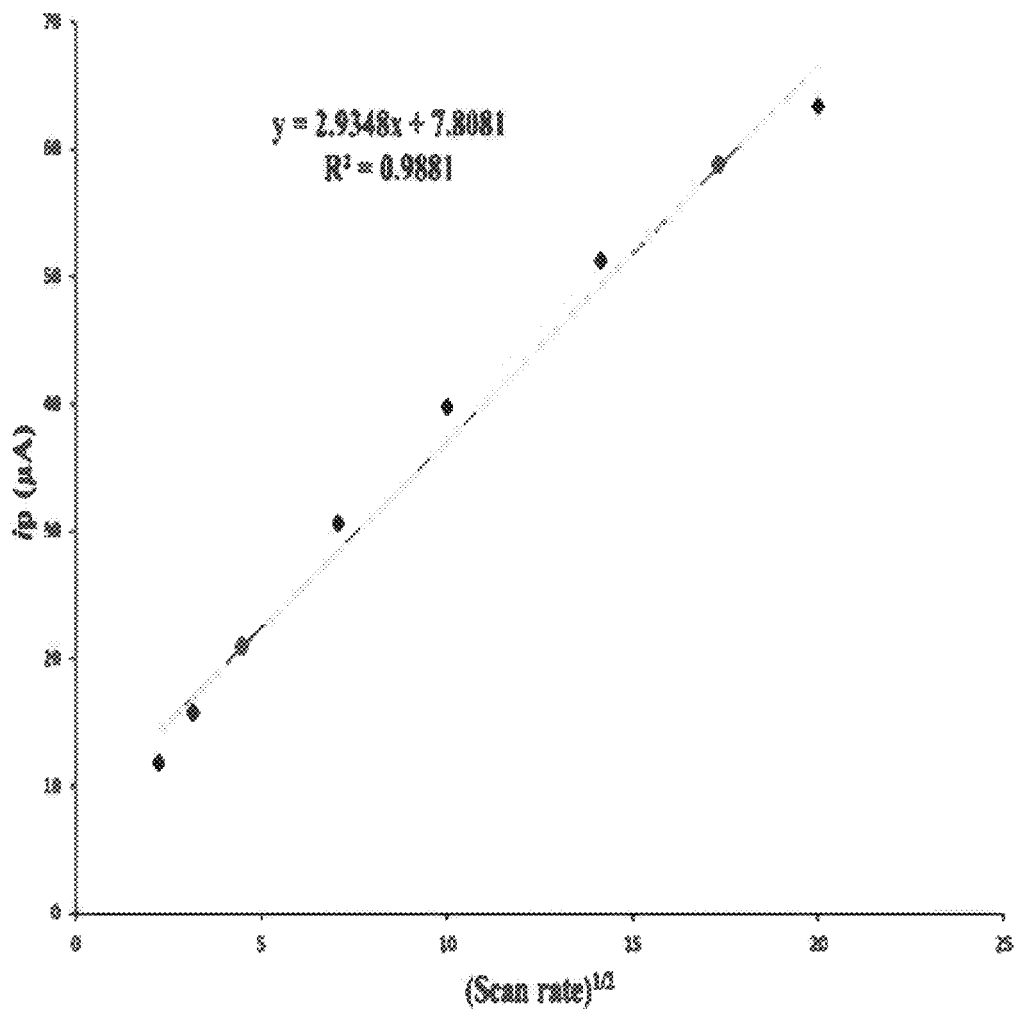
FIG. 22 is a plot of the peak current for the La-MOR-15 composite A electrode with the graphite:zeolite:paraffin ratio of 70:0:30 versus the square root of the scan rate.

In order to determine the electroactive surface area of the composite electrodes, the scan rate was varied from 5 to 400 mV s$^{-1}$ for both the bare carbon paste (composite A) and the La-MOR-15 electrodes. FIG. 19 shows the effect of scan rate on peak current for composite B. An approximately linear relationship was found between the anodic peak current and the square root of the scan rate ($R^2=0.9992$) for composite B. FIG. 20 shows a plot of peak current versus the square root of the scan rate for composite B. FIG. 21 shows the effect of scan rate on peak current for composite A. In contrast, a less linear relationship is obtained between the anodic peak current and the square root of scan rate ($R^2=0.9881$). FIG. 22 shows a plot of peak current versus the square root of the scan rate for composite A. It can be concluded from such a relationship that ion accessibility to electrode surface is enhanced by rare earth metal, such as lanthanum, impregnation.

The electroactive surface area of the composite electrodes was estimated from the slope of plots of peak current versus the square root of scan rate using the Randles-Sevcik equation as given by formula (II)

$$i_p = (2.69 \times 10^5) n^{3/2} A D^{1/2} v^{1/2} C \qquad (II):$$

In this equation, n is the number of electrons, v is the scan rate, D is the diffusion coefficient (cm² s⁻¹) of the electroactive species, A is the area of the working electrode, and C is the electrolyte concentration in mol L⁻¹. The electroactive surface area estimated for the composite electrodes are 21.4 mm² and 25.9 mm² for composites A and B, respectively. It can be concluded that modifying the carbon paste electrode with a lanthanum impregnated zeolite (i.e. La-MOR-15) leads to an increase in the electroactive surface area of the electrode.

Example 5

Voltammetric Determination of Cd(II) at a Prepared Lanthanum Impregnated Zeolite Modified Carbon Paste Electrode (La-ZMCPE)

The electrode of composite B as previously described (i.e. La-MOR-15 composite electrode with a graphite:zeolite:paraffin ratio of 65:5:30) was applied to the determination of Cd(II) ions in 0.1 M phosphate buffer (pH=4) using square wave anodic stripping voltammetry with constant stirring at 600 rpm during the accumulation of the analyte. Accumulation parameters such as accumulation potential and accumulation time were evaluated before carrying out the Cd determination.

Accumulation potential and accumulation time are crucial parameters when carrying out an anodic stripping voltammetric determination of metal ions such as the Cd(II) ion. This is because unless an appropriate potential is applied to enable the reduction and pre-concentration of the metal ions onto the surface of the working electrode prior to stripping, the sensitivity of the electrode is greatly affected. The effect of accumulation potential was studied by Kokkinos, et al. [Kokkinos, C., et al., *Lithographically fabricated disposable bismuth-film electrodes for the trace determination of Pb(II) and Cd(II) by anodic stripping voltammetry*. Electrochimica Acta, 2008. 53(16): p. 5294-5299.—incorporated herein by reference in its entirety]. This study demonstrated that choosing a high potential (in the negative direction) leads to background hydrogen evolution. In addition, an accumulation potential which is too low is insufficient to reduce the metal onto the surface of the electrode before being stripped.

Figure 23:
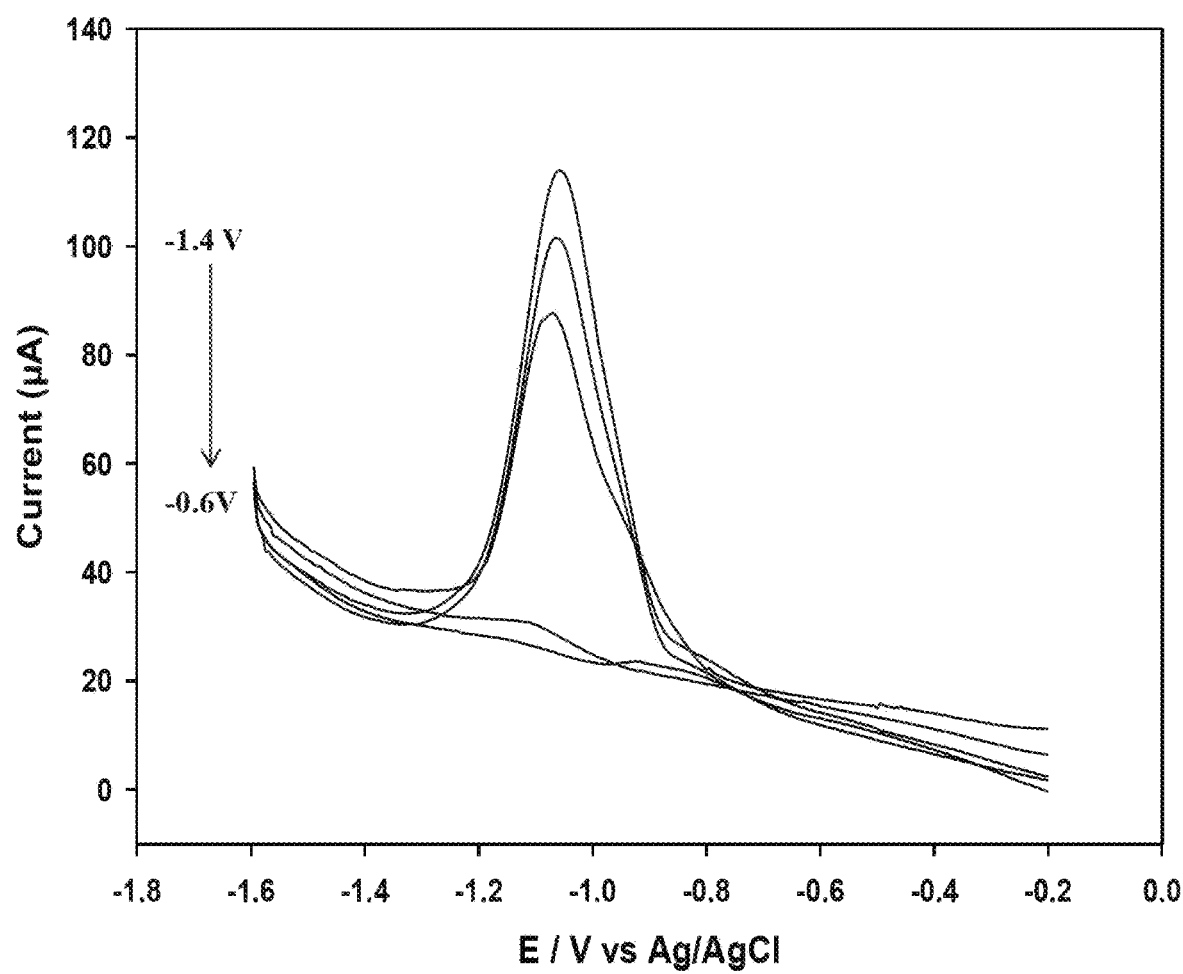
FIG. 23 illustrates the effect of varying accumulation potential (−1.4 V to −0.6 V) on the square wave anodic stripping voltammetry (SWASV) voltammograms of 500 ppb Cd(II) in 0.1 M phosphate buffer (pH=4) at a La-MOR-15 composite B zeolite modified carbon paste electrode with the graphite:zeolite:paraffin ratio of 65:5:30 at an accumulation time of 120 seconds, an amplitude of 0.2 V, a frequency of 40 Hz, and a potential step of 5 mV.
Figure 24:
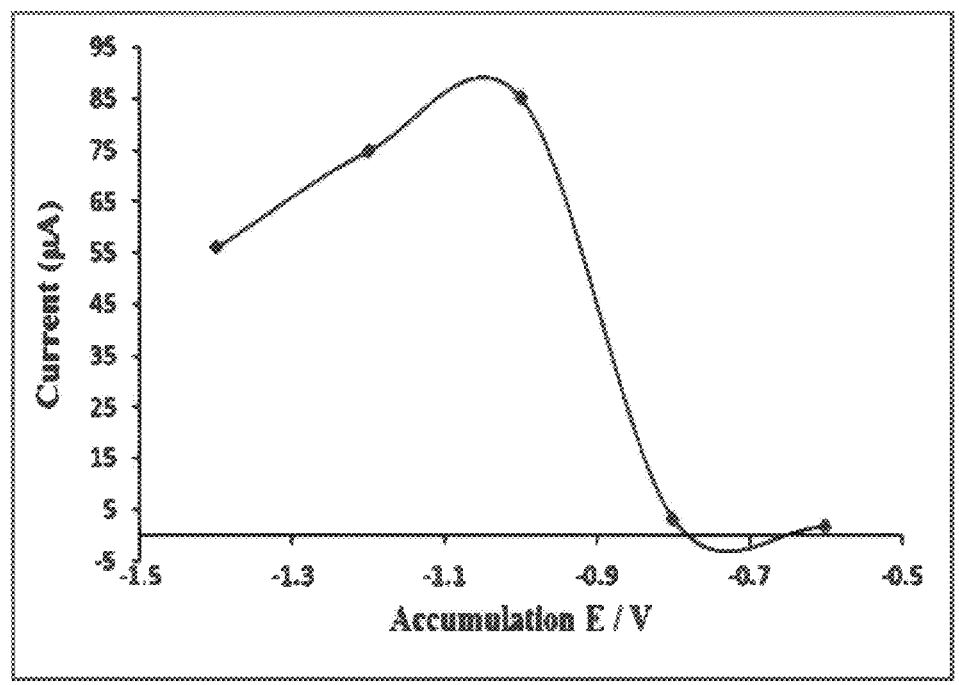
FIG. 24 is a plot of the current for a La-MOR-15 composite B zeolite modified carbon paste electrode with the graphite:zeolite:paraffin ratio of 65:5:30 versus accumulation potential.

For the current procedure, evaluation was carried out in a 500 ppb Cd(II) solution in 0.1 M phosphate buffer (pH=4) and the accumulation potential was varied from −1.4 V to −0.6 V. FIG. 23 presents the resulting square wave voltammograms. FIG. 24 presents the plot of current versus accumulation potential and it can be seen that the maximum peak current is obtained at −1.0 V. However, when this value was adopted for subsequent detection along with other parameters such as amplitude (0.2 V) and frequency (40 Hz), a very broad peak was obtained. Hence, a balance was necessary between obtaining a maximum peak current and a less broad peak. As such, an accumulation potential of −1.2 V was adopted for the purposes of the current procedure.

Figure 25:
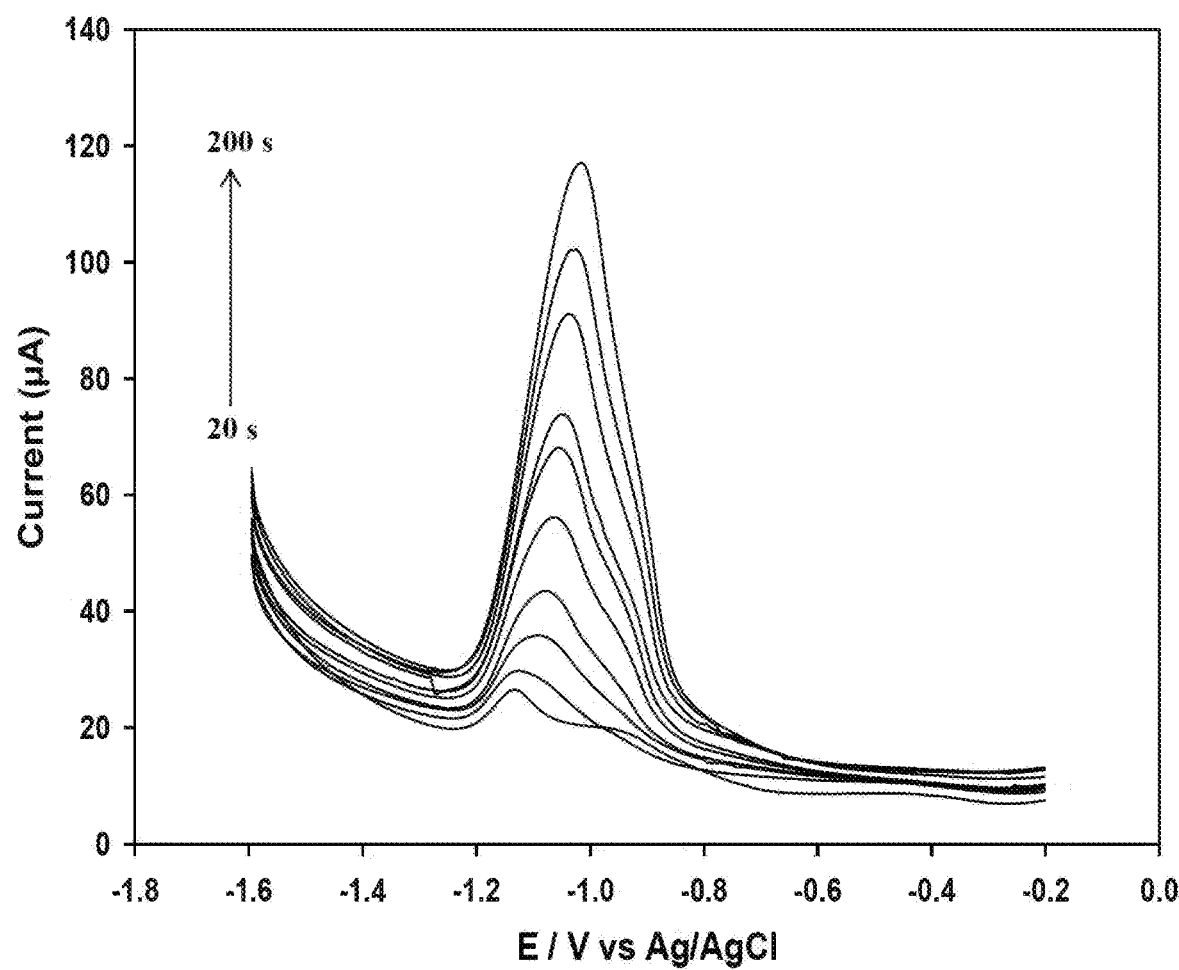
FIG. 25 illustrates the effect of varying accumulation time (20-200 seconds) on the SWASV voltammograms of 500 ppb Cd(II) in 0.1 M phosphate buffer (pH=4) at a La-MOR-15 composite B zeolite modified carbon paste electrode with the graphite:zeolite:paraffin ratio of 65:5:30 at an accumulation potential of −1.2 V, an amplitude of 0.2 V, a frequency of 40 Hz, and a potential step of 5 mV.
Figure 26:
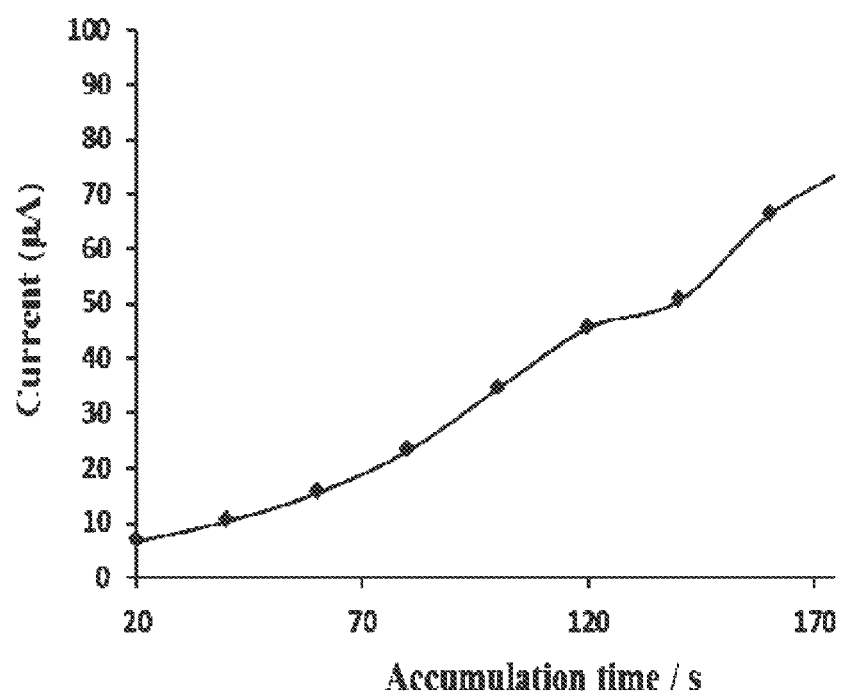
FIG. 26 is a plot of the current for a La-MOR-15 composite B zeolite modified carbon paste electrode with the graphite:zeolite:paraffin ratio of 65:5:30 versus accumulation time.

In a similar manner, the accumulation time was varied from 20 seconds to 200 seconds. FIG. 25 shows the results. FIG. 26 is a plot of current versus accumulation time. Accumulation time is the time during which the analyte is reduced at the working electrode (WE). It is generally believed that lower detection limits can be obtained with a longer accumulation time [Castaneda, M. T., et al., *Sensitive stripping voltammetry of heavy metals by using a composite sensor based on a built-in bismuth precursor*. Analyst, 2005. 130(6): p. 971-976.—incorporated herein by reference in its entirety]. However, a longer accumulation time can alter the electrode's surface thereby affecting its performance. As a result, an accumulation time of 120 seconds was adopted for the purposes of the current procedure. In summary, the following conditions were employed for the subsequent construction of a calibration curve for Cd(II) detection using the zeolite modified carbon paste electrode of composite B (i.e. 2%-La-MOR-15 composite electrode with a graphite:zeolite:paraffin ratio of 65:5:30) prepared in the current disclosure; amplitude: 0.2 V, frequency: 40 Hz, accumulation potential: −1.2 V, accumulation time: 120 seconds, potential increment: 0.005 V.

Figure 27:
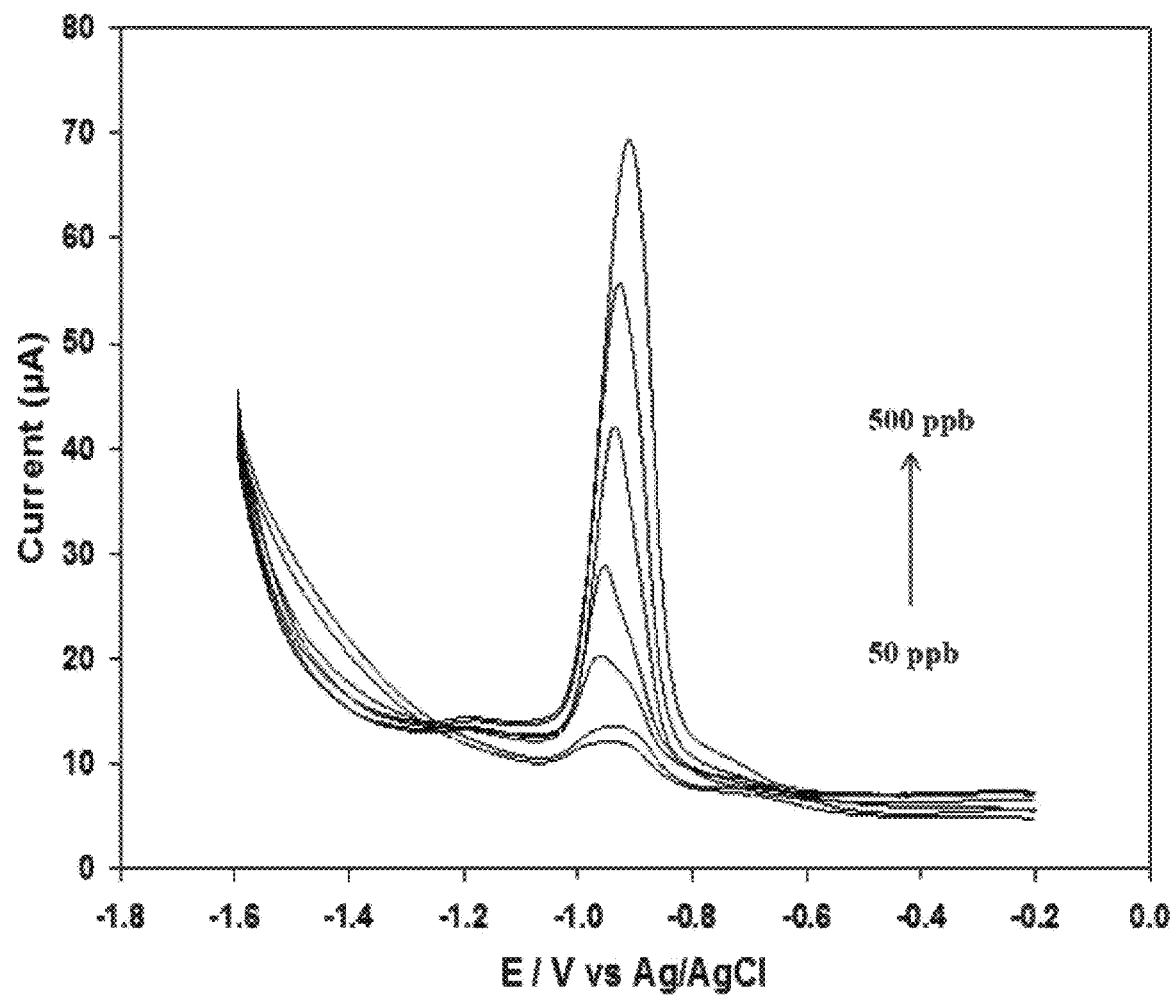
FIG. 27 illustrates the effect of varying Cd(II) concentration (50-500 ppb) on the SWASV voltammograms in 0.1 M phosphate buffer (pH=4) at a La-MOR-15 composite B zeolite modified carbon paste electrode with the graphite:zeolite:paraffin ratio of 65:5:30 at an accumulation potential of −1.2 V, an accumulation time of 120 seconds, an amplitude of 100 mV, a frequency of 40 Hz, and a potential step of 5 mV.
Figure 28:
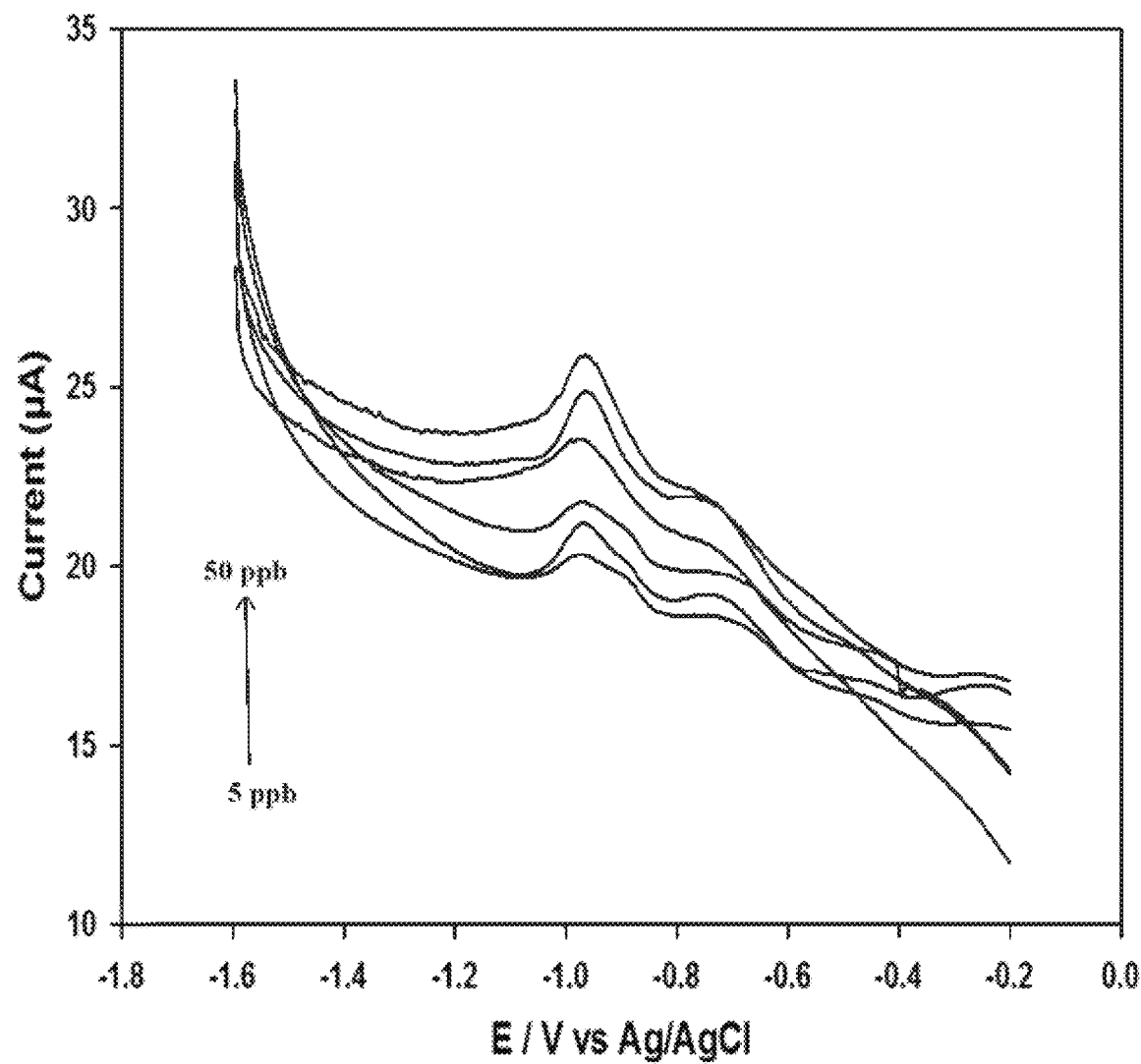
FIG. 28 illustrates the effect of varying Cd(II) concentration (5-50 ppb) on the SWASV voltammograms in 0.1 M phosphate buffer (pH=4) at a La-MOR-15 composite B zeolite modified carbon paste electrode with the graphite:zeolite:paraffin ratio of 65:5:30 at an accumulation potential of −1.2 V, an accumulation time of 120 seconds, an amplitude of 100 mV, a frequency of 40 Hz, and a potential step of 5 mV.
Figure 29:
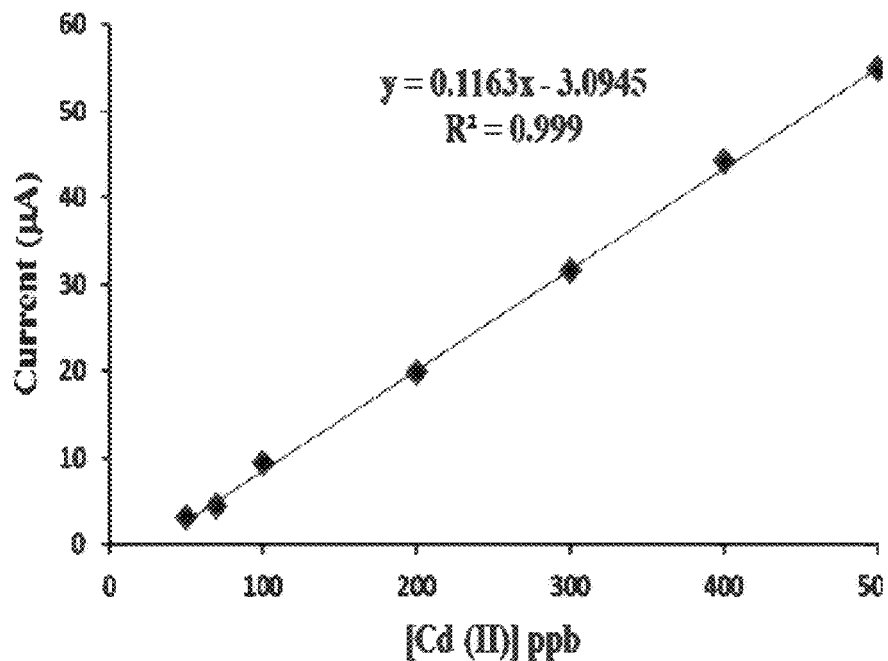
FIG. 29 is a calibration plot for a La-MOR-15 composite B zeolite modified carbon paste electrode with the graphite:zeolite:paraffin ratio of 65:5:30 of Cd(II) concentrations from 50-500 ppb.
Figure 30:
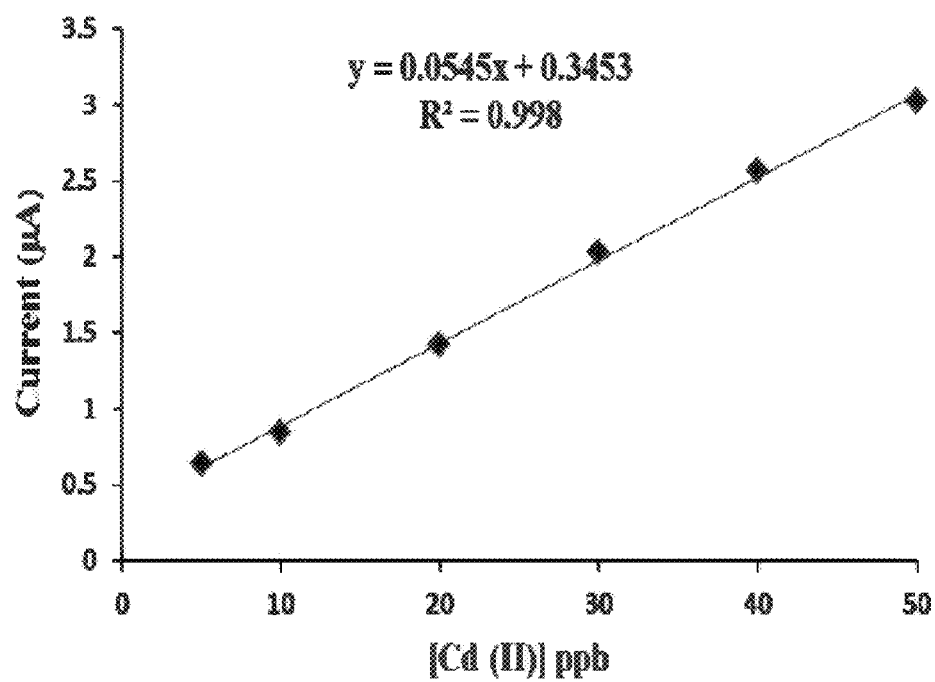
FIG. 30 is a calibration plot for a La-MOR-15 composite B zeolite modified carbon paste electrode with the graphite:zeolite:paraffin ratio of 65:5:30 of Cd(II) concentrations from 5-50 ppb.

After the evaluation of the different parameters, the stripping of Cd (II) over two different concentration ranges of 50-500 ppb (FIG. 27) and 5-50 ppb (FIG. 28) were investigated. FIG. 29 shows the obtained calibration plot of Cd(II) over the concentration range of 50-500 ppb. FIG. 30 shows the obtained calibration plot of Cd(II) over the concentration range of 5-50 ppb. The stripping current was found to be linear with various concentrations of Cd(II) at both higher and lower concentration ranges with correlation coefficients of 0.999 and 0.998 for the higher and lower concentration ranges, respectively. The limit of quantitation was found to be 5 µg/L and the limit of detection (S/N=3) was 0.12 µg/L. It can be concluded from the results of the analytical performance parameters that the lanthanum impregnated zeolite (i.e. La-MOR-15) modified carbon paste electrode constructed in the current disclosure has a wide determination range with a low detection limit.

Figure 31:
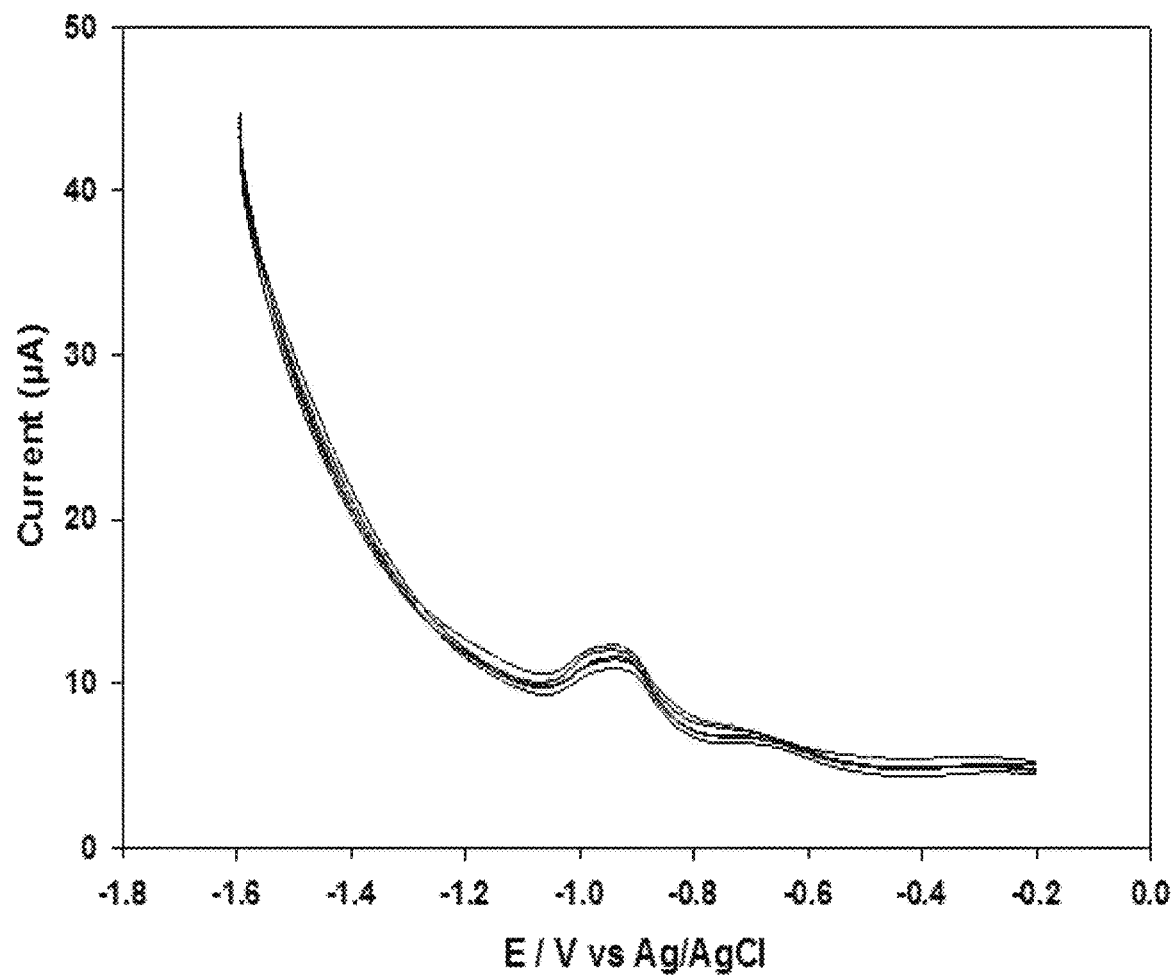
FIG. 31 illustrates SWASV voltammograms in 0.1 M phosphate buffer (pH=4) at a La-MOR-15 composite B zeolite modified carbon paste electrode with the graphite:zeolite:paraffin ratio of 65:5:30 at an accumulation potential of −1.2 V, an accumulation time of 120 seconds, an amplitude of 100 mV, a frequency of 40 Hz, and a potential step of 5 mV over 5 consecutive runs.

The performance parameters of the current lanthanum impregnated zeolite (i.e. La-MOR-15) modified carbon paste electrode compare favorably with other electrodes for the detection of Cd(II) that have been reported previously (Table 5) [Rico, M. Á. G., M. Olivares-Marin, and E. P. Gil, *Modification of carbon screenprinted electrodes by adsorption of chemically synthesized Bi nanoparticles for the voltammetric stripping detection of Zn(II), Cd(II) and Pb(II)*. Talanta, 2009. 80(2): p. 631-635; and El Tall, O., et al., *Anodic Stripping Voltammetry of Heavy Metals at Nanocrystalline Boron-Doped Diamond Electrode*. Electroanalysis, 2007. 19(11): p. 1152-1159; and Švancara, I., et al., *Recent Advances in Anodic Stripping Voltammetry with Bismuth-Modified Carbon Paste Electrodes*. Electroanalysis, 2006. 18(2): p. 177-185; and Siriangkhawut, W., et al., *Sequential injection monosegmented flow voltammetric determination of cadmium and lead using a bismuth film working electrode*. Talanta, 2009. 79(4): p. 1118-1124; and Kefala, G. and A. Economou, *Polymer-coated bismuth film electrodes for the determination of trace metals by sequential-injection analysis/anodic stripping voltammetry*. Analytica Chimica Acta, 2006. 576(2): p. 283-289; and Lee, G.-J., H.-M. Lee, and C.-K. Rhee, *Bismuth nano-powder electrode for trace analysis of heavy metals using anodic stripping voltammetry*. Electrochemistry Communications, 2007. 9(10): p. 2514-2518.—each incorporated herein by reference in its entirety]. The current electrode compares well and in fact has one of the lowest detection limits for Cd(II) detection. The reproducibility of the stripping analysis of 50 ppb Cd (II) at the lanthanum impregnated zeolite (i.e. La-MOR-15) modified carbon paste electrode was also examined by carrying out five consecutive measurements with a single electrode. The relative standard deviation (RSD) was found as 2.7% implying that electrode is stable with reproducible Cd (II) detection ability (FIG. 31).

TABLE 5

Detection limits and performance parameters of previously reported electrodes

| Electrode Type | Analyte | Technique | Accumulation Potential (V) | Accumulation Time (s) | Detection Limit (µg/L) | Ref. |
|---|---|---|---|---|---|---|
| Carbon screen printed electrode modified by Bi-nanoparticle | Cd(II) | SWASV | −1.4 | 120 | 1.3 | Rico, et al. |
| Boron-doped diamond electrode | Cd(II) | DPASV | −1.7 | 60 | 0.36 | El Tall, et al. |
| Bi-modified carbon paste electrode | Cd(II) | SWASV | −0.95 | 120 | 1.0 | Svancara, et al. |
| Bi-film electrode | Cd(II) | SWASV | −1.10 | 90 | 1.4 | Siriangkhawut, et al. |
| Nafion-coated Bi-film electrode | Cd(II) | SWASV | −1.4 | — | 2.0 | Kefala, et al. |
| Bi nano-powder electrode | Cd(II) | SWASV | −1.2 | 180 | 0.07 | Lee, et al. |

Example 6

Synthesis and Characterization of a Prepared Lanthanum or Cerium Impregnated Zeolite Modified Carbon Paste Electrode (La/Ce-ZMCPE)

Figure 32:
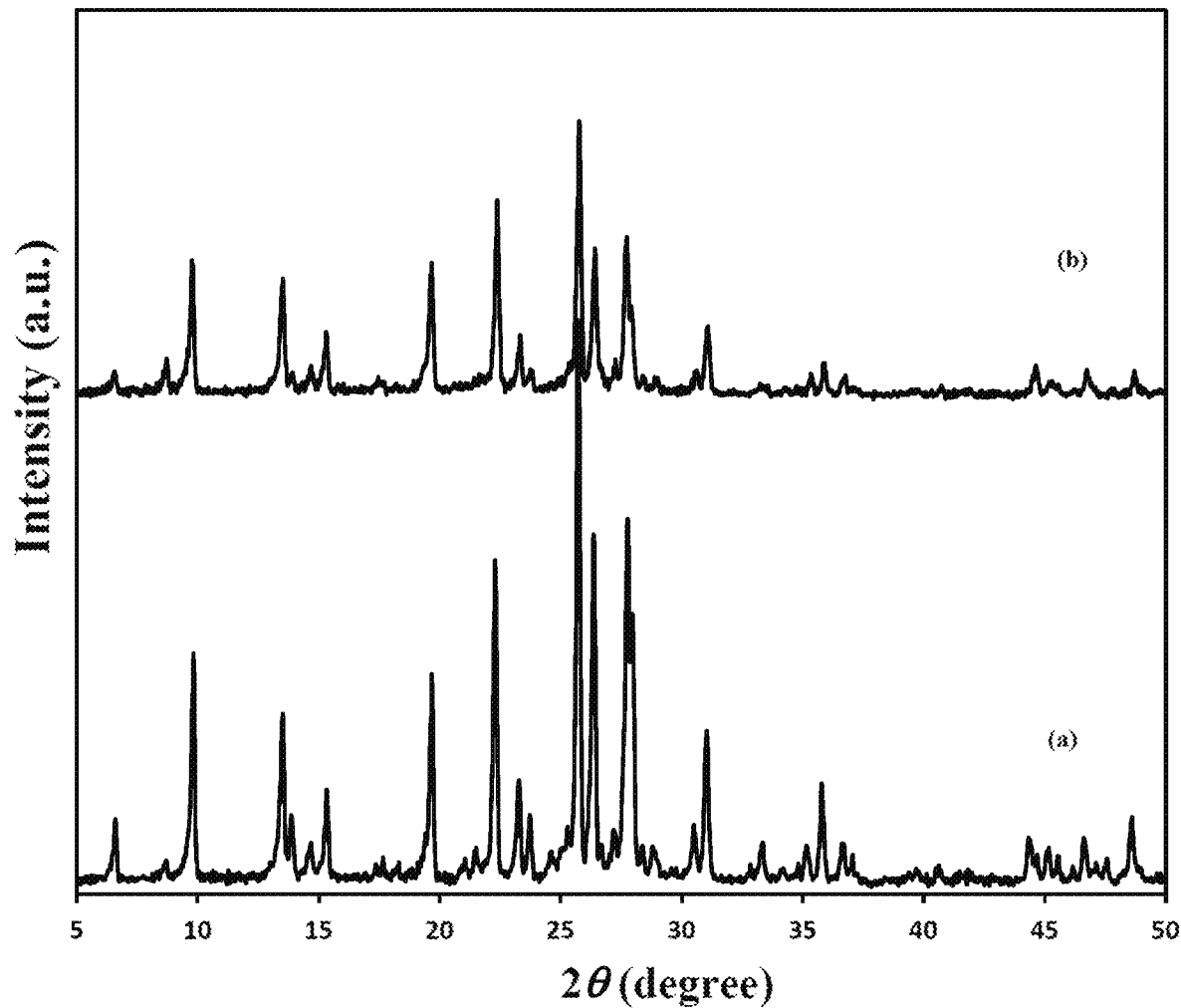
FIG. 32 is X-ray diffraction (XRD) patterns of the Na-MOR (a) and H-MOR (b) mordenite zeolite crystal forms with a silica to alumina ratio of 15 prior to and after ion exchange.
Figure 33:
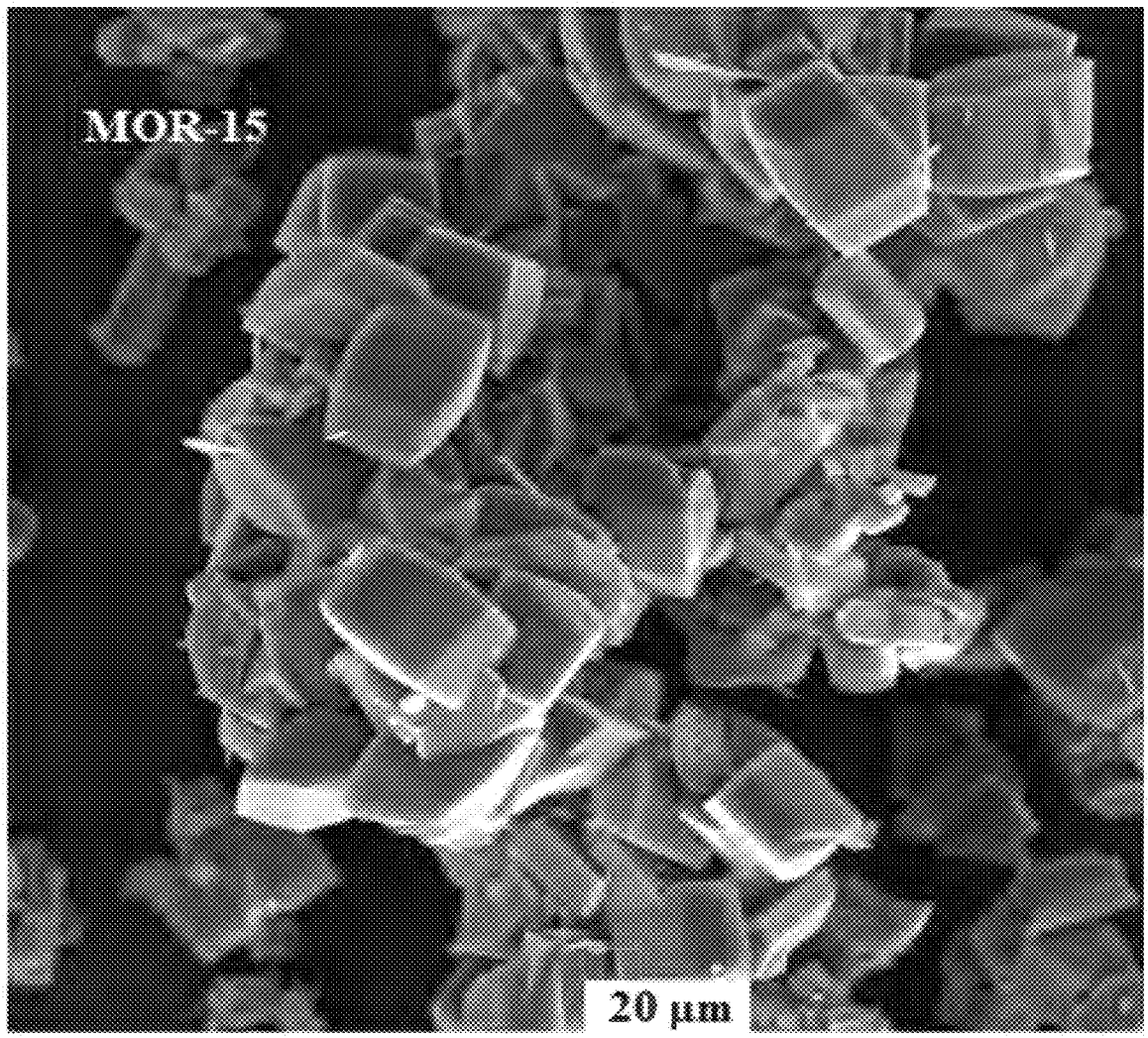
FIG. 33 is a scanning electron microscopy (SEM) micrograph of mordenite zeolite crystals with a silica to alumina ratio of 15 (MOR-15).

Mordenite zeolite with a silica to alumina ratio of 15 was synthesized by the sol-gel method. The resulting crystal was investigated by X-ray diffraction (XRD) spectroscopy in order to ascertain its crystallinity. FIG. 32 shows the result of the XRD and presents the Na (a) and H (b) forms of the crystal prior to and after ion exchange, with diffraction peaks corresponding to the typical structure of mordenite [Mohamed, M. M., et al., *Synthesis of high silica mordenite nanocrystals using ophenylenediamine template*. Microporous and Mesoporous Materials, 2005. 84(1-3): p. 84-96.— incorporated herein by reference in its entirety]. The average crystal size of the synthesized material was obtained using the Scherer equation and found as 6.8 µm [Edwards, A. J., H. P. Klug and L. E. Alexander, *x-ray diffraction procedures for polycrystalline and amorphous materials*: Wiley-Interscience, New York $2^{nd}$ edn., 1974, xxv+966 pp. price £ 18.55. Analytica Chimica Acta, 1975. 77(0): p. 349.— incorporated herein by reference in its entirety]. The size of crystals obtained using the Scherer equation is usually interpreted as an average crystal dimension, perpendicular to the reflection plane, the accuracy of which is usually no better than 20-40% because the sample being analyzed usually does not have crystals of uniform size [Bor, T. C., et al., *Simulation of X-ray diffraction-line broadening due to dislocations in a model composite material*. Materials Science and Engineering: A, 2001. 309-310(0): p. 505-509.— incorporated herein by reference in its entirety]. The morphology of the mordenite indicates that a flat prism crystal was formed as shown in the scanning electron microscopy (SEM) image in FIG. 33.

Figure 34:
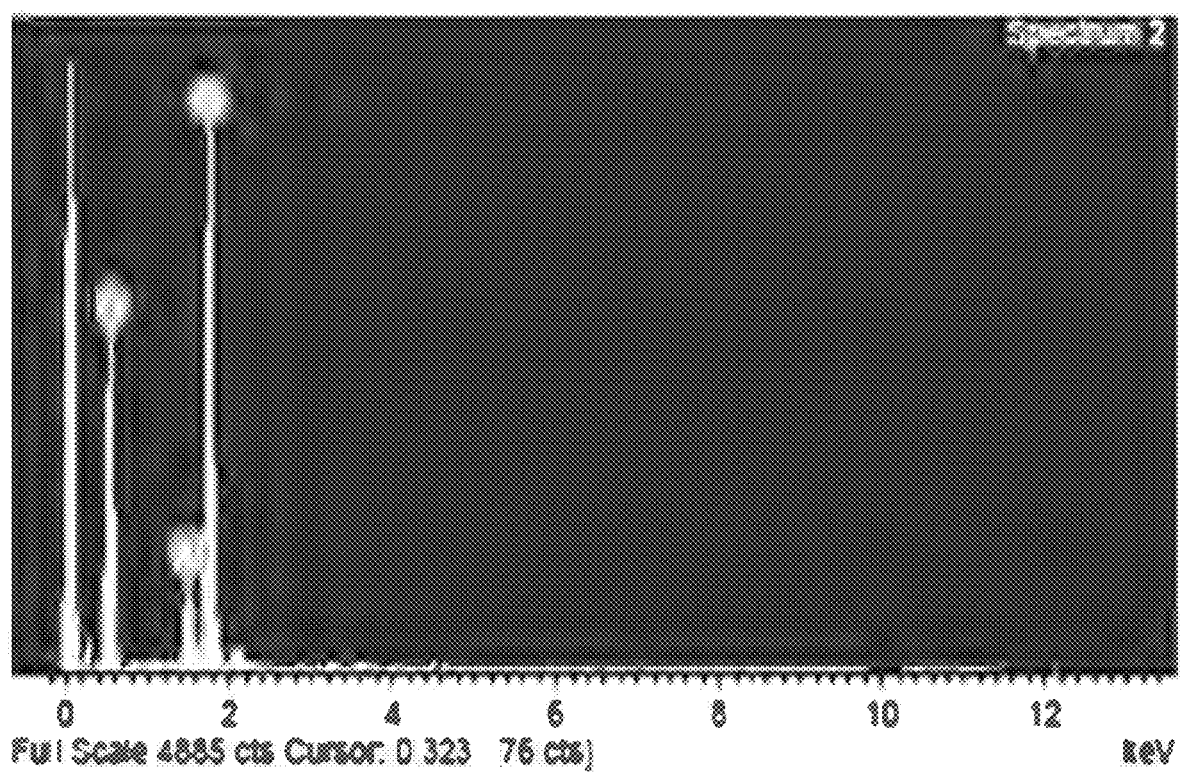
FIG. 34 is an energy dispersive X-ray (EDX) spectrum of mordenite zeolite with a silica to alumina ratio of 15 (MOR-15).
Figure 35:
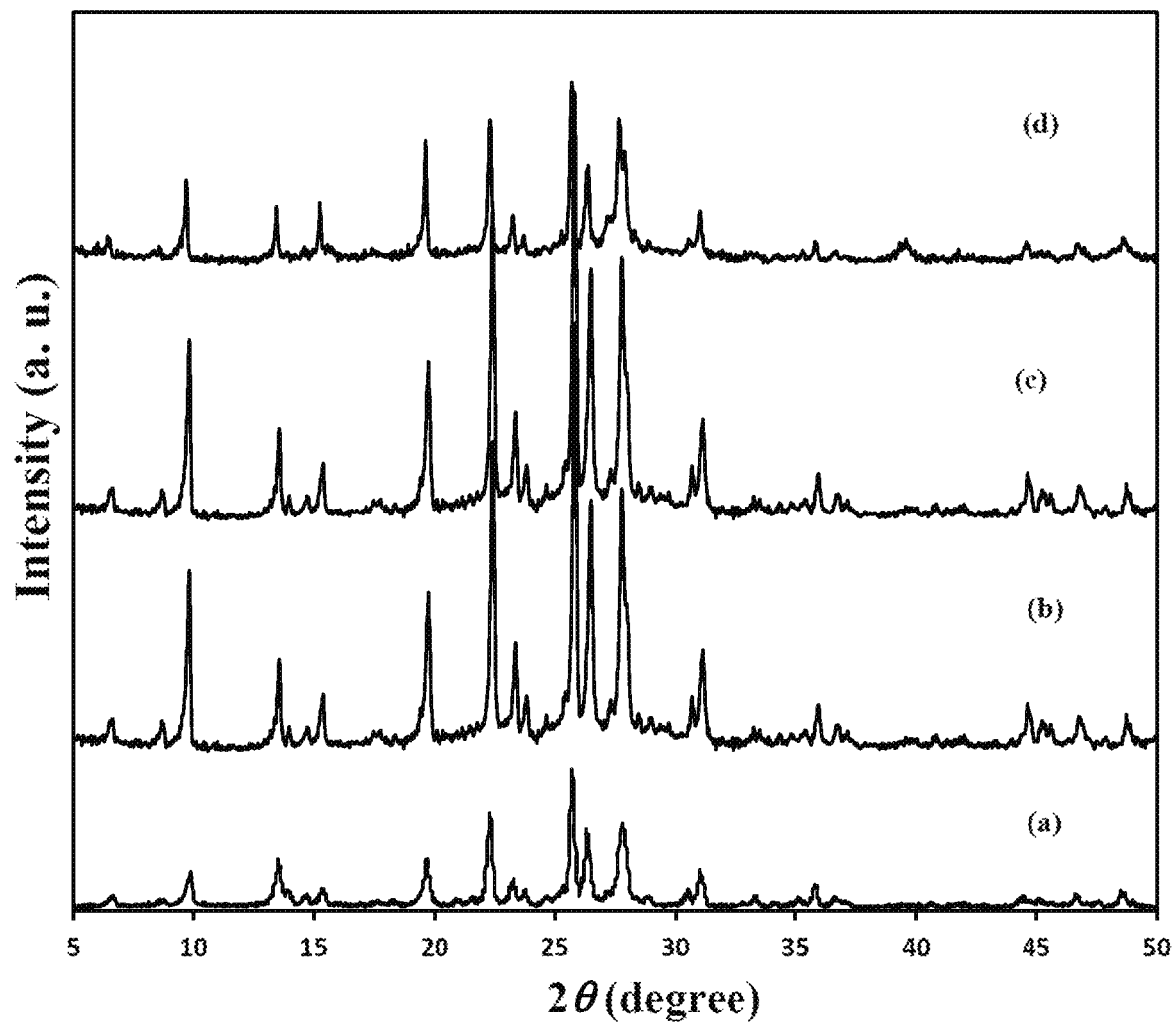
FIG. 35 is X-ray diffraction (XRD) patterns of mordenite zeolite with a silica to alumina ratio of 15 (H-MOR-15) before lanthanum impregnation (a) and after lanthanum impregnation with different loadings of lanthanum including 2 wt % La-MOR (b), 5 wt % La-MOR (c), and 10 wt % La-MOR (d).
Figure 36:
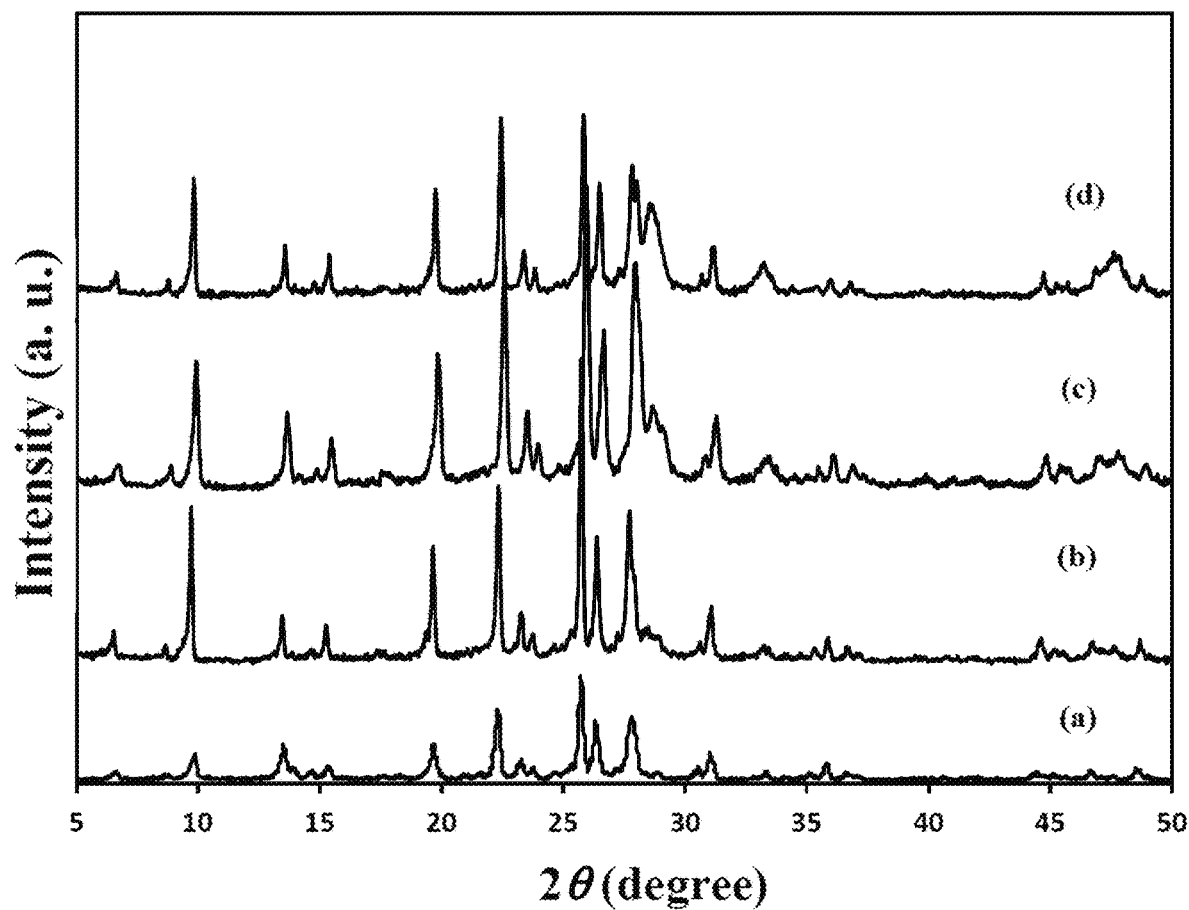
FIG. 36 is X-ray diffraction (XRD) patterns of mordenite zeolite with a silica to alumina ratio of 15 (H-MOR-15) before cerium impregnation (a) and after cerium impregnation with different loadings of cerium including 2 wt % Ce-MOR (b), 5 wt % Ce-MOR (c), and 10 wt % Ce-MOR (d).
Figure 37:
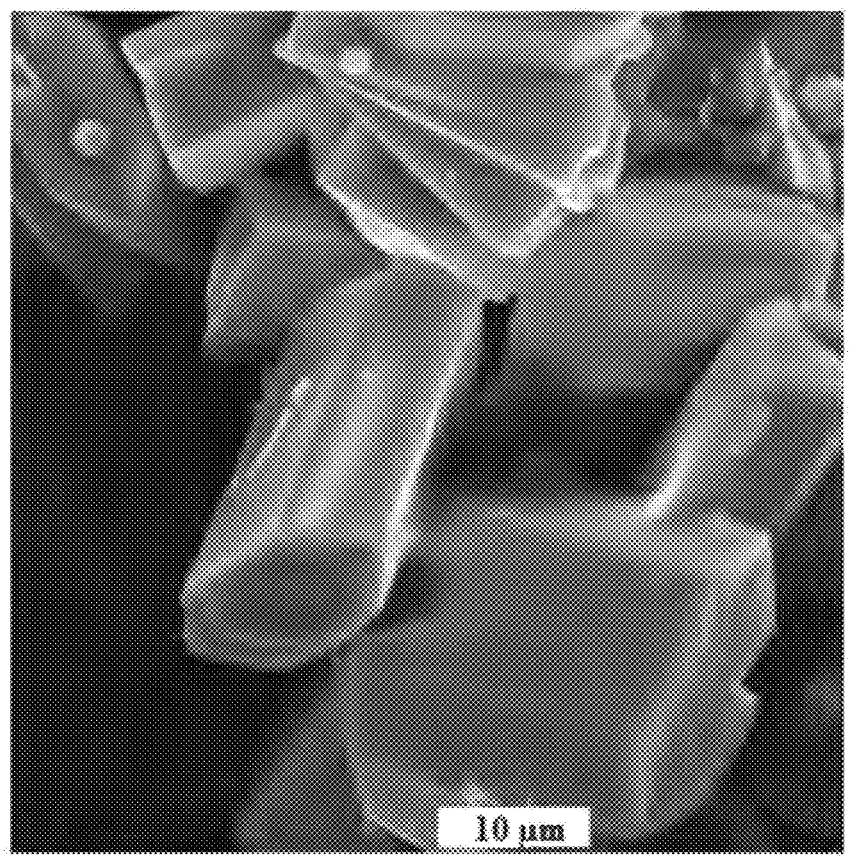
FIG. 37 is a scanning electron microscopy (SEM) micrograph of mordenite zeolite crystals with a silica to alumina ratio of 15 and impregnated with 2 wt % lanthanum (2 wt % La-MOR).
Figure 38:
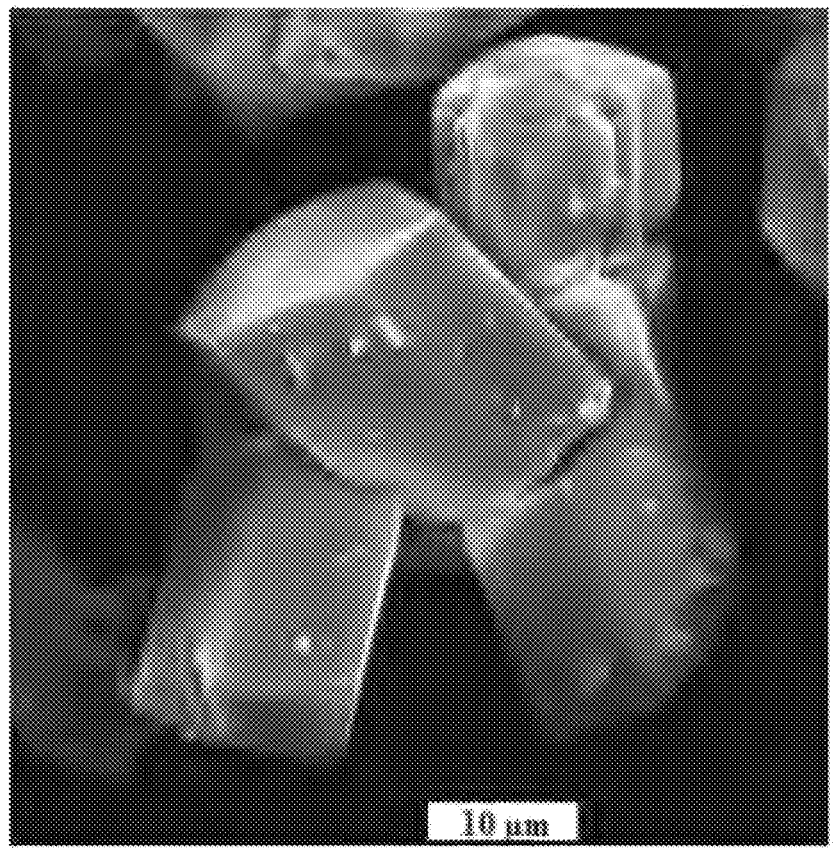
FIG. 38 is a scanning electron microscopy (SEM) micrograph of mordenite zeolite crystals with a silica to alumina ratio of 15 and impregnated with 5 wt % lanthanum (5 wt % La-MOR).
Figure 39:
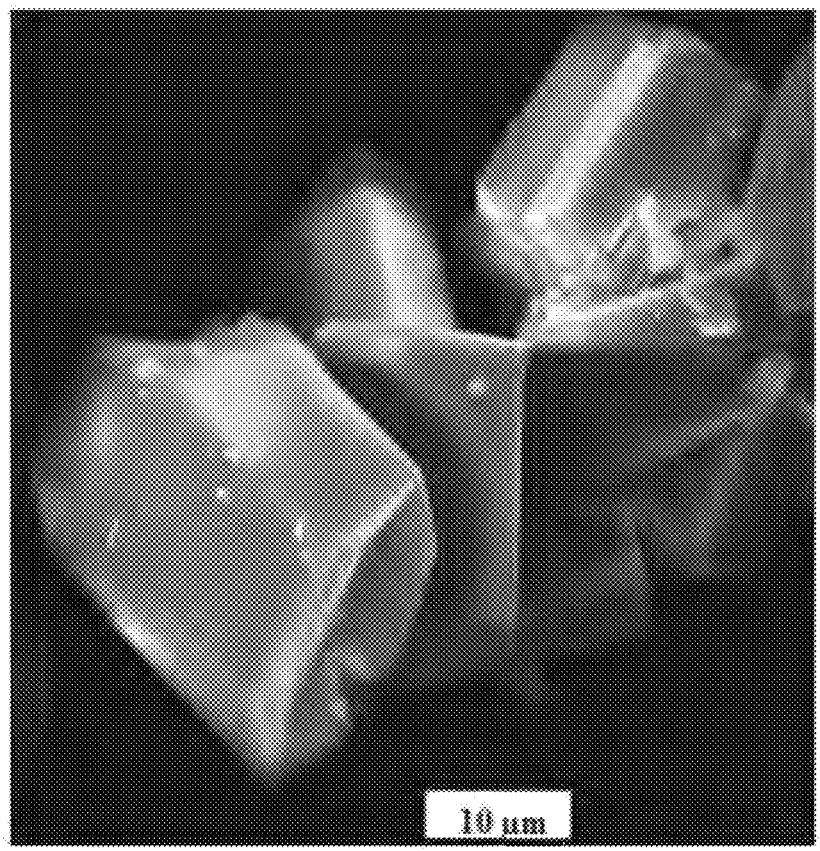
FIG. 39 is a scanning electron microscopy (SEM) micrograph of mordenite zeolite crystals with a silica to alumina ratio of 15 and impregnated with 10 wt % lanthanum (10 wt % La-MOR).
Figure 40:
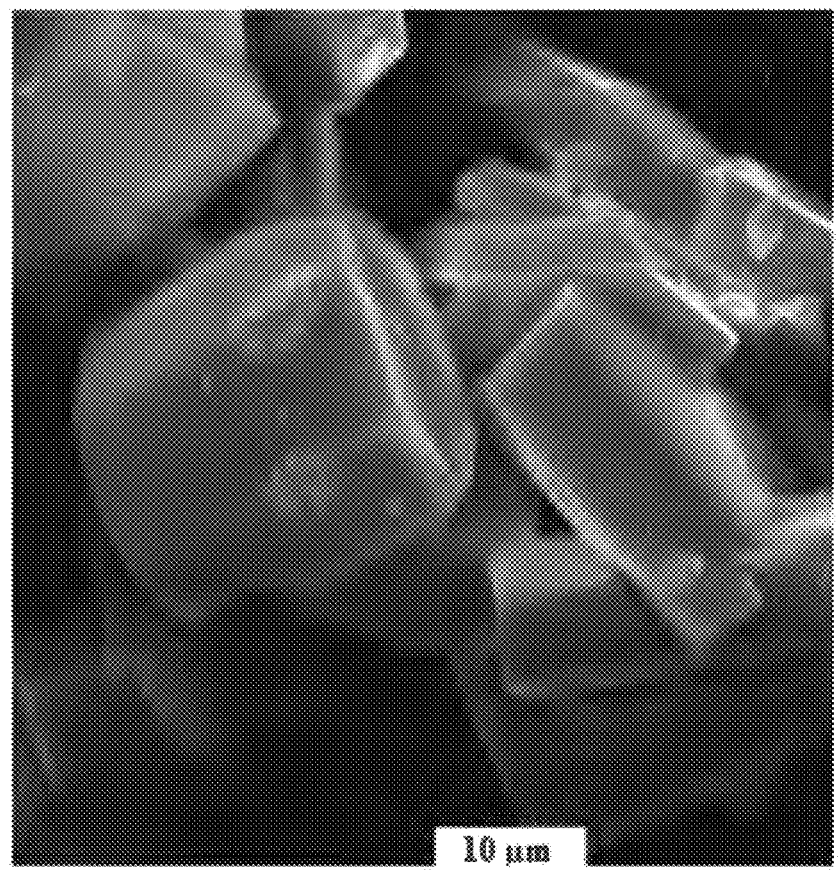
FIG. 40 is a scanning electron microscopy (SEM) micrograph of mordenite zeolite crystals with a silica to alumina ratio of 15 and impregnated with 2 wt % cerium (2 wt % Ce-MOR).
Figure 41:
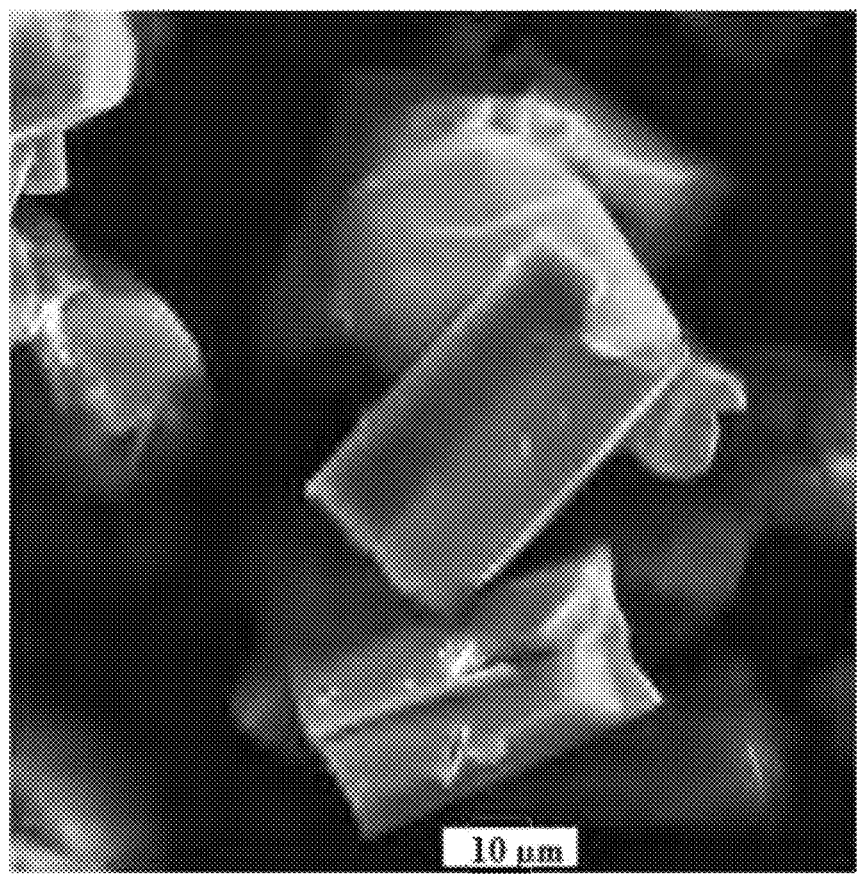
FIG. 41 is a scanning electron microscopy (SEM) micrograph of mordenite zeolite crystals with a silica to alumina ratio of 15 and impregnated with 5 wt % cerium (5 wt % Ce-MOR).
Figure 42:
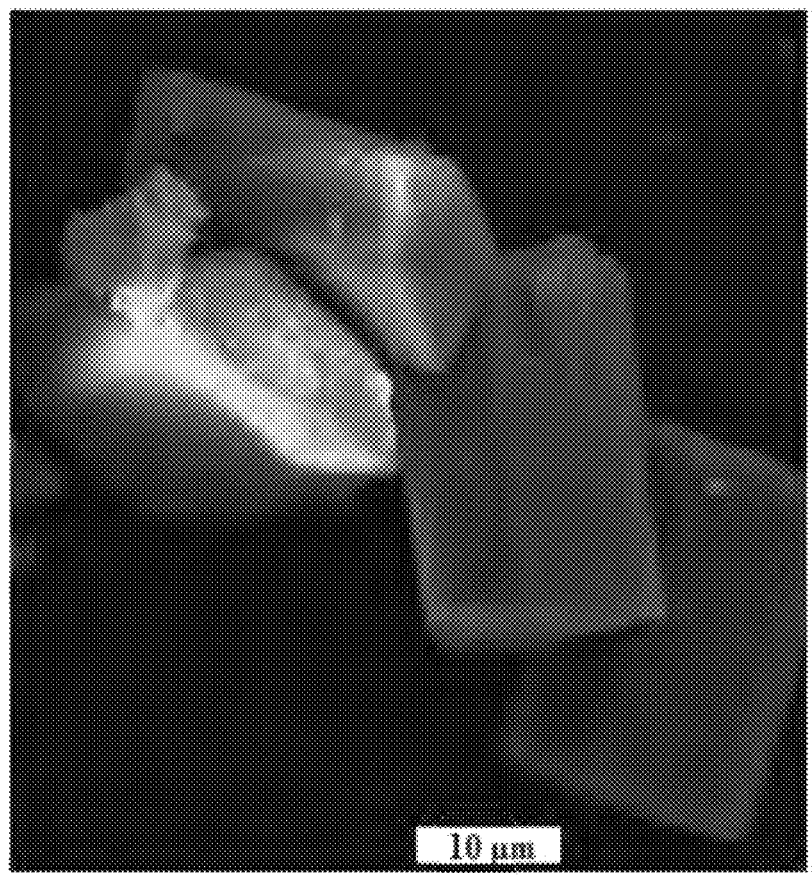
FIG. 42 is a scanning electron microscopy (SEM) micrograph of mordenite zeolite crystals with a silica to alumina ratio of 15 and impregnated with 10 wt % cerium (10 wt % Ce-MOR).

The energy-dispersive X-ray spectroscopy (EDX) result of the prepared mordenite (MOR-15) sample (FIG. 34) showed the presence of O, Al, and Si. The weight percent of each element is summarized in Table 6. After impregnations of the zeolite with La(III) and Ce(III) ions, the XRD pattern, the SEM images and the EDX spectrum of the crystal were determined to ensure that the crystallinity was not lost. The results of the XRD pattern (FIG. 35 and FIG. 36) showed that the crystallinity of the mordenite (MOR) zeolite was not damaged, and the results of the SEM (FIG. 37, FIG. 38, FIG. 39, FIG. 40, FIG. 41, and FIG. 42) also showed that the crystal morphology was retained. Several spots are visible on the metal impregnated zeolites, indicating the binding between the zeolite crystal and the impregnated metals. Table 7 and Table 8 summarize the weight percent of the elements present in the zeolite after La(III) and Ce(III) impregnation respectively obtained from their corresponding EDX spectra

TABLE 6

Weight percent of elements of prepared mordenite zeolite (MOR-15)

| Element | Oxygen (wt %) | Aluminum (wt %) | Silicon (wt %) | Total (wt %) |
|---|---|---|---|---|
| Mean | 55.87 | 4.68 | 39.45 | 100 |

TABLE 7

Weight percent of elements of lanthanum impregnated mordenite zeolite (La-MOR-15)

| Material | Oxygen (wt %) | Aluminum (wt %) | Silicon (wt %) | Lanthanum (wt %) | Total (wt %) |
|---|---|---|---|---|---|
| 2 wt % La-MOR | 56.48 | 4.39 | 37.45 | 1.68 | 100 |
| 5 wt % La-MOR | 55.99 | 4.82 | 36.67 | 2.51 | 100 |
| 10 wt % La-MOR | 51.28 | 4.38 | 36.00 | 8.34 | 100 |

TABLE 8

Weight percent of elements of cerium impregnated mordenite zeolite (Ce-MOR-15)

| Material | Oxygen (wt %) | Aluminum (wt %) | Silicon (wt %) | Cerium (wt %) | Total (wt %) |
| --- | --- | --- | --- | --- | --- |
| 2 wt % Ce-MOR | 53.46 | 4.41 | 39.66 | 2.47 | 100 |
| 5 wt % Ce-MOR | 56.80 | 4.27 | 34.09 | 4.85 | 100 |
| 10 wt % Ce-MOR | 51.33 | 4.20 | 34.46 | 10.01 | 100 |

Figure 43:
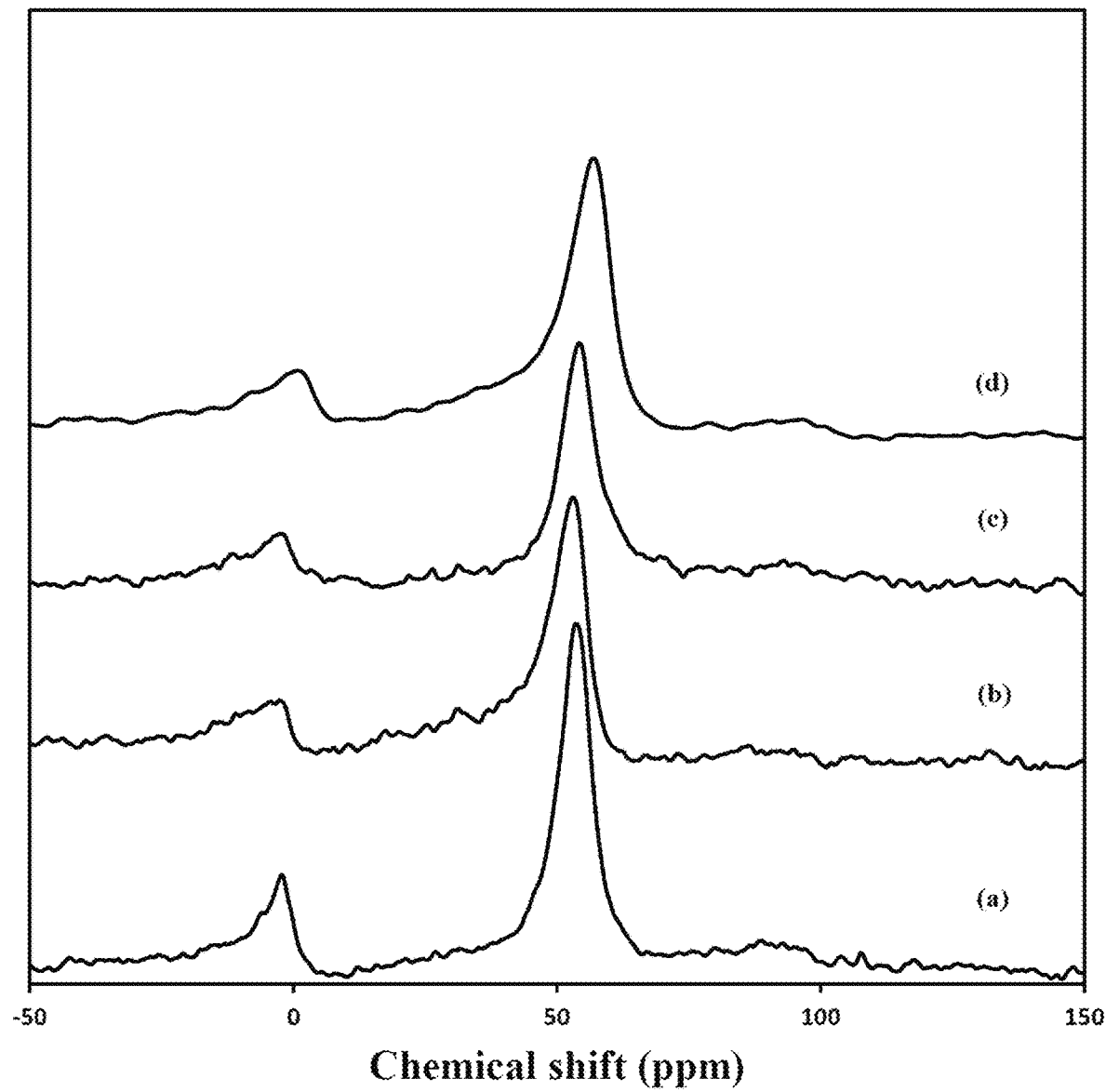
FIG. 43 is $^{27}$Al magic angle spinning nuclear magnetic resonance (MAS NMR) spectra of a mordenite zeolite (MOR-15) before rare earth metal impregnation (a) and after lanthanum (La) or cerium (Ce) impregnation including 2 wt % La/Ce-MOR (b), 5 wt % La/Ce-MOR (c), and 10 wt % La/Ce-MOR (d).

The incorporation of La (III) and Ce (III) ions into the framework of the zeolite was also confirmed by $^{27}$Al MAS NMR. $^{27}$Al NMR provides information about the environment of the aluminum atoms in the zeolite samples. Aluminum atoms tetrahedrally coordinated to the zeolite framework $(Al(OSi)_4)$, appear as a chemical shift at ~50 ppm, whereas external framework aluminum atoms which are octahedrally coordinated to the framework give a chemical shift signal of ~0 ppm [Müller, M., G. Harvey, and R. Prins, *Quantitative multinuclear MAS NMR studies of zeolites.* Microporous and Mesoporous Materials, 2000. 34(3): p. 281-290.—incorporated herein by reference in its entirety]. In strongly dealluminated zeolite samples, a further peak is usually observed between 30 and 50 ppm, and this has been assigned in the literature to penta-coordinated aluminum atoms as wells as distorted tetrahedrally coordinated aluminum atoms in the external framework [Gilson, J.-P., et al., *Penta-co-ordinated aluminium in zeolites and aluminosilicates.* Journal of the Chemical Society, Chemical Communications, 1987(2): p. 91-92; and Samoson, A., et al., *Quantitative high-resolution 27Al NMR: tetrahedral nonframework aluminium in hydrothermally treated zeolites.* Chemical Physics Letters, 1987. 134(6): p. 589-592.—each incorporated herein by reference in its entirety]. The results of the NMR analysis in this process indicates that the two peaks corresponding to the tetrahedral and octahedral aluminum atoms were both obtained for the parent unmodified zeolite and the rare earth metal impregnated zeolites. However, as the metal loading increases, the intensities of the peaks decreases implying that the ratio of the Al atoms have decreased as a result of the incorporation of the metals. FIG. 43 demonstrates this occurrence.

Example 7

Electrochemical Characterization of a Prepared Lanthanum or Cerium Impregnated Zeolite Modified Carbon Paste Electrode (La/Ce-ZMCPE)

Figure 44:
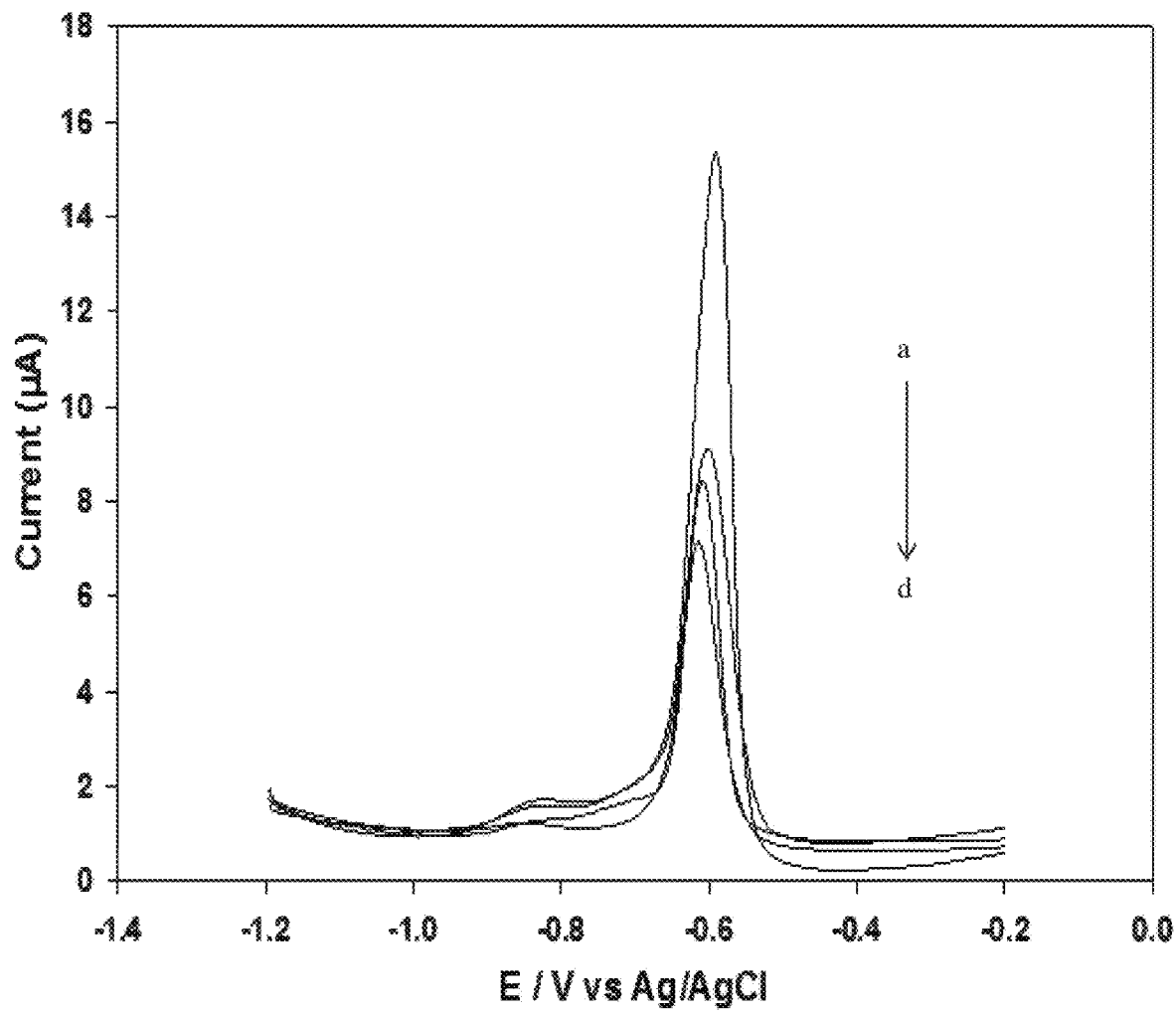
FIG. 44 illustrates the effect of varying lanthanum loading (0 wt % to 10 wt %) on the square wave anodic stripping voltammetry (SWASV) voltammograms of 500 ppb Pb(II) in 0.1 M phosphate buffer (pH=4) at a La-MOR-15 zeolite modified carbon paste electrode with the graphite:zeolite:paraffin ratio of 50:25:25 with lanthanum loadings of 2 wt % La (a), 5 wt % La (b) and 10 wt % La (c) or an unmodified mordenite zeolite carbon paste electrode of 0 wt % La (d) at an accumulation potential of −1.2 V, an accumulation time of 120 seconds, a potential step of 5 mV, an amplitude of 50 mV, and a frequency of 15 Hz.
Figure 45:
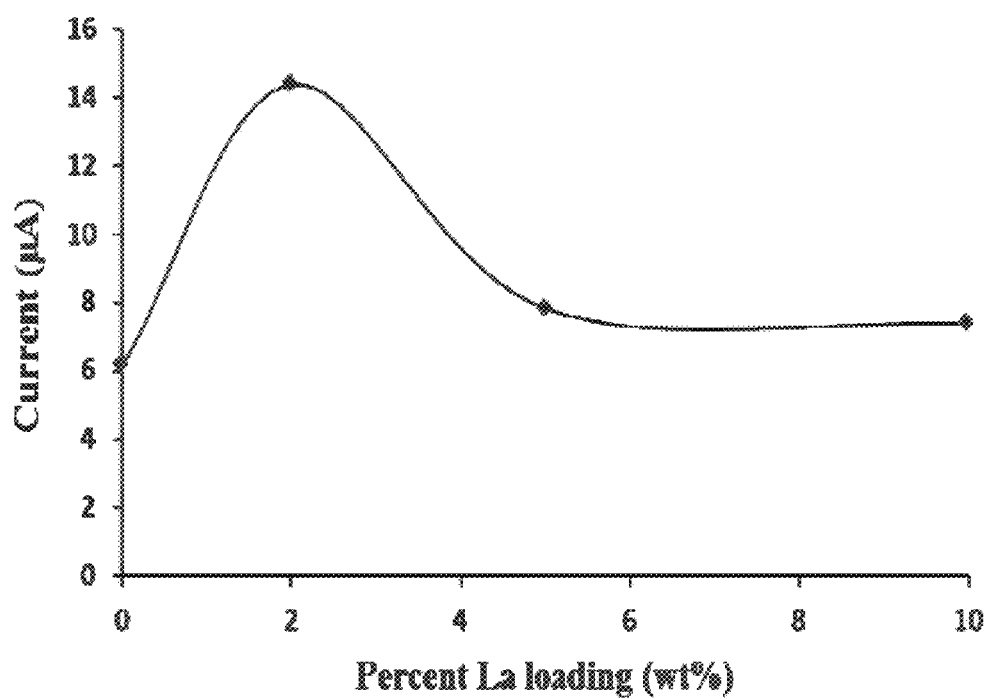
FIG. 45 is a plot of the current for the La-MOR-15 zeolite modified carbon paste electrode with the graphite:zeolite:paraffin ratio of 50:25:50 versus the weight percent of lanthanum (La) loading.

The electrochemical behavior of the lanthanum/cerium modified mordenite zeolite (La/Ce-MOR) was investigated by the construction of a La/Ce-zeolite modified carbon paste electrode (La/Ce-ZMCPE) for the square wave anodic stripping voltammetric detection of Pb(II) and Cd(II) ions in aqueous solutions. Preliminary measurements were carried out in order to screen out appropriate electrodes since for each metal (La and Ce), three different loadings were synthesized (2, 5 and 10 wt %). It was therefore necessary to screen out the electrodes in order to obtain the one which would give the maximum detection ability. For the preliminary measurements, electrodes were constructed in the ratio of 50:25:25 (graphite:zeolite:paraffin) and the square wave anodic stripping experiments were carried out in 500 ppb Pb(II) solution in 0.1 M phosphate buffer (pH=4). FIG. 44 shows the square wave anodic stripping voltammetry (SWASV) voltammograms obtained at La-ZMCPE with different lanthanum loadings. FIG. 45 is a plot of current versus the percent lanthanum (La) loading (wt %). From the results, a remarkable decrease was observed in the peak height as the metal loading increases, with 2 wt % La-ZMCPE having the highest peak height. It was also observed that bare carbon past electrode prepared in the ratio of 75:25 (graphite:paraffin) has a peak height that is less than those of the modified electrode. This is an indication of an improved sensitivity of the electrode as a result of metal impregnation. In square wave voltammetry, peak height is a function of the concentration of the analyte present in the medium. As such the electrode which gives a better peak height is regarded as being more sensitive to the detection of the analyte. For the lanthanum zeolite modified carbon paste electrode (La-ZMCPE), 2 wt % La-ZMCPE (2%-La-ZMCPED) gave an advantageous peak current and was therefore employed for the purposes of this disclosure.

Figure 46:
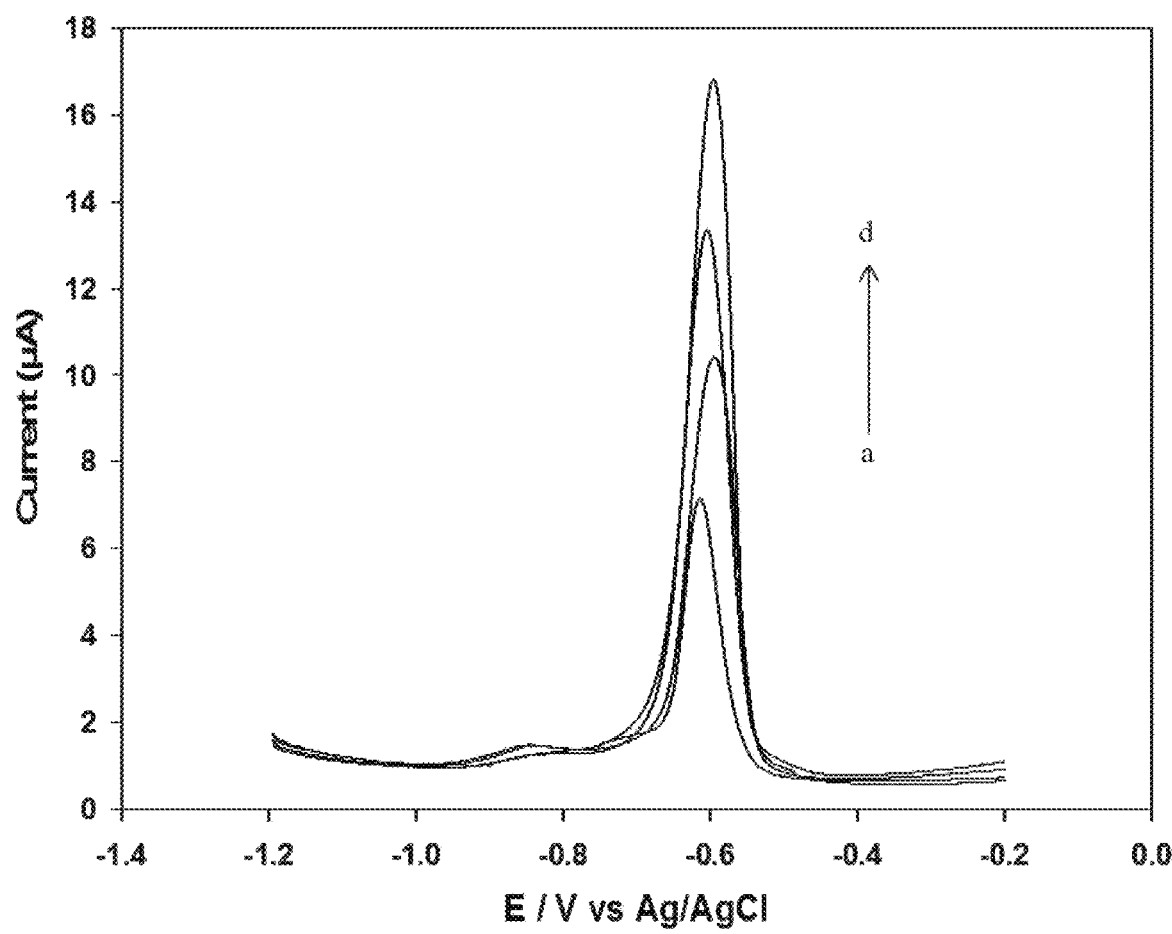
FIG. 46 illustrates the effect of varying cerium loading (0 wt % to 10 wt %) on the square wave anodic stripping voltammetry (SWASV) voltammograms of 500 ppb Pb(II) in 0.1 M phosphate buffer (pH=4) at a Ce-MOR-15 zeolite modified carbon paste electrode with the graphite:zeolite:paraffin ratio of 50:25:25 with cerium loadings of 2 wt % Ce (b), 5 wt % Ce (c) and 10 wt % Ce (d) or an unmodified mordenite zeolite carbon paste electrode of 0 wt % Ce (a) at an accumulation potential of −1.2 V, an accumulation time of 120 seconds, a potential step of 5 mV, an amplitude of 50 mV, and a frequency of 15 Hz.
Figure 47:
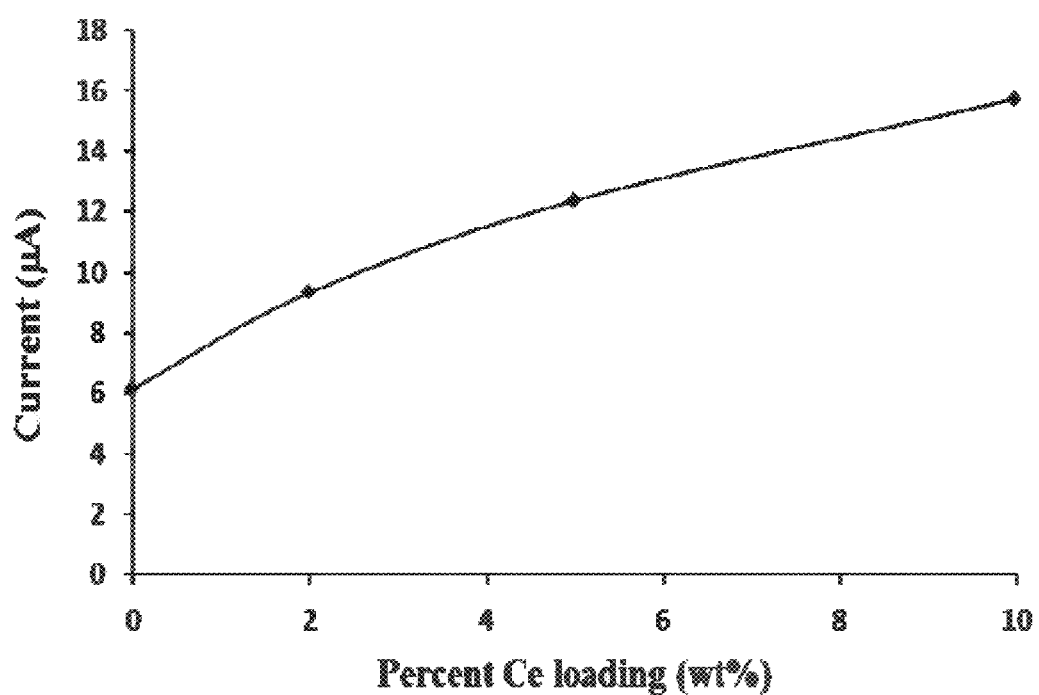
FIG. 47 is a plot of the current for the Ce-MOR-15 zeolite modified carbon paste electrode with the graphite:zeolite:paraffin ratio of 50:25:50 versus the weight percent of cerium (Ce) loading.

In contrast, the electrochemical behavior of the Ce-ZMCPE was the reverse of that of the La-ZMCPE as the square wave stripping peak increases as the metal loading increases, with 10 wt % Ce giving the highest peak. FIG. 46 shows this result. FIG. 47 is a plot of current versus the percent cerium (Ce) loading (wt %). From the results of these preliminary experiments, a reverse characteristic for composites of La and Ce was observed. It has been reported elsewhere that the catalytic properties of the two rare earth metals are the reverse of one another as La was reported to be more stabilizing than Ce, and hence less reactive [Thomas, B., B. B. Das, and S. Sugunan, *Rare earth exchanged (Ce3+., La3+ and RE3+) H-Y zeolites as solid acid catalysts for the synthesis of linear alkyl benzenes.* Microporous and Mesoporous Materials, 2006. 95(1-3): p. 329-338.—incorporated herein by reference in its entirety]. It has also been reported elsewhere that where metals were incorporated into various zeolites for applications which include alkylation of alpha-methyl naphthalene, desulfurization of diesel fuel and cracking of naphtha, that catalysts with low La loadings and high Ce loadings yielded advantageous desired results [Zhao, Z., et al., *Alkylation of α-methylnaphthalene with long-chain olefins catalyzed by rare earth lanthamim modified HY zeolite.* Journal of Molecular Catalysis A: Chemical, 2006. 250(1-2): p. 50-56; and Subhan, F., et al., *High desulfurization characteristic of lanthanum loaded mesoporous MCM-41 sorbents for diesel fuel.* Fuel Processing Technology, 2012. 97(0): p. 71-78; and Taghipour, N., et al., *The effect of key factors on thermal catalytic cracking of naphtha over Ce—La/SAPO-34 catalyst by statistical design of experiments.* Journal of Analytical and Applied Pyrolysis, 2013. 99(0): p. 184-190.—each incorporated herein by reference in its entirety]. One reason for such observations may be the ionic sizes of the rare earth metals with La having an ionic radius of 1.50 Å and Ce having an ionic radius of 1.48 Å. It could therefore be stated that, the smaller the metal ion the higher its ability to fit into the zeoliitic pores and the higher its catalytic characteristic.

Figure 48:
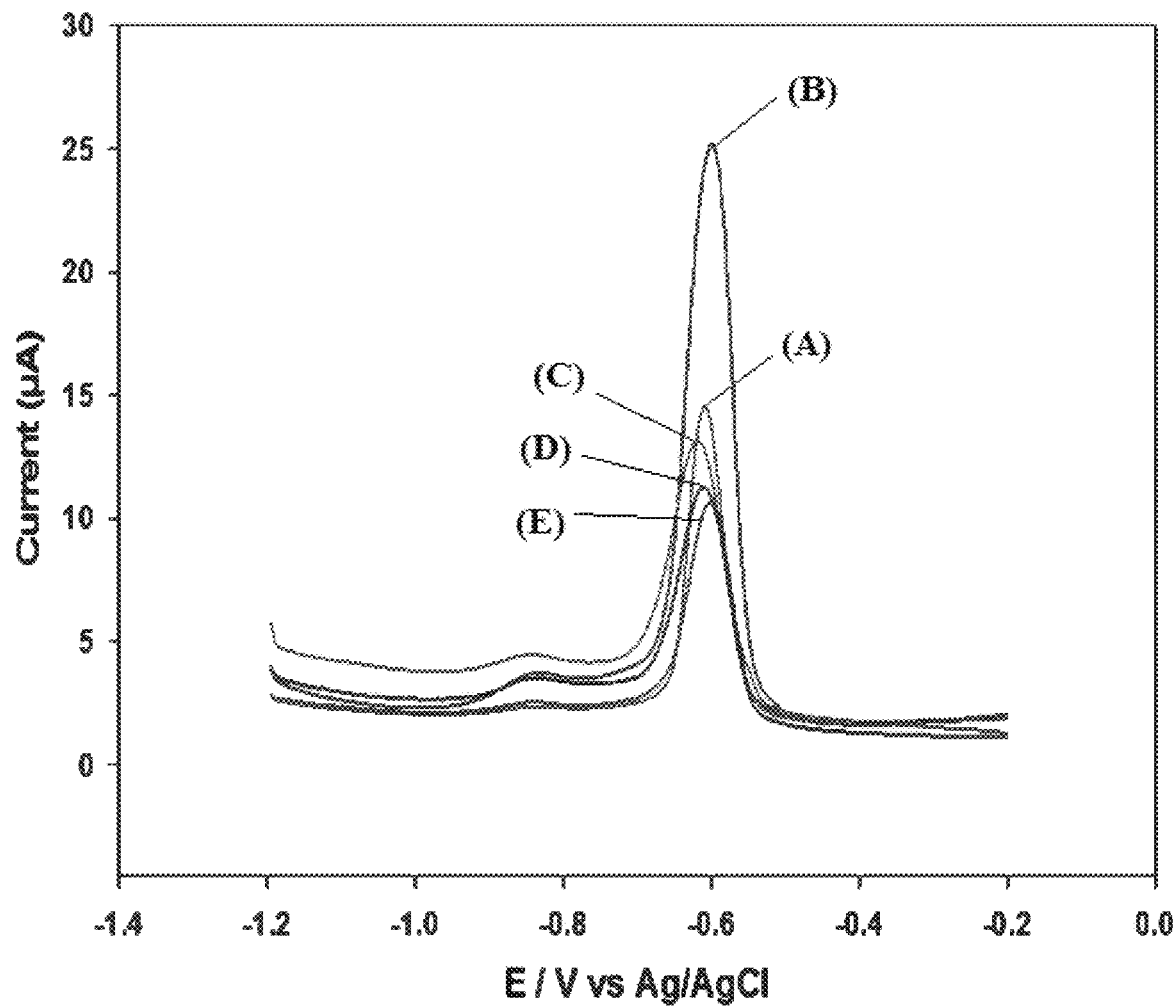
FIG. 48 illustrates the effect of varying electrode composition on the square wave anodic stripping voltammetry (SWASV) voltammograms of 500 ppb Pb(II) in 0.1 M phosphate buffer (pH=4) at a 2 wt % La-MOR-15 zeolite modified carbon paste electrode with the composite graphite:zeolite:paraffin ratio of 70:0:30 (A), 65:5:30 (B), 60:10:30 (C), 55:15:30 (D) and 50:20:30 (E) at an accumulation potential of −1.2 V, an accumulation time of 120 seconds, a potential step of 5 mV, an amplitude of 50 mV, and a frequency of 15 Hz.
Figure 49:
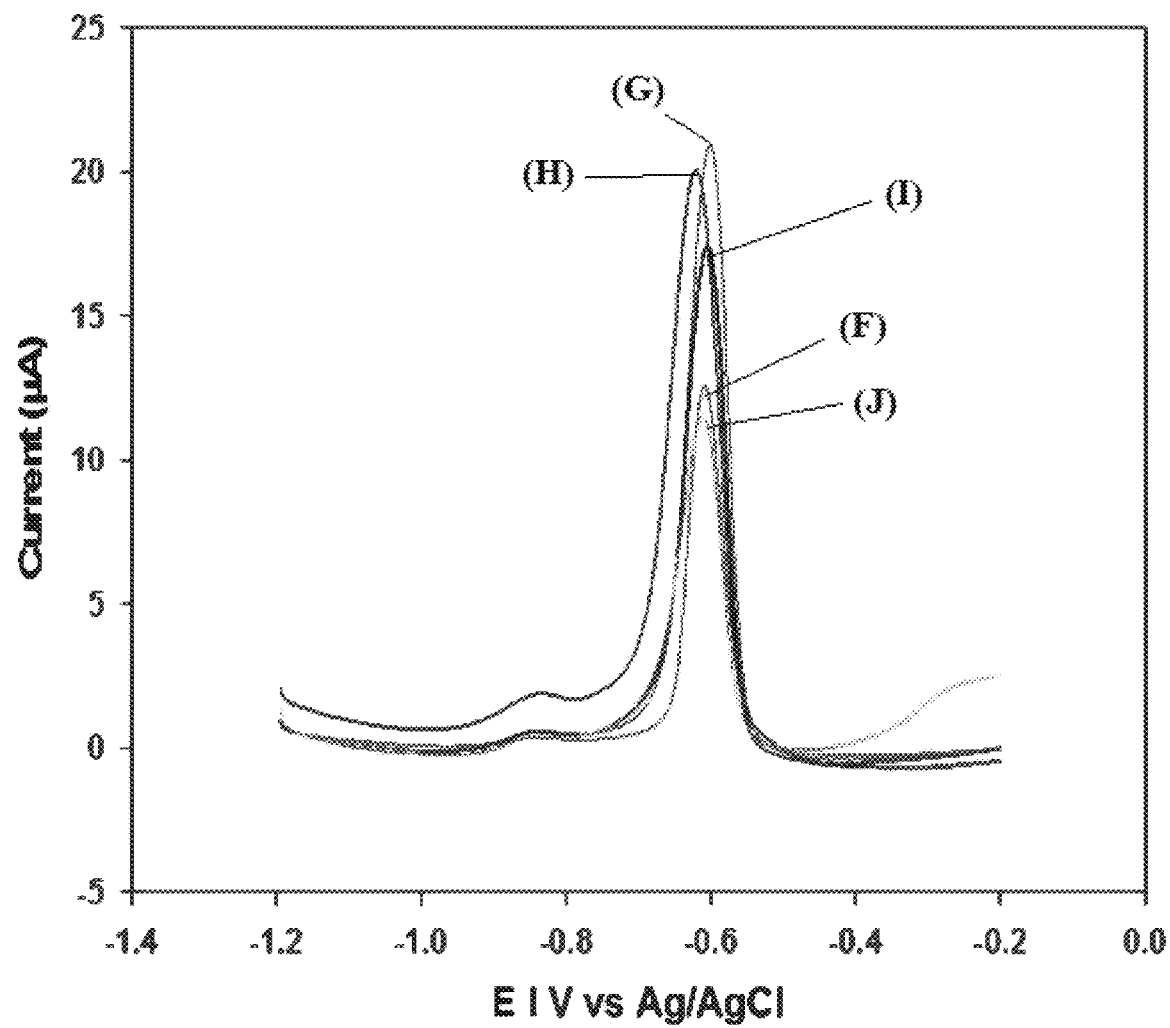
FIG. 49 illustrates the effect of varying electrode composition on the square wave anodic stripping voltammetry (SWASV) voltammograms of 500 ppb Pb(II) in 0.1 M phosphate buffer (pH=4) at a 10 wt % Ce-MOR-15 zeolite modified carbon paste electrode with the composite graphite:zeolite:paraffin ratio of 70:0:30 (F), 65:5:30 (G), 60:10:30 (H), 55:15:30 (1) and 50:20:30 (J) at an accumulation potential of −1.2 V, an accumulation time of 120 seconds, a potential step of 5 mV, an amplitude of 50 mV, and a frequency of 15 Hz.
Figure 50:
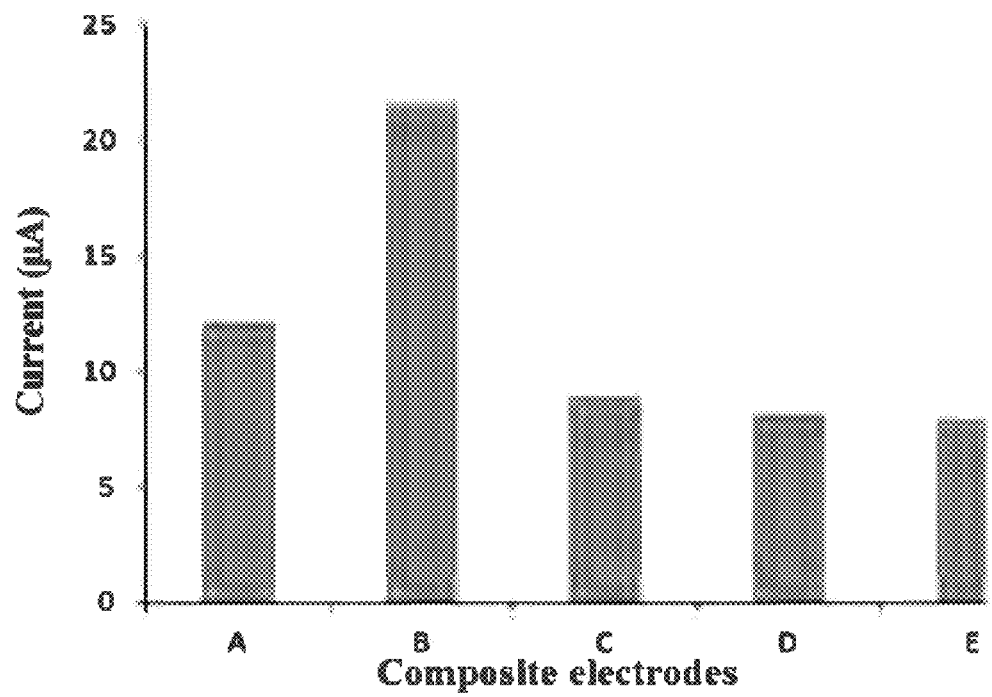
FIG. 50 is a graph of current for a 2 wt % La-MOR-15 zeolite modified carbon paste electrode with the composite graphite:zeolite:paraffin ratios of 70:0:30 (A), 65:5:30 (B), 60:10:30 (C), 55:15:30 (D) and 50:20:30 (E).
Figure 51:
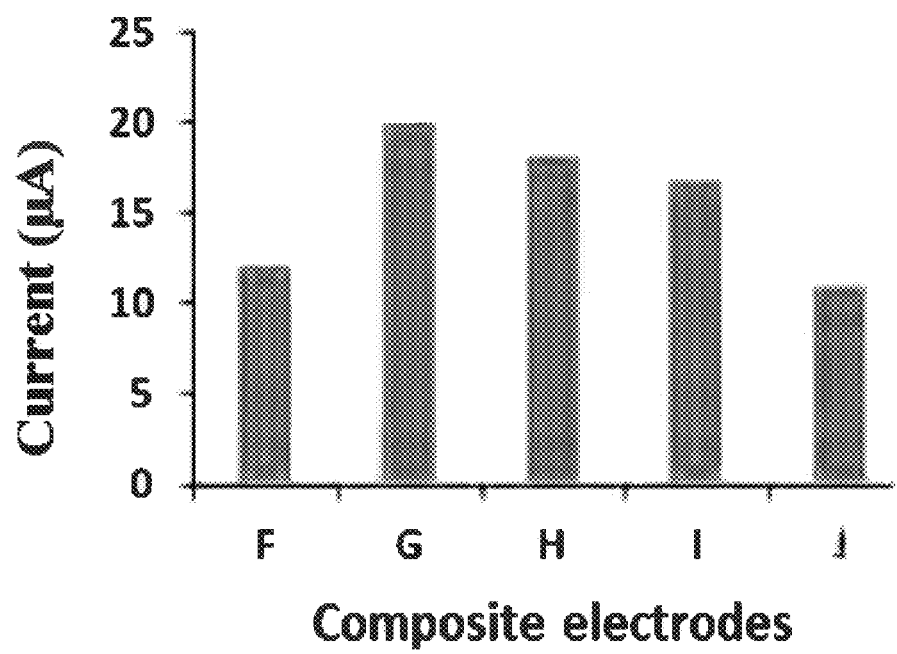
FIG. 51 is a graph of current for a 10 wt % Ce-MOR-15 zeolite modified carbon paste electrode with the composite graphite:zeolite:paraffin ratios of 70:0:30 (F), 65:5:30 (G), 60:10:30 (H), 55:15:30 (I) and 50:20:30 (J).

Having selected the two most effective composite electrodes (2 wt % La-ZMCPE and 10 wt % Ce-ZMCPE) further screening was carried out by varying the ratio of the composite materials (graphite, zeolite, and paraffin oil). Ten composites were fabricated according to Table 9. FIG. 48 and FIG. 49 present the square wave anodic stripping voltammetry (SWASV) voltammograms of 500 ppb Pb(II) solution for lanthanum composites (A-E) and cerium composites (F-J), respectively. FIG. 50 is a graph of current for the lanthanum composites (A-E). FIG. 51 is a graph of current for the cerium composites (F-J). It was observed from the SWASV voltammograms of 500 ppb Pb(II) solution that composite B and composite G both containing the ratio of 65:5:30 (graphite:zeolite:paraffin) give an advantageous peak height for both La and Ce and hence were adopted for the purposes of this disclosure.

TABLE 9

Composite ratio of prepared zeolite modified carbon paste electrodes 2 wt % La-ZMCPE (A-E) and 10 wt % Ce-ZMCPE (F-J)

| Composite Designation | Graphite | Zeolite | Paraffin oil |
|---|---|---|---|
| A | 70 | 0 | 30 |
| B | 65 | 5 | 30 |
| C | 60 | 10 | 30 |
| D | 55 | 15 | 30 |
| E | 50 | 10 | 30 |
| F | 70 | 0 | 30 |
| G | 65 | 5 | 30 |
| H | 60 | 10 | 30 |
| I | 55 | 15 | 30 |
| J | 50 | 20 | 30 |

Figure 52:
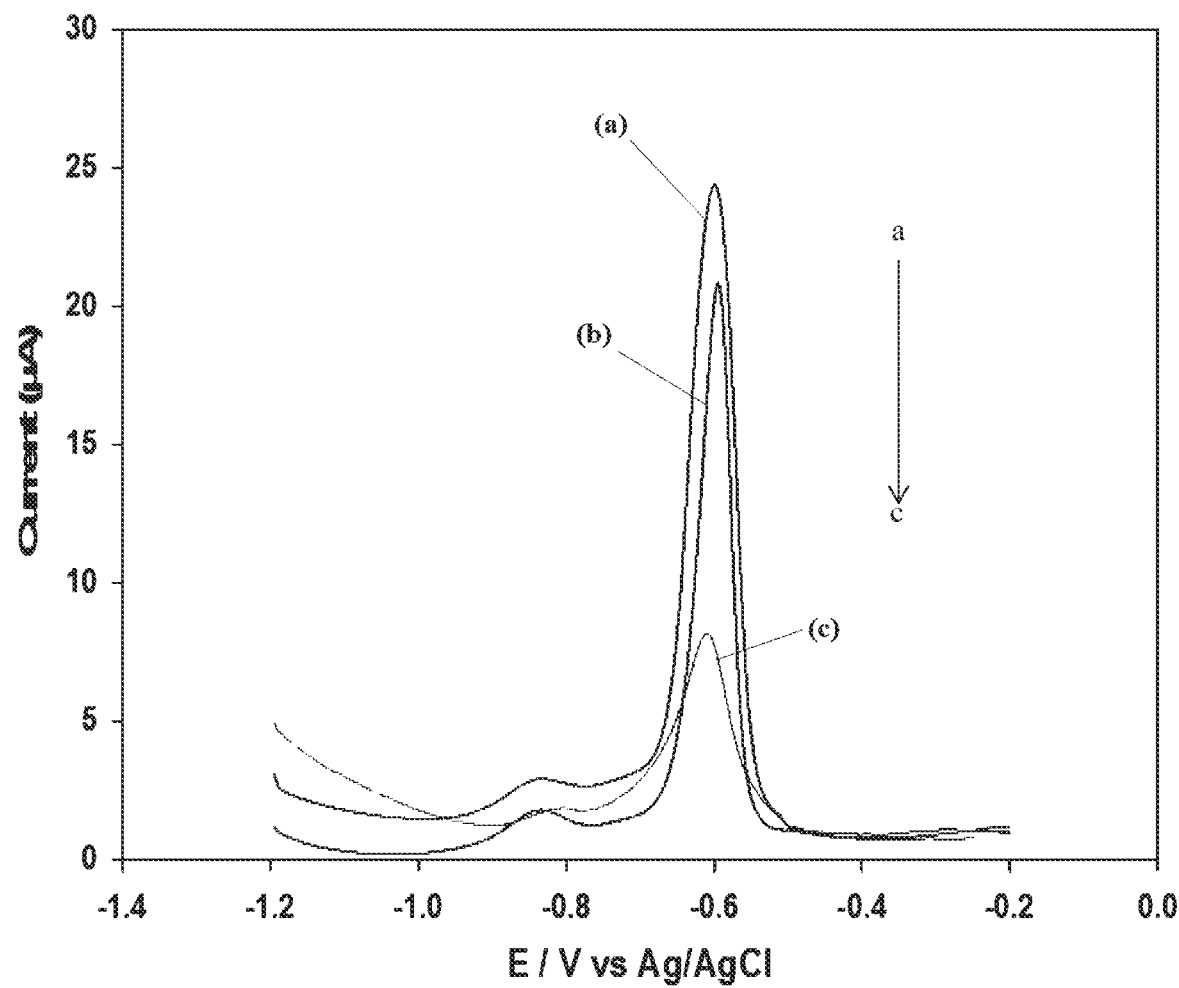
FIG. 52 illustrates the effect of varying supporting electrolyte buffer on the square wave anodic stripping voltammetry (SWASV) voltammograms of 500 ppb Pb(II) in 0.1 M phosphate buffer at pH=4 (a), 0.1 M sulfate buffer at pH=4 (b), and 0.1 M acetate buffer at pH=4 at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, an amplitude of 50 mV, and a frequency of 15 Hz.
Figure 53:
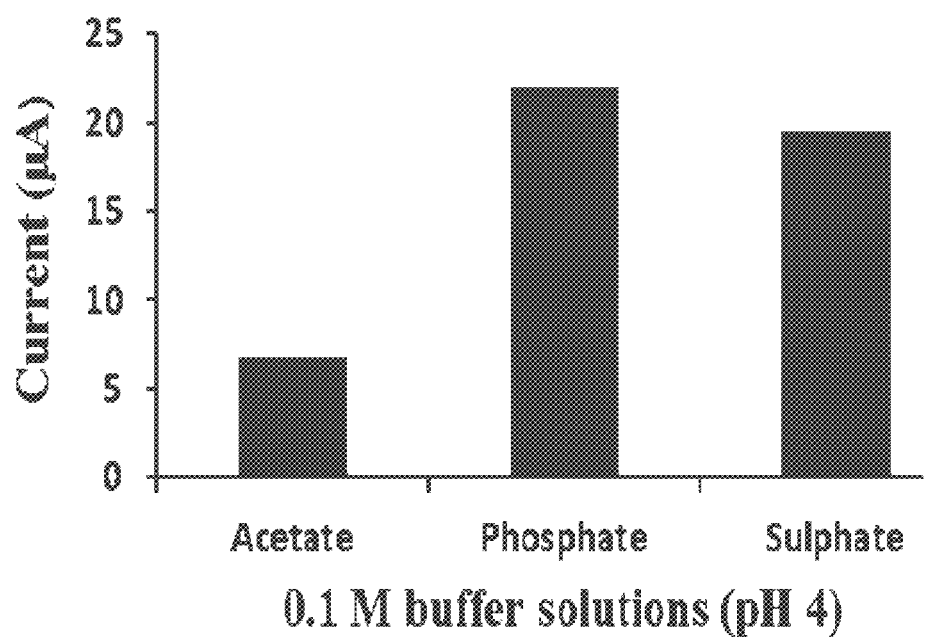
FIG. 53 is a graph of current for a 2 wt % La-MOR-15 zeolite modified carbon paste composite B electrode with the graphite:zeolite:paraffin ratio of 65:5:30 in 0.1 M phosphate buffer (pH=4), 0.1 M sulfate buffer (pH=4), and 0.1 M acetate buffer (pH=4).
Figure 54:
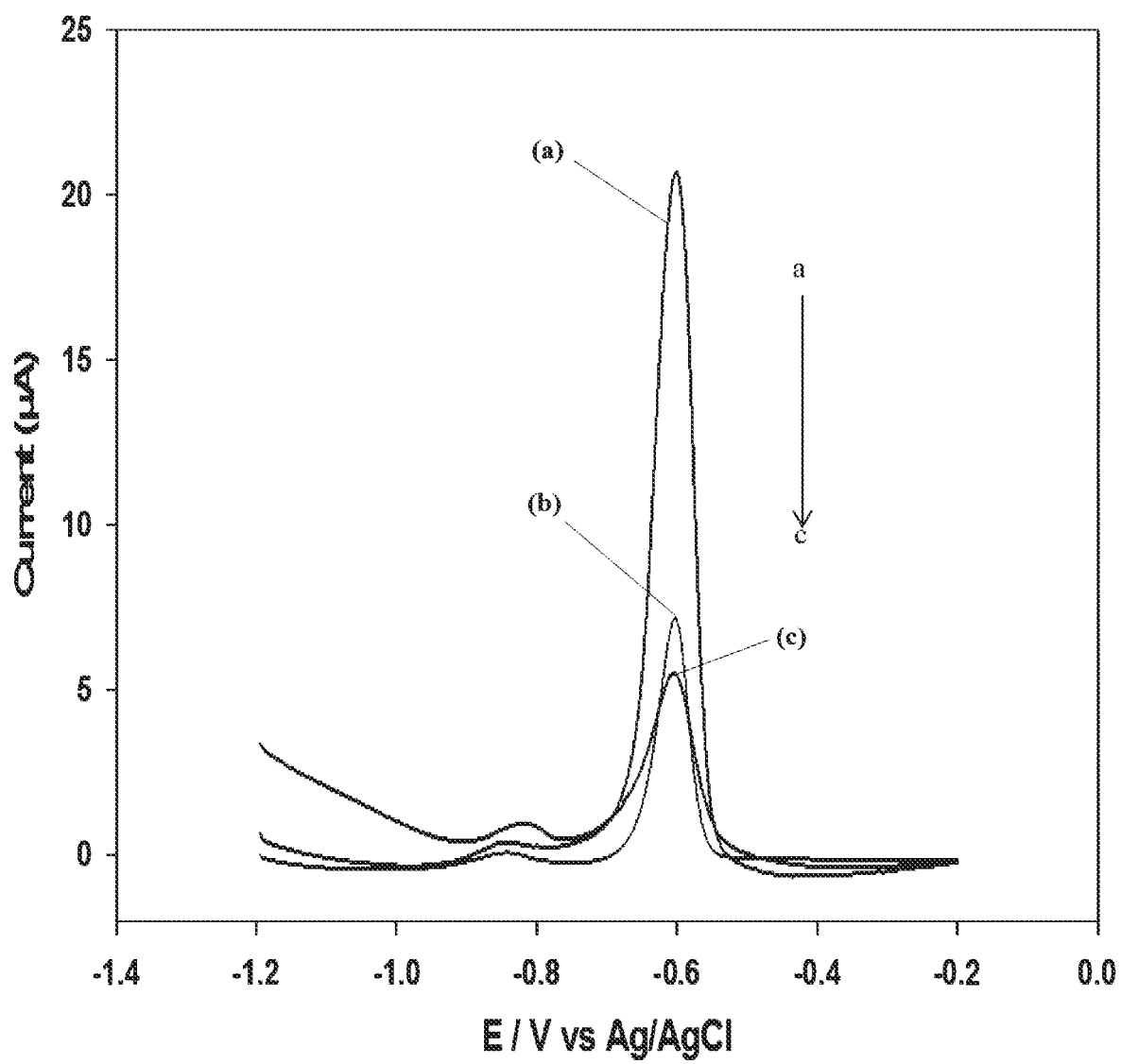
FIG. 54 illustrates the effect of varying supporting electrolyte buffer on the square wave anodic stripping voltammetry (SWASV) voltammograms of 500 ppb Pb(II) in 0.1 M phosphate buffer at pH=4 (a), 0.1 M sulfate buffer at pH=4 (b), and 0.1 M acetate buffer at pH=4 at a 10 wt % Ce-MOR-15 zeolite modified carbon paste composite G electrode with the graphite:zeolite:paraffin ratio of 65:5:30 at an accumulation potential of −1.2 V, an accumulation time of 120 seconds, a potential step of 5 mV, an amplitude of 50 mV, and a frequency of 15 Hz.
Figure 55:
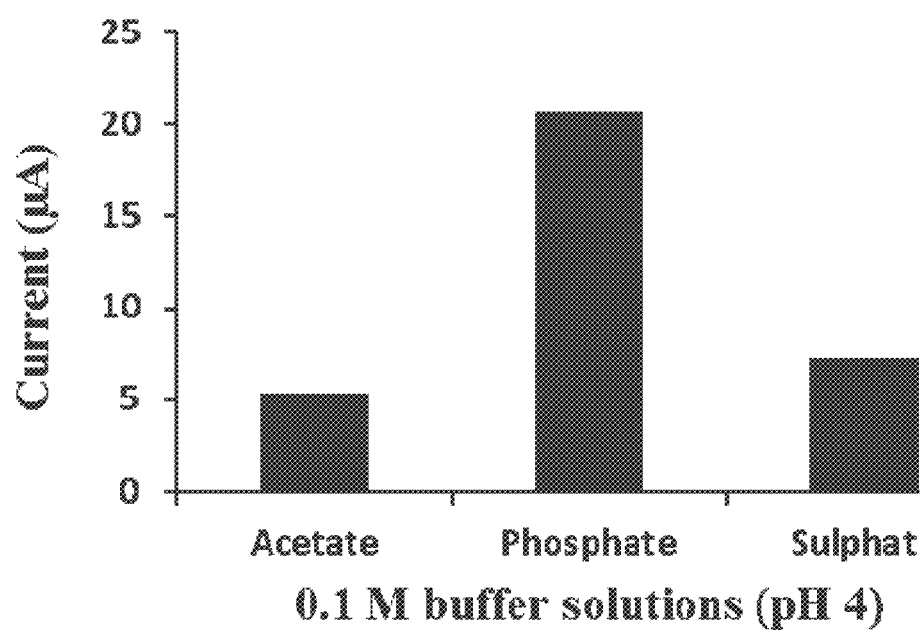
FIG. 55 is a graph of current for a 10 wt % Ce-MOR-15 zeolite modified carbon paste composite G electrode with the graphite:zeolite:paraffin ratio of 65:5:30 in 0.1 M phosphate buffer (pH=4), 0.1 M sulfate buffer (pH=4), and 0.1 M acetate buffer (pH=4).

The effects of the supporting electrolyte and its pH were also evaluated. A series of buffer solutions as supporting electrolytes were tested for their suitability in the detection of analytes in this procedure. The buffers include; 0.1 M acetate buffer; 0.1 M phosphate buffer; and 0.1 M sulfate buffer all at pH=4. FIG. 52 shows the square wave anodic stripping voltammetry (SWASV) voltammograms at a lanthanum composite B electrode in these three buffers. FIG. 53 is a graph of current for a lanthanum composite B electrode in the three 0.1 M buffer solutions. FIG. 54 shows the square wave anodic stripping voltammetry (SWASV) voltammograms at a cerium composite G electrode in these three buffers. FIG. 55 is a graph of current for a cerium composite G electrode in the three 0.1 M buffer solutions. The advantageous buffer solution chosen for subsequent use in this disclosure was 0.1 M phosphate buffer for both composite B and composite G electrodes.

Figure 56:
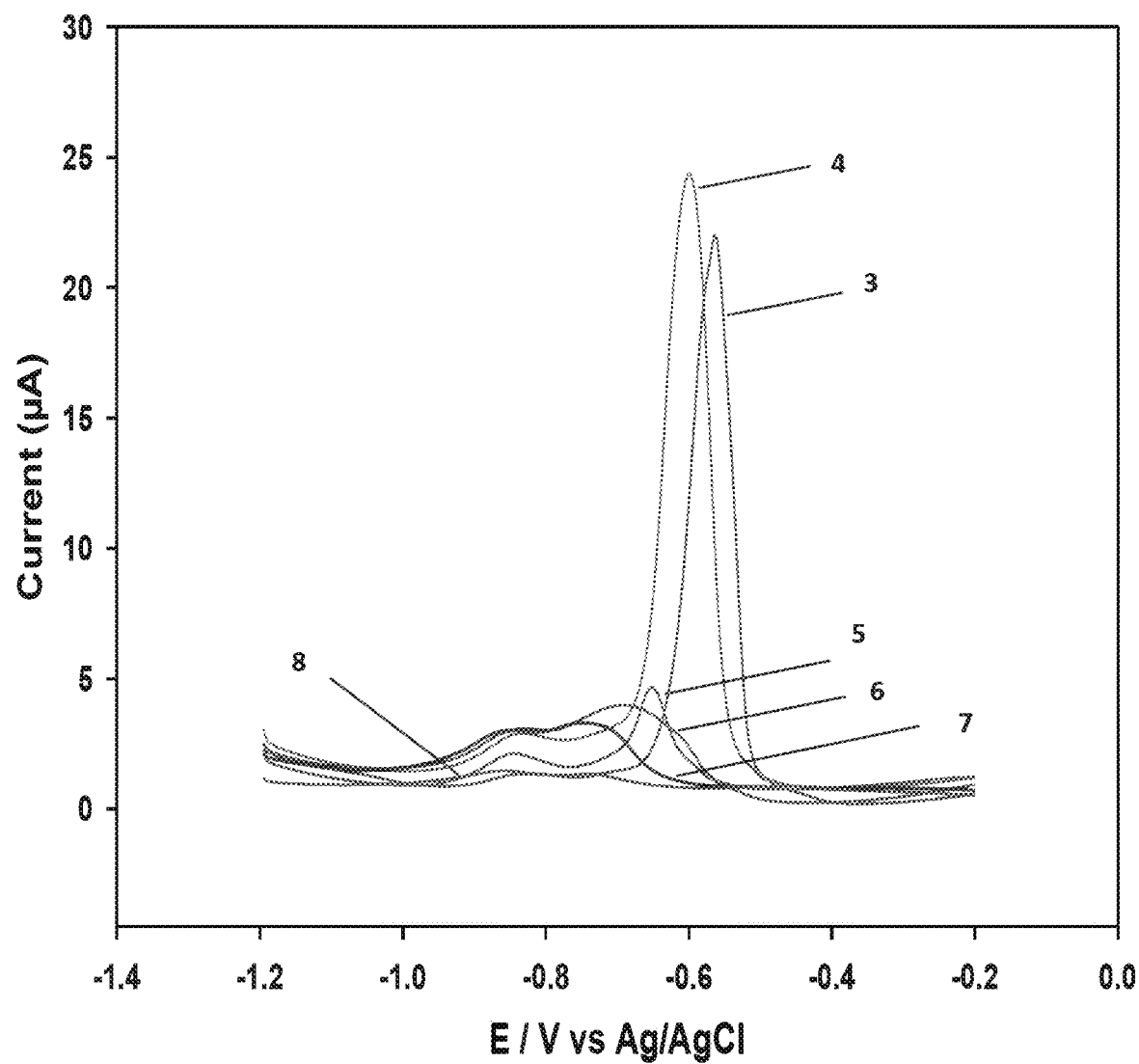
FIG. 56 illustrates the effect of varying pH values (3 to 8) on the square wave anodic stripping voltammetry (SWASV) voltammograms of 500 ppb Pb(II) in 0.1 M phosphate buffer at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, an amplitude of 50 mV, and a frequency of 15 Hz.
Figure 57:
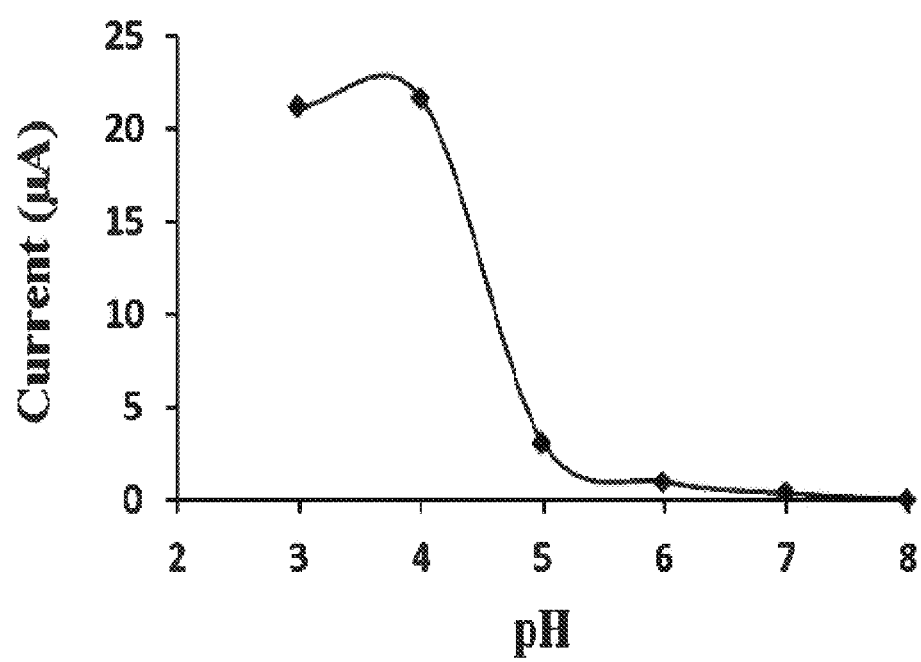
FIG. 57 is a plot of current for a 2 wt % La-MOR-15 zeolite modified carbon paste composite B electrode with the graphite:zeolite:paraffin ratio of 65:5:30 versus pH in 0.1 M phosphate buffer supporting electrolyte.
Figure 58:
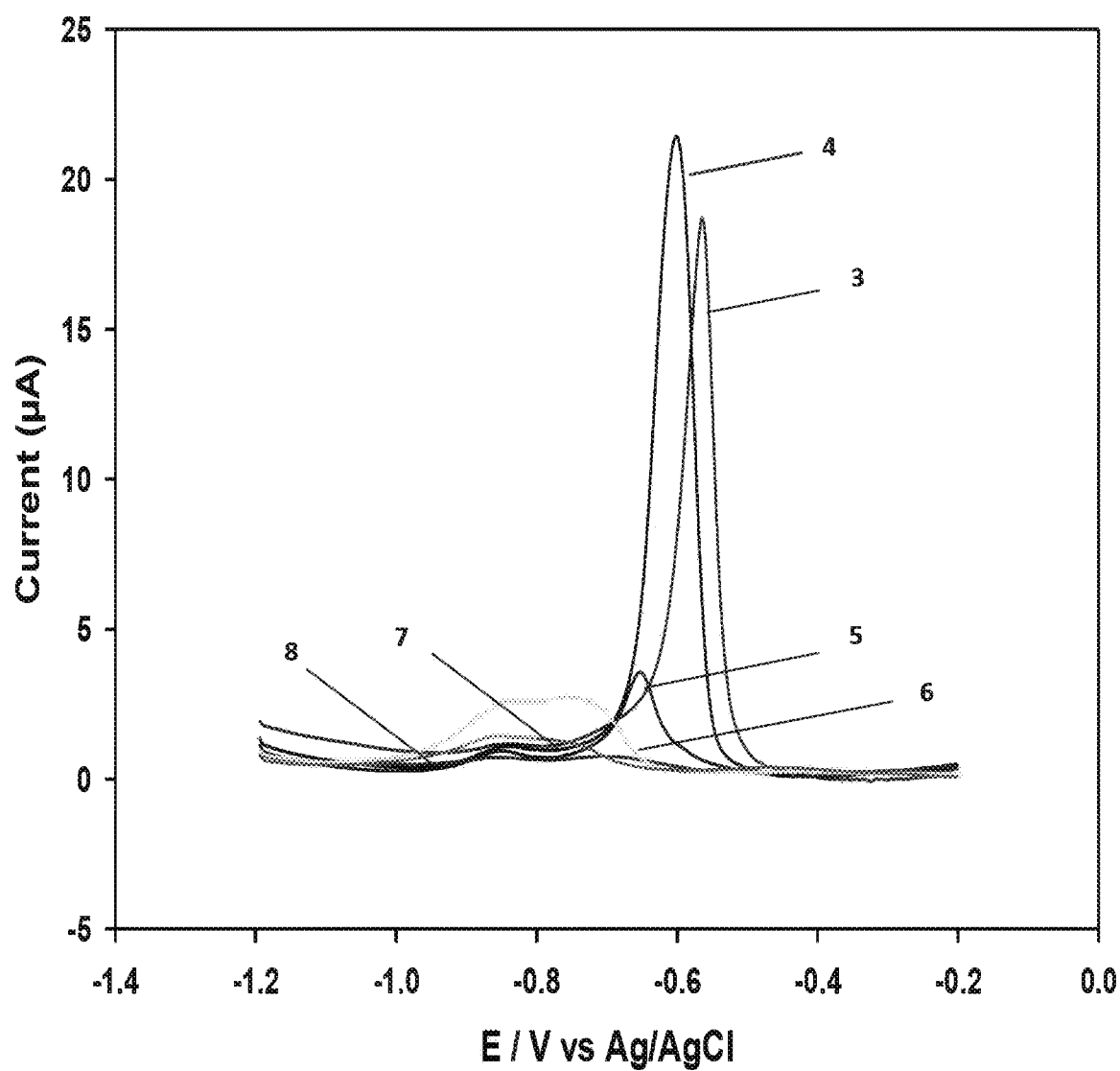
FIG. 58 illustrates the effect of varying pH values (3 to 8) on the square wave anodic stripping voltammetry (SWASV) voltammograms of 500 ppb Pb(II) in 0.1 M phosphate buffer at a 10 wt % Ce-MOR-15 zeolite modified carbon paste composite G electrode with the graphite:zeolite:paraffin ratio of 65:5:30 at an accumulation potential of −1.2 V, an accumulation time of 120 seconds, a potential step of 5 mV, an amplitude of 50 mV, and a frequency of 15 Hz.
Figure 59:
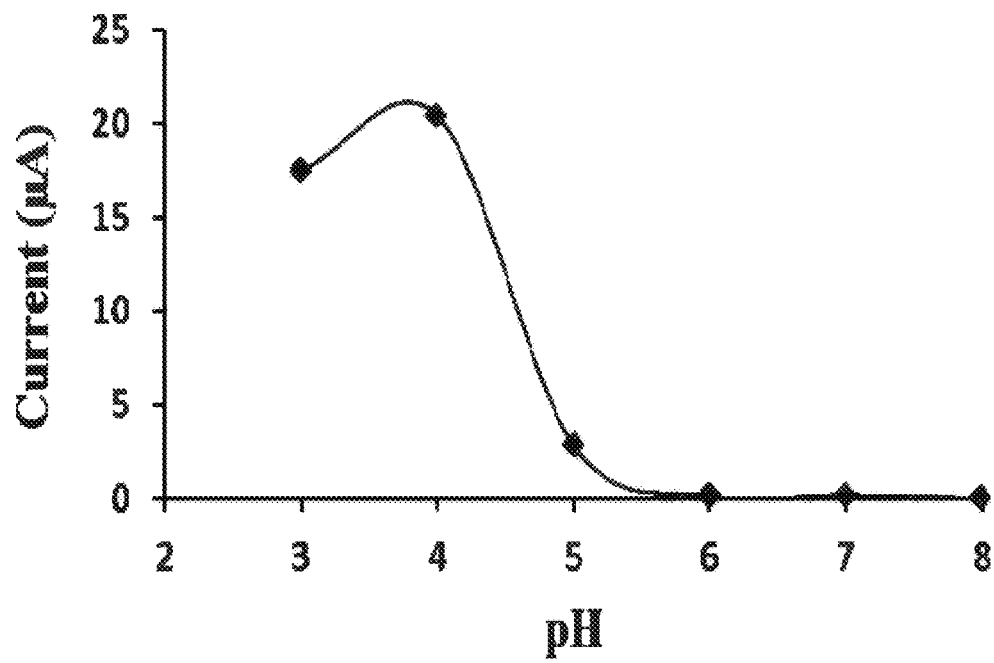
FIG. 59 is a plot of current for a 10 wt % Ce-MOR-15 zeolite modified carbon paste composite G electrode with the graphite:zeolite:paraffin ratio of 65:5:30 versus pH in 0.1 M phosphate buffer supporting electrolyte.

Square wave stripping voltammograms were also recorded at different pH values in 0.1 M phosphate buffer at composite B and composite G electrodes. The pH was varied between 3 and 8 by adjusting the buffer with $H_3PO_4$ and NaOH, respectively, until the desired pH value was reached. The pH of the electrolyte is important to the electroanalytical behavior of the composite electrodes. FIG. 56 shows the square wave anodic stripping voltammetry (SWASV) voltammograms at a lanthanum composite B electrode at pH values of 3-8. FIG. 57 is a plot of current for a lanthanum composite B electrode versus electrolyte pH values. FIG. 58 shows the square wave anodic stripping voltammetry (SWASV) voltammograms at a cerium composite G electrode at pH values of 3-8. FIG. 59 is a plot of current for a cerium composite G electrode versus electrolyte pH values. As can be seen from FIG. 56 and FIG. 58, there is a rise in peak height going from pH 3 to pH 4, and then a sudden drop at higher pH values (i.e. 5-8). The voltammetric signal of Pb at the composite electrodes depends on how well the electrode's surface could sense and detect the presence of free Pb(II) ions in the solution, i.e. oxidation process. As a result, the drop observed was attributed to the formation of insoluble $Pb_3(PO_4)_2$ which interferes with the detection of the Pb(II) ions as is observed in the voltammetric cell during the measurement. The peak potential (Ep) was also found to be pH dependent as a continuous shift was observed over the varied pH values. This is a characteristic of electrochemical systems in which hydrogen ion is consumed [Roque da Silva, A. M. S., et al., *Electrochemical studies and square wave adsorptive stripping voltammetry of the antidepressant fluoxetine*. Talanta, 1999. 49(3): p. 611-617.—incorporated herein by reference in its entirety]. The advantageous pH chosen therefore for subsequent use in this disclosure was pH=4 for both composite B and composite G electrodes.

Example 8

Voltammetric Determination of Pb(II) at a Prepared Lanthanum or Cerium Impregnated Zeolite Modified Carbon Paste Electrode (La/Ce-ZMCPE)

Figure 60:
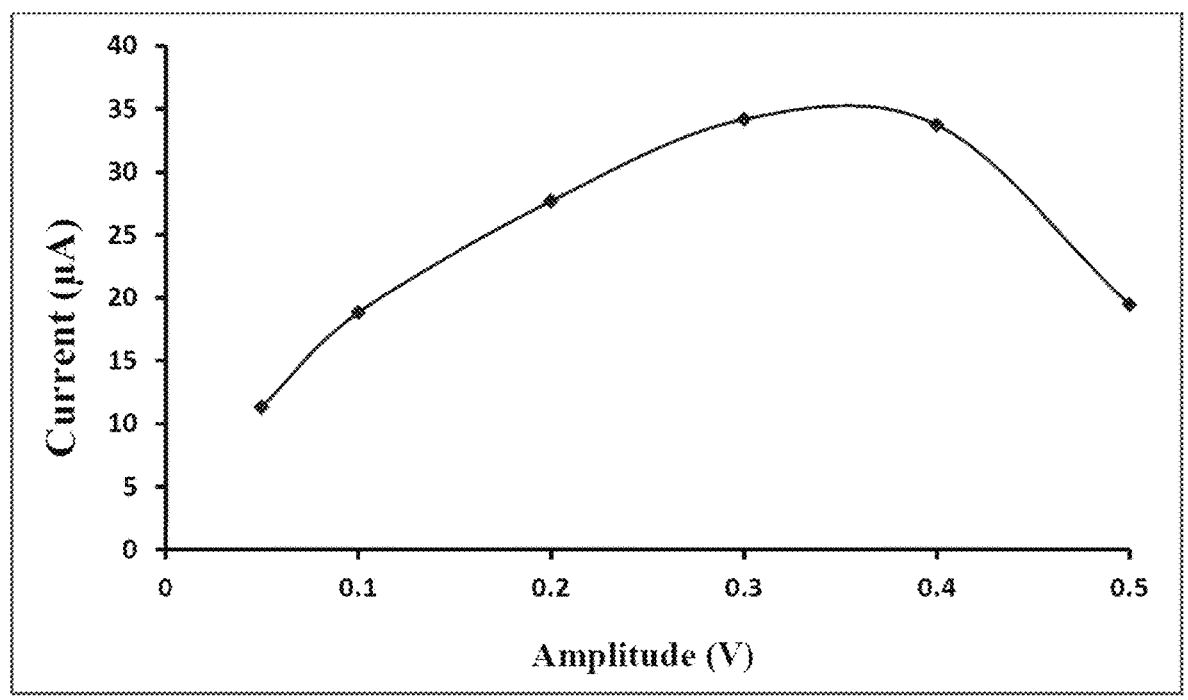
FIG. 60 is a plot of peak current versus amplitude and illustrates the effect of varying amplitude (0.05 V to 0.5 V) of 500 ppb Pb(II) in 0.1 M phosphate buffer (pH=4) at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, and a frequency of 15 Hz.
Figure 61:
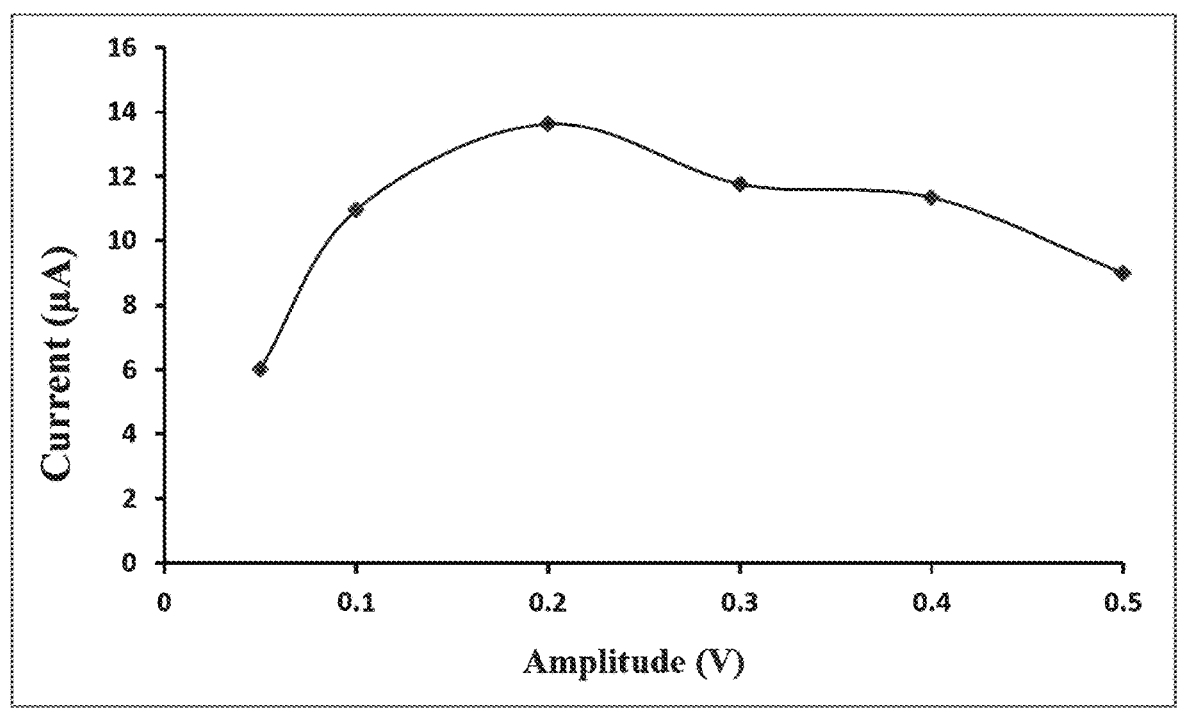
FIG. 61 is a plot of peak current versus amplitude and illustrates the effect of varying amplitude (0.05 V to 0.5 V) of 500 ppb Pb(II) in 0.1 M phosphate buffer (pH=4) at a 10 wt % Ce-MOR-15 zeolite modified carbon paste composite G electrode with the graphite:zeolite:paraffin ratio of 65:5:30 at an accumulation potential of −1.2 V, an accumulation time of 120 seconds, a potential step of 5 mV, and a frequency of 15 Hz.

In order to maximize the peak current with good resolution and a minimum peak width, the amplitude and frequency of the square wave were evaluated. Amplitude was varied from 0.05 V to 0.5 V at both composite B and composite G electrodes, while frequency was varied from 20 Hz to 200 Hz at the composite B electrode and 20 Hz to 180 Hz at the composite G electrode. It was observed that as the amplitude increases, the peak current also increases with a slight shift in peak potential until it reaches an apex at 0.3 V at the composite B electrode and 0.2 V at the composite G electrode. However, a broadened peak was obtained at those amplitudes. Therefore, a compromise was made in order to obtain a good resolution, a less broadened peak, and a maximum peak current. As a result, amplitudes of 0.1 V and 0.2 V were selected for composite B and composite G electrodes respectively. FIG. 60 and FIG. 61 show the effect of varying amplitude on peak current for both composite B and composite G electrodes respectively.

Figure 62:
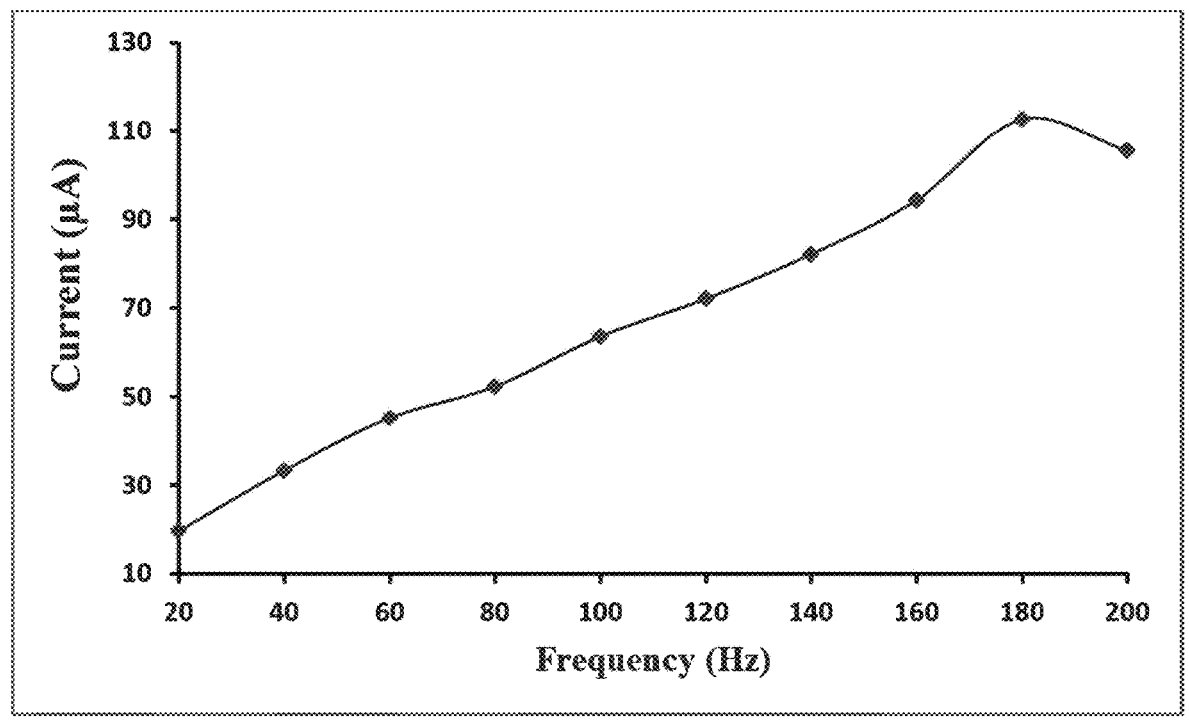
FIG. 62 is a plot of peak current versus frequency and illustrates the effect of varying frequency (20 Hz to 200 Hz) of 500 ppb Pb(II) in 0.1 M phosphate buffer (pH=4) at a 2 wt % La-MOR-15 zeolite modified carbon paste composite B electrode with the graphite:zeolite:paraffin ratio of 65:5:30 at an accumulation potential of −1.2 V, an accumulation time of 120 seconds, a potential step of 5 mV, and an amplitude of 300 mV.
Figure 63:
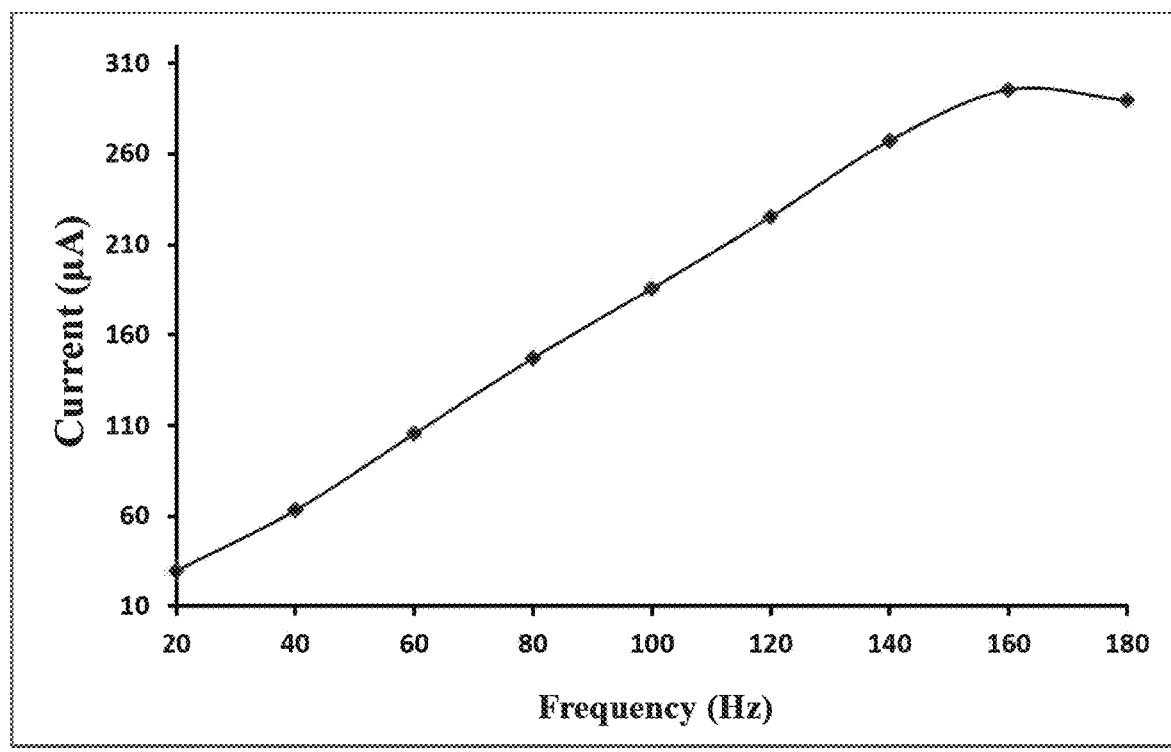
FIG. 63 is a plot of peak current versus frequency and illustrates the effect of varying frequency (20 Hz to 180 Hz) of 500 ppb Pb(II) in 0.1 M phosphate buffer (pH=4) at a 10 wt % Ce-MOR-15 zeolite modified carbon paste composite G electrode with the graphite:zeolite:paraffin ratio of 65:5.

In the same manner when the frequency was varied there was a corresponding increase in the peak current. FIG. 62 and FIG. 63 show the effect of varying frequency on peak current for both composite B and composite G electrodes respectively. The results for both composites reveal a linear relationship between the current and frequency up to 160 Hz for composite B (y=0.5122+11.736 (n=8) with $R^2$=0.9959), and up to 140 Hz for composite G (y=1.7818+0.5506 (n=8) with $R^2$=0.9994), then it increases slowly levelling off at 200 Hz for the composite B electrode and 180 Hz for the composite G electrode. However, at very high frequency the peak current became unstable due to large residual current, thereby giving a broadened peak. Therefore, similarly to amplitude, a compromise again had to be made. As such an advantageous frequency of 60 Hz and 40 Hz were selected for composite B and composite G electrodes respectively.

The effect of deposition potential of the analyte onto the surface of the working electrode was evaluated by varying the deposition potential from −1.6 V to −0.4 V at the composite B electrode and −1.4 V to −0.4 V at the composite G electrode. Deposition potential is one of the essential experimental parameters while carrying out stripping voltammetric determination of analytes such as Pb(II) ions. This is because unless an appropriate potential is applied to enable the reduction and deposition of the metal ions onto the surface of the electrode, the sensitivity of the electrode is greatly affected. The effect of deposition potential was studied elsewhere, and it was demonstrated that choosing a high potential in the negative direction leads to background hydrogen evolution which interferes with the analyte's signal. At the same time, too low of a potential is not enough to bring about the reduction of the metal ions. Therefore, the deposition potential needs to be evaluated to ensure that no hydrogen evolution occurs while also ensuring a reasonable amount of the analyte is deposited on the working electrode before being stripped. From the results of the square wave stripping analysis peak current at the composite B electrode (FIG. 64) and peak current at the composite G electrode (FIG. 65), an advantageous deposition potential which affords an effective pre-concentration of the analyte taking into consideration the peak height, peak shape, and peak width was chosen as −1.2 V for both composite B and composite G electrodes.

The deposition time dependence on the peak height was also examined for both composite B and composite G electrodes by varying the deposition time from 20 seconds to 180 seconds. It is generally accepted that lower detection limits can be reached with longer deposition times. However, longer deposition times can alter the surface of the electrode thereby affecting its analytical performance, as was evidenced in this procedure. FIG. 66 shows the effect of varying deposition time on peak current for the composite B electrode. FIG. 67 is a plot of current versus deposition time for the composite B electrode. FIG. 68 shows the effect of varying deposition time on peak current for the composite G electrode. FIG. 69 is a plot of current versus deposition time for the composite G electrode. As a result, a deposition time of 120 was adopted in the present disclosure for both composite B and composite G electrodes. In summary, the determined experimental parameters and conditions for the purposes of this disclosure are presented in Table 10.

TABLE 10

Summary of advantageous square wave anodic stripping voltammetry parameters for determination of Pb(II)

| Composite Electrode | Amplitude (V) | Frequency (Hz) | Deposition Potential (V) | Deposition Time (sec) |
|---|---|---|---|---|
| B | 0.1 | 60 | −1.2 | 120 |
| G | 0.2 | 40 | −1.2 | 120 |

Calibration curves were constructed for anodic stripping voltammetric detection of Pb(II) ion at the composite B and composite G electrodes over two concentration ranges (50-500 ppb and 5-50 ppb). FIG. 70 shows the square wave anodic stripping voltammetry (SWASV) voltammograms of Pb(II) over the concentration range 50-500 ppb for the composite B electrode. FIG. 71 shows the obtained calibration plot of Pb(II) over the calibration range of 50-500 ppb for the composite B electrode. FIG. 72 shows the SWASV voltammograms of Pb(II) over the concentration range 5-50 ppb for the composite B electrode. FIG. 73 shows the obtained calibration plot of Pb(II) over the calibration range of 5-50 ppb for the composite B electrode. FIG. 74 shows the square wave anodic stripping voltammetry SWASV voltammograms of Pb(II) over the concentration range 50-500 ppb for the composite G electrode. FIG. 75 shows the obtained calibration plot of Pb(II) over the calibration range of 50-500 ppb for the composite G electrode. FIG. 76 shows the SWASV voltammograms of Pb(II) over the concentration range 5-50 ppb for the composite G electrode. FIG. 77 shows the obtained calibration plot of Pb(II) over the calibration range of 5-50 ppb for the composite G electrode. The results of the square wave stripping voltammetry show a linear relationship between the stripping current and the concentration of Pb(II) ions at both the composite B and composite G electrodes. The $R^2$ values are equal to 0.9988 and 0.9991 for higher and lower concentration ranges respectively at the composite B electrode. The $R^2$ values are equal to 0.9994 and 0.9989 for higher and lower concentration ranges respectively at the composite G electrode. The limit of detection (S/N=3) for the composite B electrode was found as 0.225 ppb and for the composite G electrode was found as 0.07 ppb. Table 11 summarizes the results.

TABLE 11

Summary of results for Pb(II) detection at a prepared lanthanum or cerium impregnated zeolite modified carbon paste electrode (La/Ce-ZMCPE)

| Composite Electrode | Analyte | $R^2$ | Limit of Detection (LOD) (ppb) | Sensitivity ($\mu A\ L\ \mu g^{-1}$) |
|---|---|---|---|---|
| La-ZMCPE (Composite B) | Pb(II) | 0.9988 0.9991 | 0.225 | 0.051 |
| Ce-ZMCPE (Composite G) | Pb(II) | 0.9994 0.9989 | 0.07 | 0.047 |

The results from both the composite B and composite G electrodes were subjected to the F test in order to check the precision among them (Table 12). The F test compares the variances of the two methods (or the two composites in this case) and allows a conclusion to be drawn as to whether the results obtained agree with one another. For the composite electrodes evaluated in the present disclosure, it was found that at a 95% confidence level, there was no significant difference between the currents obtained for Pb(II) detection at both composites.

TABLE 12

F test results for precision of prepared lanthanum or cerium impregnated zeolite modified carbon paste electrodes (La/Ce-ZMCPEs)
F-Test
Two Sample for Variances

|  | Ce-ZMCPE (Composite G) | La-ZMCPE (Composite B) |
|---|---|---|
| Mean | 12.89 | 12.17 |
| Variance | 258.24 | 189.52 |
| Observations | 12 | 12 |
| Degree of freedom | 11 | 11 |
| F | 1.36 |  |
| P (F <= f) | 0.308 |  |
| F Critical | 2.81 |  |

The reproducibility of the stripping analysis for Pb(II) at both composite B and composite G electrodes was also checked by carrying out five consecutive measurements with a single electrode. The relative standard deviation (RSD) for both composites was found as 3.02% for the composite B electrode and 2.23% at the composite G electrode, implying good reproducibility of the electrodes for Pb(II) detection. When comparing the analytical performance of the electrodes in the current study with other electrodes that have been reported previously, it was found that the composites of the present disclosure compare favorably among other composites reported in the literature. Table 13 summarizes a comparison of the level of detection (LOD) of the composite electrodes of the present disclosure with other composites from the literature.

TABLE 13

Comparison of detection limits of a prepared lanthanum or cerium impregnated zeolite modified carbon paste electrode (La/Ce-ZMCPE) with previously reported composite electrodes

| Electrode Type | Metal detected | Technique | Detection Limit (ppb) | Ref. |
|---|---|---|---|---|
| La-ZMCPE | Pb(II) | SWASV | 0.225 | Current |
| Ce-ZMCPE | Pb(II) | | 0.07 | Disclosure |
| Carbon screen printed electrode modified by Bi-nanoparticle | Pb(II) | SWASV | 0.9 | Rico, et al. |
| Boron-doped diamond electrode | Pb(II) | DPASV | 1.15 | El Tall, et al. |
| Bi-modified carbon paste electrode | Pb(II) | SWASV | 0.8 | Svancara. et al. |
| Bi-film electrode | Pb(II) | SWASV | 6.9 | Sirianglthawut, et al. |
| Nafion-coated Bi-film electrode | Pb(II) | SWASV | 2 | Kefala, et al. |
| Bi nano-powder electrode | Pb(II) | SWASV | 0.15 | Lee, et al. |

Example 9

Simultaneous Detection of Pb(II) and Cd(II) at a Prepared Lanthanum or Cerium Impregnated Zeolite Modified Carbon Paste Electrode (La/Ce-ZMCPE)

To further investigate the sensitivities of the composite electrodes of the present disclosure, simultaneous detection of two metal ions Pb(II) and Cd(II) was carried out. The aim of this was to investigate if the detection of a given analyte interferes with the detection of the other analyte. FIG. 78 shows the SWASV voltammograms of Cd(II) and Pb(II) over the concentration range 50-500 ppb for the lanthanum composite B electrode. FIG. 79 shows the obtained calibration plot of Cd(II) and Pb(II) over the calibration range of 50-500 ppb for the lanthanum composite B electrode. FIG. 80 shows the SWASV voltammograms of Cd(II) and Pb(II) over the concentration range 50-500 ppb for the cerium composite G electrode. FIG. 81 shows the obtained calibration plot of Cd(II) and Pb(II) over the calibration range of 50-500 ppb for the cerium composite G electrode. The results of the simultaneous determinations give a relatively linear relationship between the current and the concentration of the analyte ions. Table 14 gives the results of the $R^2$ values and level of detection (LOD). Comparing the results of the individual analysis to the simultaneous analysis, it is observed that the detection limits and sensitivities of the composite B electrode were affected by the simultaneous analysis, while the detection limits and sensitivities of the composite G electrode were not greatly affected. Therefore, one can conclude that the composite G electrode can be applied for either individual determination of Pb(II) or simultaneous determination of Pb(II) and Cd(I) ions in aqueous samples.

TABLE 14

Summary of results for simultaneous Cd (II) and Pb(II) determination at a prepared lanthanum or cerium impregnated zeolite modified carbon paste electrode (La/Ce-ZMCPE)

| Composite | Analyte | $R^2$ | LOD (ppb) | Sensitivity ($\mu$A L $\mu g^{-1}$) |
|---|---|---|---|---|
| La-ZMCPE (Composite B) | Cd(II) | 0.9985 | 0.122 | 0.1785 |
| | Pb(II) | 0.9978 | 0.240 | 0.1287 |
| Ce-ZMCPE (Composite G) | Cd(II) | 0.9976 | 0.046 | 0.0861 |
| | Pb(II) | 0.9978 | 0.045 | 0.0717 |

In conclusion, rare earth impregnated zeolite modified carbon paste electrodes (RE-ZMCPEs) were successfully investigated as an alternative electrode for the anodic stripping voltammetric determination of Pb(II) and Cd(II) ions. Prior to the fabrication of the RE-ZMCPEs, mordenite zeolite with a silica to alumina ratio of 15 was synthesized and characterized by XRD, SEM, EDX, and NMR, the results of which show that a flat prismic crystal was obtained with an average crystal size of 6.8 rpm. Preliminary screening of the fabricated electrodes showed that the electrodes with 2 wt % La impregnation at 10 wt % Ce impregnation, and a composite ratio of 65:5:30 (graphite to zeolite to paraffin) gave a desired peak height and were thus adopted for this procedure. Deposition of the heavy metal ion or analyte of interest onto the surface of the electrodes was accomplished by holding the electrode at a potential of −1.2 V (compared to Ag/AgCl) for 120 seconds followed by a square wave stripping scan from −1.6 to 0 V. Calibration curves for Pb(II) and Cd(II) gave a linear relationship at both composite electrodes with correlation coefficients of 0.9978 and 0.9985 for Pb(II) and Cd(I) at La-ZMCPE and 0.9978 and 0.9976 at Ce-ZMCPE for Pb(II) and Cd(II), respectively and detection limits of 0.225 $\mu$g L$^{-1}$, and 0.122 $\mu$g L$^{-1}$ at the La-ZMCPE for Pb(II) and Cd(II) detection, and 0.07 $\mu$g L$^{-1}$, and 0.046 $\mu$g L$^{-1}$ at the Ce-ZMCPE for Pb(II) and Cd(II) detection, respectively. The reproducibility of the composite electrodes investigated by carrying out five consecutive runs using a single electrode gave a relatively good precision with RSD values of 3.02% and 2.23% for La-ZMCPE and Ce-ZMCPE for Pb(II) detection respectively. Based on the results of the calibration plots, limits of detection, sensitivities and reproducibility, the composite electrodes in this disclosure demonstrate the ability of being used for analysis of environmental samples such as drinking water due to their inexpensiveness and ease of fabrication as well as lack of toxicity compared to mercury based electrodes used in stripping analysis.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:
1. An electrode, comprising:
   graphite powder;
   paraffin oil; and
   a mordenite zeolite impregnated with a rare earth metal;
   wherein the rare earth metal is at least one selected from the group consisting of lanthanum and cerium; and wherein the mordenite zeolite impregnated with the rare earth metal is present in an amount of 4-5% by weight relative to a total weight of the electrode.

2. The electrode of claim 1, wherein the mordenite zeolite has a silica to alumina ratio in the range of 5 to 40.

3. The electrode of claim 1, wherein the rare earth metal is lanthanum.

4. The electrode of claim 1, wherein the mordenite zeolite impregnated with the rare earth metal has a weight percentage of the rare earth metal in the range of 1-15% relative to the total weight of the mordenite zeolite impregnated with the rare earth metal.

5. The electrode of claim 1, which has a weight percentage of the graphite powder in the range of 60 to 70% relative to the total weight of the electrode.

6. The electrode of claim 1, which has a weight percentage of the paraffin oil in the range of 26-34% relative to the total weight of the electrode.

7. The electrode of claim 1, which has a 10-40% greater electroactive surface area relative to an identical electrode except that it contains a zeolite which is not impregnated with the rare earth metal.

8. A method for detecting and quantifying a heavy metal ion in an aqueous solution, comprising:
    contacting the aqueous solution with the electrode of claim 1;
    generating a negative deposition potential at the electrode to reduce the heavy metal ion and form a reduced heavy metal that is deposited onto the electrode;
    scanning a potential range from the negative deposition potential in the positive direction at the electrode to oxidize and strip the reduced heavy metal from the electrode; and
    measuring the current during the scanning.

9. The method of claim 8, wherein the heavy metal ion is at least one selected from the group consisting of Pb(II) and Cd(II).

10. The method of claim 8, wherein the scanning and the measuring are performed with square wave voltammetry.

11. The method of claim 8, wherein the negative deposition potential is in the range of −2.0 V to −0.2 V.

12. The method of claim 8, wherein the scanning is performed at a scan rate of 2-500 mV s$^{-1}$.

13. The method of claim 8, wherein the reduced heavy metal is deposited over a time period in the range of 10-250 seconds.

14. The method of claim 8, wherein the aqueous solution has a pH in the range of 3-5.

15. The method of claim 8, wherein the rare earth metal is lanthanum and the heavy metal ion is Pb(II), and the method has a Pb(II) detection limit in the range of 0.15-0.30 μg L$^{-1}$.

16. The method of claim 8, wherein the rare earth metal is lanthanum and the heavy metal ion is Cd(II), and the method has a Cd(II) detection limit in the range of 0.05-0.20 μg L$^{-1}$.

17. The method of claim 8, wherein the rare earth metal is cerium and the heavy metal ion is Pb(II), and the method has a Pb(II) detection limit in the range of 0.02-0.15 μg L$^{-1}$.

18. The method of claim 8, wherein the rare earth metal is cerium and the heavy metal ion is Cd(II), and the method has a Cd(II) detection limit in the range of 0.01-0.10 μg L$^{-1}$.

19. The method of claim 8, which has a reproducibility as measured by a relative standard deviation in the range of 1-5%.

20. The electrode of claim 1, wherein the rare earth metal is lanthanum and wherein a weight percentage of lanthanum is 1.5-5% relative to the total weight of the mordenite zeolite impregnated with the rare earth metal.

\* \* \* \* \*